(12) United States Patent
Kasinath et al.

(10) Patent No.: US 11,793,907 B2
(45) Date of Patent: *Oct. 24, 2023

(54) ORTHOPEDIC IMPLANT HAVING A CRYSTALLINE GALLIUM-CONTAINING HYDROXYAPATITE COATING AND METHODS FOR MAKING THE SAME

(71) Applicant: DePuy Synthes Products, Inc., Raynham, MA (US)

(72) Inventors: Rajendra Kasinath, Warsaw, IN (US); Craig Ernsberger, Warsaw, IN (US); Stephanie Vass, Warsaw, IN (US); Steven N. Ginn, Granger, IN (US); Haibo Qu, Warsaw, IN (US); Weidong Tong, Warsaw, IN (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 101 days.

This patent is subject to a terminal disclaimer.

(21) Appl. No.: 17/474,610

(22) Filed: Sep. 14, 2021

(65) Prior Publication Data

US 2021/0402055 A1 Dec. 30, 2021

Related U.S. Application Data

(60) Continuation of application No. 16/725,444, filed on Dec. 23, 2019, now Pat. No. 11,141,505, which is a division of application No. 15/472,186, filed on Mar. 28, 2017, now Pat. No. 10,537,658.

(51) Int. Cl.
| | | |
|---|---|---|
| *A61L 27/12* | (2006.01) | |
| *A61L 27/04* | (2006.01) | |
| *A61L 27/02* | (2006.01) | |
| *A61L 27/06* | (2006.01) | |
| *A61L 27/32* | (2006.01) | |
| *A61L 27/50* | (2006.01) | |
| *A61L 27/56* | (2006.01) | |
| *A61L 27/58* | (2006.01) | |

(52) U.S. Cl.
CPC .......... *A61L 27/12* (2013.01); *A61L 27/025* (2013.01); *A61L 27/045* (2013.01); *A61L 27/047* (2013.01); *A61L 27/06* (2013.01); *A61L 27/32* (2013.01); *A61L 27/50* (2013.01); *A61L 27/56* (2013.01); *A61L 27/58* (2013.01)

(58) Field of Classification Search
CPC .......... A61L 27/12; A61L 27/56; A61L 27/50; A61L 27/045; A61L 27/58; A61L 27/32; A61L 27/025; A61L 27/047; A61L 27/06; A61L 2420/02; A61L 2400/18; A61L 2430/02

See application file for complete search history.

(56) References Cited

U.S. PATENT DOCUMENTS

| | | |
|---|---|---|
| 5,015,817 A | 5/1991 | Kranz |
| 5,164,187 A | 11/1992 | Constantz et al. |
| 5,300,281 A | 4/1994 | McMillan et al. |
| 5,478,237 A | 12/1995 | Ishizawa |
| 5,558,517 A | 9/1996 | Shalaby et al. |
| 5,612,049 A | 3/1997 | Li et al. |
| 5,675,001 A | 10/1997 | Hoffman et al. |
| 5,691,397 A | 11/1997 | Glimcher et al. |
| 5,702,484 A | 12/1997 | Goymann et al. |
| 5,702,487 A | 12/1997 | Averill et al. |
| 5,763,092 A | 6/1998 | Lee et al. |
| 5,769,897 A | 6/1998 | Haerle |
| 5,944,757 A | 8/1999 | Grammont |
| 5,958,430 A | 9/1999 | Campbell et al. |
| 5,997,912 A | 12/1999 | Schlesinger et al. |
| 6,008,431 A | 12/1999 | Caldarise et al. |
| 6,013,591 A | 1/2000 | Ying et al. |
| 6,027,743 A | 2/2000 | Khouri et al. |
| 6,059,833 A | 5/2000 | Doets |
| 6,066,628 A | 5/2000 | Stojiljkovic et al. |
| 6,126,690 A | 10/2000 | Ateshian et al. |
| 6,139,585 A | 10/2000 | Li |
| 6,146,686 A | 11/2000 | Leitao |
| 6,153,664 A | 11/2000 | Wise et al. |
| 6,203,822 B1 | 3/2001 | Schjlesinger et al. |
| 6,207,218 B1 | 3/2001 | Layrolle et al. |

(Continued)

FOREIGN PATENT DOCUMENTS

| | | |
|---|---|---|
| BY | 20347 C1 | 8/2016 |
| CN | 101757689 A | 6/2010 |

(Continued)

OTHER PUBLICATIONS

Japanese Search Report for Corresponding Japanese Application No. 2018-059429, dated Apr. 19, 2022, 4 Pages.

Zitelli, et al; A Novel Method for Solution Deposition of Hydroxyapatite on to Three Dimensionally Porous Metallic Surfaces: Peri-Apatite Ha; Jan. 2000; Materials Research Society Symposia Proceedings. Materials Research Society 599: 117-128.

Japanese Search Report for Japanese Application No. 2008-059413, dated Dec. 21, 2021, 2 Pages.

Chinese Seach Report for Corresponding Chinese Application No. 201810264312.1, dated Jul. 14, 2021, 2 Pages.

(Continued)

*Primary Examiner* — Abigail Vanhorn

(57) ABSTRACT

An orthopedic implant having a metal surface and a hydroxyapatite layer comprising gallium ions therein disposed on at least part of the metal surface is described. The hydroxyapatite layer has an average crystallite size of less than about 75 nm in at least one direction and dissolves for more than 2 hours in vitro. The hydroxyapatite layer is substantially free of carbonate. The coating, which is formed on a sodium titanate surface, has increased shear strength and tensile strength. The coating is formed by a solution deposited hydroxyapatite process under inert conditions. The pH of the solution varies by less than 0.1 pH unit/hour during coating formation.

15 Claims, 21 Drawing Sheets

(56) References Cited

U.S. PATENT DOCUMENTS

| | | |
|---|---|---|
| 6,231,612 B1 | 5/2001 | Balay et al. |
| 6,261,322 B1 | 7/2001 | Despres et al. |
| 6,280,478 B1 | 8/2001 | Richter et al. |
| 6,280,789 B1 | 8/2001 | Rey et al. |
| 6,312,472 B1 | 11/2001 | Hall et al. |
| 6,319,255 B1 | 11/2001 | Grundei et al. |
| 6,319,286 B1 | 11/2001 | Fernandez et al. |
| 6,364,884 B1 | 4/2002 | Bowman et al. |
| 6,395,037 B1 | 5/2002 | Akashi et al. |
| 6,402,766 B2 | 6/2002 | Bowman et al. |
| 6,419,708 B1 | 7/2002 | Hall et al. |
| 6,436,110 B2 | 8/2002 | Bowman et al. |
| 6,488,716 B1 | 12/2002 | Huang et al. |
| 6,497,707 B1 | 12/2002 | Bowman et al. |
| 6,511,510 B1 | 1/2003 | De Bruijn et al. |
| 6,520,964 B2 | 2/2003 | Talarida et al. |
| 6,569,489 B1 | 5/2003 | Li |
| 6,592,624 B1 | 7/2003 | Fraser et al. |
| 6,596,338 B2 | 7/2003 | Scott et al. |
| 6,602,293 B1 | 8/2003 | Biermann et al. |
| 6,610,095 B1 | 8/2003 | Pope et al. |
| 6,620,200 B1 | 9/2003 | Descamps et al. |
| 6,679,917 B2 | 1/2004 | Ek |
| 6,709,462 B2 | 3/2004 | Hanssen |
| 6,719,989 B1 | 4/2004 | Matsushima et al. |
| 6,736,849 B2 | 5/2004 | Li et al. |
| 6,764,769 B2 | 7/2004 | Kotte et al. |
| 6,846,327 B2 | 1/2005 | Khandkar et al. |
| 6,875,461 B2 | 4/2005 | Tanaka et al. |
| 6,908,486 B2 | 6/2005 | Lewallen |
| 6,911,048 B2 | 6/2005 | Fernandez et al. |
| 6,942,701 B2 | 9/2005 | Taylor |
| 7,044,976 B2 | 5/2006 | Meswania |
| 7,051,417 B2 | 5/2006 | Michelson |
| 7,087,086 B2 | 8/2006 | Li et al. |
| 7,105,030 B2 | 9/2006 | Despres, III et al. |
| 7,155,143 B2 | 10/2006 | Michelson |
| 7,192,448 B2 | 3/2007 | Ferree |
| 7,226,480 B2 | 6/2007 | Thalgott |
| 7,241,315 B2 | 7/2007 | Evans |
| 7,244,275 B2 | 7/2007 | Michelson |
| 7,341,756 B2 | 3/2008 | Liu et al. |
| 7,497,875 B1 | 3/2009 | Zweymller |
| 7,521,436 B2 | 4/2009 | Bujoli et al. |
| 7,767,250 B2 | 8/2010 | Luan et al. |
| 7,892,286 B2 | 2/2011 | Michelson |
| 7,892,290 B2 | 2/2011 | Bergin et al. |
| 7,935,116 B2 | 5/2011 | Michelson |
| 7,998,219 B2 | 8/2011 | Riman et al. |
| 8,002,842 B2 | 8/2011 | Ronk |
| 8,021,433 B2 | 9/2011 | Meswania et al. |
| 8,044,037 B2 | 10/2011 | Bujoli et al. |
| 8,067,069 B2 | 11/2011 | Li |
| 8,071,156 B2 | 12/2011 | Weber et al. |
| 8,177,842 B2 | 5/2012 | Strzepa et al. |
| 8,187,304 B2 | 5/2012 | Malek |
| 8,252,062 B2 | 8/2012 | Bandoh et al. |
| 8,292,967 B2 | 10/2012 | Brown et al. |
| 8,303,879 B2 | 11/2012 | Bertele et al. |
| 8,323,348 B2 | 12/2012 | Lai et al. |
| 8,329,202 B2 | 12/2012 | Venu et al. |
| 8,399,008 B2 | 3/2013 | Webster et al. |
| 8,414,547 B2 | 4/2013 | Difiore et al. |
| 8,414,650 B2 | 4/2013 | Bertele et al. |
| 8,486,151 B2 | 7/2013 | Theillez et al. |
| 8,491,936 B2 | 7/2013 | Rabiei et al. |
| 8,506,644 B1 | 8/2013 | Ho Bo Tho et al. |
| 8,512,732 B2 | 8/2013 | Yao et al. |
| 8,535,751 B2 | 9/2013 | Gillesberg |
| 8,556,972 B2 | 10/2013 | Gordon et al. |
| 8,623,311 B2 | 1/2014 | Bujoli et al. |
| 8,628,584 B2 | 1/2014 | Blunn et al. |
| 8,637,090 B2 | 1/2014 | Ohtake et al. |
| 8,641,773 B2 | 2/2014 | Bergin et al. |
| 8,647,390 B2 | 2/2014 | Bellemere et al. |
| 8,663,329 B2 | 3/2014 | Ernst |
| 8,696,759 B2 | 4/2014 | Tong et al. |
| 8,702,806 B2 | 4/2014 | Bailey et al. |
| 9,975,772 B2 | 5/2018 | Kjellin |
| 10,537,658 B2* | 1/2020 | Kasinath .......... A61L 27/32 |
| 10,537,661 B2* | 1/2020 | Kasinath .......... A61L 27/06 |
| 11,058,799 B2* | 7/2021 | Kasinath .......... A61L 27/54 |
| 11,141,505 B2* | 10/2021 | Kasinath .......... A61L 27/58 |
| 2002/0035402 A1 | 3/2002 | De Bruijn et al. |
| 2002/0134667 A1 | 9/2002 | Driskell et al. |
| 2003/0021825 A1 | 1/2003 | Pathak et al. |
| 2003/0108658 A1 | 6/2003 | Andersch et al. |
| 2003/0170378 A1 | 9/2003 | Wen |
| 2004/0023784 A1 | 2/2004 | Yu et al. |
| 2004/0053197 A1 | 3/2004 | Minevski et al. |
| 2004/0166139 A1 | 8/2004 | Stroosnijder et al. |
| 2004/0171471 A1 | 9/2004 | Nrenberg et al. |
| 2005/0100578 A1 | 5/2005 | Schmid et al. |
| 2006/0134160 A1 | 6/2006 | Troczynski et al. |
| 2007/0055380 A1 | 3/2007 | Berelsman et al. |
| 2008/0097618 A1 | 4/2008 | Baker et al. |
| 2008/0152783 A1 | 6/2008 | Andersch et al. |
| 2008/0220233 A1 | 9/2008 | Kjellin et al. |
| 2009/0276056 A1 | 11/2009 | Bose et al. |
| 2009/0280156 A1 | 11/2009 | Hotokebuchi et al. |
| 2010/0040668 A1 | 2/2010 | Riman et al. |
| 2010/0075068 A1 | 3/2010 | Suzuoka |
| 2010/0112208 A1 | 5/2010 | Malik et al. |
| 2010/0216697 A1 | 8/2010 | Duewelhenke |
| 2010/0248191 A1 | 9/2010 | Bujoli et al. |
| 2011/0020419 A1 | 1/2011 | Yuan et al. |
| 2011/0038809 A1 | 2/2011 | Perl et al. |
| 2011/0135621 A1 | 6/2011 | Miller et al. |
| 2012/0064170 A1 | 4/2012 | Bujoli |
| 2012/0088100 A1 | 4/2012 | Ha et al. |
| 2012/0111226 A1 | 5/2012 | Bujoli et al. |
| 2012/0128729 A1 | 5/2012 | Ohtake et al. |
| 2012/0245135 A1 | 9/2012 | Thottathil et al. |
| 2012/0270031 A1 | 10/2012 | Guan et al. |
| 2012/0288699 A1 | 11/2012 | Ahlberg et al. |
| 2013/0078476 A1 | 3/2013 | Riman et al. |
| 2013/0110252 A1 | 5/2013 | Bake et al. |
| 2013/0209377 A1 | 8/2013 | Tas |
| 2013/0209537 A1 | 8/2013 | Fu-Giles |
| 2013/0247357 A1 | 9/2013 | Bertele et al. |
| 2013/0251982 A1 | 9/2013 | Kjellin et al. |
| 2013/0266629 A1 | 10/2013 | Arvidsson |
| 2013/0273135 A1 | 10/2013 | Brooks et al. |
| 2013/0302427 A1 | 11/2013 | Arvidsson et al. |
| 2013/0345827 A1 | 12/2013 | Wallick |
| 2014/0087004 A1 | 3/2014 | Bujoli et al. |
| 2014/0308628 A1 | 10/2014 | Carrado et al. |
| 2018/0208057 A1 | 10/2018 | Kasinath et al. |
| 2020/0139008 A1 | 5/2020 | Kasinath |
| 2021/0299328 A1* | 9/2021 | Kasinath .......... A61L 27/045 |

FOREIGN PATENT DOCUMENTS

| | | |
|---|---|---|
| DE | 102012210804 A1 | 1/2014 |
| EP | 375600 A2 | 6/1990 |
| EP | 450939 A2 | 10/1991 |
| EP | 532421 A1 | 3/1993 |
| EP | 578345 A1 | 1/1994 |
| EP | 743050 A1 | 11/1996 |
| EP | 764168 A1 | 3/1997 |
| EP | 900552 A1 | 3/1999 |
| EP | 1099426 A1 | 5/2001 |
| EP | 554301 B1 | 7/2001 |
| EP | 1136045 A2 | 9/2001 |
| EP | 1151732 A1 | 11/2001 |
| EP | 1207820 A1 | 5/2002 |
| EP | 1216667 A1 | 6/2002 |
| EP | 1011541 B1 | 10/2003 |
| EP | 1433443 A1 | 6/2004 |
| EP | 1168989 B1 | 9/2004 |
| EP | 1178765 B1 | 9/2004 |
| EP | 1527758 A1 | 5/2005 |
| EP | 1649834 A1 | 4/2006 |
| EP | 1786484 B1 | 2/2008 |

(56) References Cited

FOREIGN PATENT DOCUMENTS

| EP | 1731115 B1 | 3/2008 |
|---|---|---|
| EP | 1917051 B1 | 6/2010 |
| EP | 2219696 A1 | 8/2010 |
| EP | 228079 A1 | 9/2010 |
| EP | 2296718 B1 | 3/2013 |
| JP | H03-097466 | 4/1991 |
| JP | 2000-210313 | 1/1999 |
| JP | H11-323570 A | 11/1999 |
| JP | 2005021208 A | 1/2005 |
| JP | 2006131469 A | 5/2006 |
| RU | 2194536 C1 | 12/2002 |
| RU | 2423150 C1 | 7/2011 |
| RU | 2476243 C1 | 2/2013 |
| RU | 134039 U1 | 11/2013 |
| RU | 256060 C1 | 10/2015 |
| RU | 2608461 C2 | 1/2017 |
| WO | 9110437 A1 | 7/1991 |
| WO | 02085385 A2 | 10/2002 |
| WO | 03061579 A2 | 7/2003 |
| WO | 2005058331 A1 | 6/2005 |
| WO | 2007085852 A2 | 8/2007 |
| WO | 2007087461 A2 | 8/2007 |
| WO | 2009024778 A2 | 2/2009 |
| WO | 2009111300 A2 | 9/2009 |
| WO | 2009111307 A2 | 9/2009 |
| WO | 2010100209 A1 | 9/2010 |
| WO | 2011035434 A1 | 3/2011 |
| WO | 2014027612 A1 | 2/2014 |

OTHER PUBLICATIONS

Alt, V. et al., "The effects of combined gentamicin-hydroxyapatite coating for cementless joint prostheses on the reduction of infection rates in a rabbit infection prophylaxis model", Biomaterials, 2006, 27, 4627-4634.

Kurtjak et al., Biocompatible nano-gallium/hydroxapatiet nanocomposite with antimicrobial activity, J. Matter. Sci: Mater Med, 27:170, pp. 1-13 (Year: 2016).

Kumar et al., "Temperature Driven Morphological Changes of Chemicallly Precipated Hydroxapatite Nanoparticles." Langmuir, vol. 20, No. 13, 2004, 5196-5200.

Tung, M. et al., "An intermediate State in Hydrolysis of Amorphous Calcium Phosphate." Calcified Tissue International, 19832, 35, 783-790.

Blumenthal, N. et al., "Effect of gallium on the in vitro formation, growth, solubility of hydroxypatite." Calcified Tissue International, 1989, 45, 81-87.

Manca, S.G. et al., "Uber den Einbau von Al(III), Ga (III) und in (III) in das Calcium-Fluoroapatit-Gitter." Naturforsch, 1991, 46b, 129-131.

Cuisiner, F.J.G. et al., "High resolution electron microscopic study of Ga-containing carbonate apattite," Journal of Crystal Growth, 1991, 125, 1-6.

Li, P. "Biomimetic nano-apatite coating capable of promoting bone ingrowth." J. Biomedical Materials Research, 2003, 66A, 79-85.

Korbas, M. et al., "Bone tissue incorporates in vitro gallium with a local structure similar to gallium-doped brushite." Journal Biol Inorg Chem, 2004, 9, 67-76.

Melnikov, P. et al., "Gallium-containing hydroxyapatite for potential use in orthopedics," Materials Chemistry and Physics, 2009, 117, 86-90.

Kolmas, J. et al., "Substituted Hydroxyapatites with Antibacterial Properties." BioMed Research International, 2014, Article ID 178123, 15 pages.

Inagaki, M. et al., "Phase transformation of plasma-sprayed hydroxyapaptite coating with preferred crystalline orientation," Biomaterials, 2007, 28, 2923-2931.

Bernstein, L.R., "Mechanisms of Therapeutic Activity for Gallium,"Pharmacological Reviews, 1999, 50,665-82.

Mellier, C. et al., "Design and properties of novel gallium-doped injectable apatitic cements," Acta Biomaterialiia, 2015, 23, 322-332.

Donnelly, R. et al., "The Effect of Gallium on Seeded Hydroxyapatite Growth," Calcif. Tissue Int., 1989, 44, 138-142.

Esenli et al., "X-Ray Diffraction Intensity Ratios I(111)/I(311) of Natual Heulandites and Clinoptiloilites,"Clays and Clay Minerals, vol. 46, No. 6, 1998, 678-686.

Kumar et al., "Chitosan-mediated crystalization and assembly of hydroxyapatite nanoparticles into hybrid nanostructured films," J.R. Soc. Interface (2008) 5, 427-439.

Charlotte Mellier et al., "Design and properties of novel gallium-doped injectable apatitic cements", Acta Biomaterialia, vol. 24, pp. 322-332, 2015, 11 pages.

Gabriela Ciobanu et al., "Structural characterization of hydroxyapatite layer coatings on titanium supports", Surface & Coatings Technology, vol. 202, pp. 2467-2470, 4 pages.

P. Melnikov et al., "Gallium-containing hydroxyapatite for potential use in orthopedics", Materials Chemistry and Physics, vol. 117, Issue 1, pp. 86-90, Sep. 15, 2009, 5 pages.

European Search Report, European Application No. 18161429.8-1109, dated Aug. 27, 2018, 10 pages.

European Search Report, European Application No. 18161421.5-1109, dated Aug. 14, 2018, 10 pages.

Declaration of Rajendra Kasinath pursuant to 37 C.F.R. 1.132 dated Apr. 25, 2019, filed in U.S. Appl. No. 15/427,189, 8 pages.

European Search Report and Opinion for EP20198560.3 dated Dec. 14, 2020, 10 pages.

Duan, et al., "A new evaporation-based method for the preparation of biomimetic calcium phosphate coatings on metals11," Materials Science and Engineering C, 2009, 29, 334-1337.

Bral, et al., "In vivo biofunctionalization of titanium patient-specific implants with nano hydroxyapatite and other nano calcium phosphate coatings: a systematic review," Journal of Cranio-Maxillo-Facial Surgery, 2016, 44, 400-412.

Dhondt, C. L., R.M.H. Verbeeck, and E.A. P. De Maeyer. "The growth of non-stoichiometric apatites using the constant composition method." Journal of Materials Science: Materials in Medicine 7.4 (1996): 201-205 (Year: 1996).

* cited by examiner

ORTHOPEDIC IMPLANT HAVING A CRYSTALLINE GALLIUM-CONTAINING HYDROXYAPATITE COATING AND METHODS FOR MAKING THE SAME This application is a continuation of U.S. patent application Ser. No. 16/725,444, now U.S. Pat. No. 11,141,505, filed Dec. 23, 2019, which is a divisional application of U.S. patent application Ser. No. 15/472,186, now U.S. Pat. No. 10,537,658, filed Mar. 28, 2017, the entire disclosures of which are hereby incorporated by reference.

CROSS-REFERENCE TO RELATED APPLICATIONS

Cross reference is made to U.S. patent application Ser. No. 15/472,189, now U.S. Pat. No. 10,537,661, filed Mar. 28, 2017, which is entitled "ORTHOPEDIC IMPLANT HAVING A CRYSTALLINE CALCIUM PHOSPHATE COATING AND METHODS FOR MAKING THE SAME," which is hereby incorporated by reference.

FIELD OF THE INVENTION

The present invention relates generally to a gallium-containing hydroxyapatite coating, and more particularly to an orthopedic implant having a solution deposited gallium-substituted hydroxyapatite coating and methods for making the same.

BACKGROUND OF THE INVENTION

Bone repair often involves the use of orthopedic implants to replace missing bone or support bone during the healing process. It is typically desirable to coat such orthopedic implants with osteoconductive materials to encourage bone growth or biological fixation.

Hydroxyapatite (HA) is a naturally occurring mineral found in bones and teeth. Studies have shown that HA is osteoconductive, and orthopedic implants have been coated with HA for this reason. Various processes for coating implants with HA are known. One process used for coating implants is plasma spray. In this process, HA powder is fed into a high temperature torch with a carrier gas. The HA powder is partially melted and then impacts the substrate at high velocity whereupon it is rapidly quenched back to room temperature. This process produces a mixture of HA, other calcium phosphate phases, and amorphous calcium phosphate. These phases have wide differences in solubility in vivo. As a result, plasma sprayed hydroxyapatite (PSHA) films do not uniformly dissolve or degrade in vivo. This non-homogenous degradation can generate particulates in the vicinity of the implant which can result in an inflammatory cascade leading to osteolysis. The particles may also find their way into joint articular surfaces, resulting in increased wear. Finally, the process is not well suited for coating porous structures of cementless implants because it is a "line of sight" process. PSHA processing or post processing methods can be applied that result in highly crystalline coatings with long resorption times in-vivo. This attribute gives rise to concerns over long term delamination of these relatively thick stable coatings.

Other methods to produce HA coatings for biological fixation include physical methods such as sputtering, evaporation, and chemical vapor deposition. These physical methods do not reproduce the nano-crystallinity and high surface area of biological apatites, and the resulting coatings may not uniformly dissolve and may release particulates.

Solution (or suspension) methods for producing HA coatings have also been attempted. For example, Zitelli, Joseph P. and Higham, Paul (2000), A Novel Method For Solution Deposition of Hydroxyapatite Onto Three Dimensionally Porous Metallic Surfaces: Peri-Apatite HA describes a process that involves producing a slurry of finely divided HA particles into which implants are placed and coated by accretion of the slurry particles. High surface area, microcrystalline coatings are produced, but their adhesion to the substrate is poor.

Electrochemically assisted solution deposition has also been developed. In this process, a voltage exceeding that necessary to hydrolyze water is applied to an implant while the implant is suspended in an aqueous solution. This process results in deposition of calcium phosphate material on the implant. Typically, the deposited film is a mixture of calcium phosphate (CaP) phases and requires post processing to convert the films to phase pure HA. Poor adhesion is also a concern with these films. Finally, control of electrochemical currents on porous implants with irregular particles is challenging, making this process difficult to scale.

Biomimetic processes have also been developed. These processes employ solutions mimicking body fluid concentrations and are typically performed near body temperature. These processes can yield bone-like apatite but require days or weeks to produce films a few microns thick. Attempts to increase rates associated with such methods have led to complications in reproducibly controlling pH, deposition rate, and accretion rate compared to crystalline growth on the surface of the implant. Films formed at higher rates have been found to contain amorphous material. Uncontrolled deposition rate also makes it difficult to achieve target coating weights or thicknesses.

There have been previous attempts to add gallium (Ga) to apatite coatings. However, prior methods have been unsuccessful at doping Ga ions into the hydroxyapatite lattice such that specific calcium sites undergo substitution.

As described above, hydroxyapatite coatings may be applied to orthopedic implants to enhance osteoconductivity using methods that are either rapid but lead to coatings having certain undesirable or unpredictable properties or lead to more desirable products but can take days to form. What is needed is a conformal calcium phosphate coating that can be rapidly formed and has a microstructure that lends itself to uniform degradation over a period of several weeks without generating particulates.

SUMMARY OF THE DISCLOSURE

Several embodiments of the invention are described by the following enumerated clauses:

1. An orthopedic implant comprising a metal surface and a hydroxyapatite layer disposed on at least part of the metal surface, the hydroxyapatite layer comprising gallium ions therein, wherein the hydroxyapatite layer is crystalline.

2. An orthopedic implant comprising a metal surface and a hydroxyapatite layer disposed on at least part of the metal surface, the hydroxyapatite layer comprising gallium ions therein, wherein the hydroxyapatite layer has an average crystallite size of less than about 75 nm in the [001] direction.

3. An orthopedic implant comprising a metal surface and a hydroxyapatite layer disposed on at least part of the metal surface, the hydroxyapatite layer comprising gallium ions therein, wherein the hydroxyapatite layer, when subjected to XRD, produces a (002) XRD peak and a (112) XRD peak, and the (002) XRD peak has an intensity 1.5 to 10 times greater than the (112) XRD peak.

4. An orthopedic implant comprising a metal surface and a hydroxyapatite layer disposed on at least part of the metal surface, the hydroxyapatite layer comprising gallium ions therein, wherein the hydroxyapatite layer continuously dissolves for more than 2 hours in vitro.

5. An orthopedic implant comprising a metal surface and a hydroxyapatite layer disposed on at least part of the metal surface, the hydroxyapatite layer comprising gallium ions therein, wherein the hydroxyapatite layer is substantially free of carbonate as measured by infrared spectroscopy.

6. The orthopedic implant of any one of the preceding clauses, wherein the gallium ions are substituted into the crystal lattice of the hydroxyapatite layer.

7. The orthopedic implant of any one of the preceding clauses, wherein the hydroxyapatite layer, when subjected to XRD, produces a (002) XRD peak that is shifted by about 0.001° 2θ to about 0.1° 2θ compared to the (002) XRD peak of crystalline hydroxyapatite without gallium.

8. The orthopedic implant of any one of the preceding clauses, wherein the hydroxyapatite layer, when subjected to XRD, produces a (002) XRD peak that corresponds to a d-spacing shift of about 0.001 Å to about 0.05 Å compared to the (002) XRD peak of crystalline hydroxyapatite without gallium.

9. The orthopedic implant of any one of the preceding clauses, wherein the gallium ions comprise about 0.01 wt % to about 5 wt % of the hydroxyapatite layer.

10. The orthopedic implant of any one of the preceding clauses, wherein the hydroxyapatite layer has an average crystallite size of less than about 75 nm in the direction.

11. The orthopedic implant of any one of the preceding clauses, wherein the hydroxyapatite layer has an average crystallite size of about 10 to about 75 nm in the direction.

12. The orthopedic implant of any one of the preceding clauses, wherein the hydroxyapatite layer has an average crystallite size of about 20 nm to about 70 nm in the [001] direction.

13. The orthopedic implant of any one of the preceding clauses, wherein the hydroxyapatite layer, when subjected to XRD, produces a (002) XRD peak and a (112) XRD peak, and the (002) XRD peak has an intensity 1.5 to 10 times greater than the (112) XRD peak.

14. The orthopedic implant of any one of the preceding clauses, wherein the hydroxyapatite layer, when subjected to XRD, produces a (002) XRD peak and a (112) XRD peak, and the (002) XRD peak has an intensity 2 to 5 times greater than the (112) XRD peak.

15. The orthopedic implant of any one of the preceding clauses, wherein the hydroxyapatite layer dissolves for more than 2 hours in vitro.

16. The orthopedic implant of any one of the preceding clauses, wherein the hydroxyapatite layer dissolves for more than 5 hours in vitro.

17. The orthopedic implant of any one of the preceding clauses, wherein the hydroxyapatite layer dissolves for more than 24 hours in vitro.

18. The orthopedic implant of any one of the preceding clauses, wherein the hydroxyapatite layer is resorbed in vivo within 6 weeks.

19. The orthopedic implant of any one of the preceding clauses, wherein the hydroxyapatite layer comprises about 0 wt % to about 5 wt % carbonate.

20. The orthopedic implant of any one of the preceding clauses, wherein the hydroxyapatite layer is substantially free of carbonate as measured by infrared spectroscopy.

21. The orthopedic implant of any one of the preceding clauses, wherein the hydroxyapatite layer is in contact with the metal surface.

22. The orthopedic implant of any one of the preceding clauses, wherein the metal surface comprises a metal oxide.

23. The orthopedic implant of any one of the preceding clauses, wherein the metal surface comprises titanium.

24. The orthopedic implant of any one of the preceding clauses, wherein the metal surface comprises a cobalt chromium alloy.

25. The orthopedic implant of any one of the preceding clauses, wherein the metal surface comprises a titanium oxide.

26. The orthopedic implant of any one of the preceding clauses, wherein the metal surface comprises a titanate.

27. The orthopedic implant of any one of the preceding clauses, wherein the metal surface comprises sodium titanate.

28. The orthopedic implant of any one of the preceding clauses, wherein the metal surface is a porous metal oxide surface.

29. The orthopedic implant of any one of the preceding clauses, wherein the metal surface is a titanium surface that has been treated with hydroxide.

30. The orthopedic implant of clause 29, wherein the hydroxide has a concentration of 1M or greater.

31. The orthopedic implant of clause 29 or 30, wherein the hydroxide has a concentration of 2M or greater.

32. The orthopedic implant of any one of clauses 29 to 31, wherein the hydroxide is sodium hydroxide.

33. The orthopedic implant of any one of clauses 29 to 32, wherein the hydroxide is potassium hydroxide.

34. The orthopedic implant of any one of clauses 29 to 33, wherein the titanium surface is not heat treated after being treated with the hydroxide.

35. The orthopedic implant of any one of the preceding clauses, wherein the metal surface has a thickness greater than about 50 nm.

36. The orthopedic implant of any one of the preceding clauses, wherein the metal surface has a thickness between about 50 nm and about 1 µm.

37. The orthopedic implant of any one of the preceding clauses, wherein the metal surface has a thickness between about 50 nm and about 100 nm.

38. The orthopedic implant of any one of the preceding clauses, wherein the hydroxyapatite layer has a crystallinity of greater than about 90%.

39. The orthopedic implant of any one of the preceding clauses, wherein the hydroxyapatite layer has a crystallinity of about 70 wt % to about 100 wt %.

40. The orthopedic implant of any one of the preceding clauses, wherein the hydroxyapatite layer has a phase purity of crystalline hydroxyapatite of greater than 90%.

41. The orthopedic implant of any one of the preceding clauses, wherein the hydroxyapatite layer has a shear strength of about 20 MPa to about 80 MPa as determined according to ASTM F1044.

42. The orthopedic implant of any one of the preceding clauses, wherein the hydroxyapatite layer has a tensile strength of about 50 MPa to about 100 MPa as determined according to ASTM F1147.

43. The orthopedic implant of any one of the preceding clauses, wherein the hydroxyapatite layer, in the absence of colorants, is transparent or translucent.

44. The orthopedic implant of any one of the preceding clauses, wherein the hydroxyapatite layer has a Ca/P ratio of 1 to 2.

45. The orthopedic implant of any one of the preceding clauses, wherein the hydroxyapatite layer has a surface area of about 15 m²/g to about 200 m²/g.

46. The orthopedic implant of any one of the preceding clauses, wherein the hydroxyapatite layer does not release particulates under physiological conditions.

47. The orthopedic implant of any one of the preceding clauses, wherein the hydroxyapatite layer is a calcium-deficient hydroxyapatite layer.

48. The orthopedic implant of any one of the preceding clauses, wherein gallium is distributed throughout the hydroxyapatite layer.

49. A method of treating a patient comprising administering to the patient the orthopedic implant of any one of the preceding clauses.

Additionally, several embodiments of the invention are described by the following enumerated clauses:

1. An osteoconductive composition comprising hydroxyapatite, the hydroxyapatite comprising gallium ions therein, wherein the hydroxyapatite is crystalline.

2. An osteoconductive composition comprising hydroxyapatite, the hydroxyapatite comprising gallium ions therein, wherein the hydroxyapatite has an average crystallite size of less than about 75 nm in the [001] direction.

3. An osteoconductive composition comprising hydroxyapatite, the hydroxyapatite comprising gallium ions therein, wherein the hydroxyapatite, when subjected to XRD, produces a (002) XRD peak and a (112) XRD peak, and the (002) XRD peak has an intensity 1.5 to 10 times greater than the (112) XRD peak.

4. An osteoconductive composition comprising hydroxyapatite, the hydroxyapatite comprising gallium ions therein, wherein the hydroxyapatite continuously dissolves for more than 2 hours in vitro.

5. An osteoconductive composition comprising hydroxyapatite, the hydroxyapatite comprising gallium ions therein, wherein the hydroxyapatite is substantially free of carbonate as measured by infrared spectroscopy.

6. The osteoconductive composition of any one of the preceding clauses, wherein the gallium ions are substituted into the crystal lattice of the hydroxyapatite.

7. The osteoconductive composition of any one of the preceding clauses, wherein the hydroxyapatite, when subjected to XRD, produces a (002) XRD peak that is shifted by about 0.001° 2θ to about 0.1° 2θ compared to the (002) XRD peak of crystalline hydroxyapatite without gallium.

8. The osteoconductive composition of any one of the preceding clauses, wherein the hydroxyapatite, when subjected to XRD, produces a (002) XRD peak that corresponds to a d-spacing shift of about 0.001 Å to about 0.05 Å compared to the (002) XRD peak of crystalline hydroxyapatite without gallium.

9. The osteoconductive composition of any one of the preceding clauses, wherein the gallium ions comprise about 0.01 wt % to about 5 wt % of the hydroxyapatite.

10. The osteoconductive composition of any one of the preceding clauses, wherein the hydroxyapatite has an average crystallite size of less than about 75 nm in the direction.

11. The osteoconductive composition of any one of the preceding clauses, wherein the hydroxyapatite has an average crystallite size of about 10 to about 75 nm in the [001] direction.

12. The osteoconductive composition of any one of the preceding clauses, wherein the hydroxyapatite has an average crystallite size of about 20 nm to about 70 nm in the [001] direction.

13. The osteoconductive composition of any one of the preceding clauses, wherein the hydroxyapatite, when subjected to XRD, produces a (002) XRD peak and a (112) XRD peak, and the (002) XRD peak has an intensity 1.5 to 10 times greater than the (112) XRD peak.

14. The osteoconductive composition of any one of the preceding clauses, wherein the hydroxyapatite, when subjected to XRD, produces a (002) XRD peak and a (112) XRD peak, and the (002) XRD peak has an intensity 2 to 5 times greater than the (112) XRD peak.

15. The osteoconductive composition of any one of the preceding clauses, wherein the hydroxyapatite dissolves for more than 2 hours in vitro.

16. The osteoconductive composition of any one of the preceding clauses, wherein the hydroxyapatite dissolves for more than 5 hours in vitro.

17. The osteoconductive composition of any one of the preceding clauses, wherein the hydroxyapatite dissolves for more than 24 hours in vitro.

18. The osteoconductive composition of any one of the preceding clauses, wherein the hydroxyapatite is resorbed in vivo within 6 weeks.

19. The osteoconductive composition of any one of the preceding clauses, wherein the hydroxyapatite comprises about 0 wt % to about 5 wt % carbonate.

20. The osteoconductive composition of any one of the preceding clauses, wherein the hydroxyapatite is substantially free of carbonate as measured by infrared spectroscopy.

21. The osteoconductive composition of any one of the preceding clauses, wherein the hydroxyapatite is in contact with a metal surface.

22. The osteoconductive composition of clause 21, wherein the metal surface comprises a metal oxide.

23. The osteoconductive composition of clause 21 or 22, wherein the metal surface comprises titanium.

24. The osteoconductive composition of clause 21 or 23, wherein the metal surface comprises a cobalt chromium alloy.

25. The osteoconductive composition of any one of clauses 21 to 24, wherein the metal surface comprises a titanium oxide.

26. The osteoconductive composition of any one of clauses 21 to 25, wherein the metal surface comprises a titanate.

27. The osteoconductive composition of any one of clauses 21 to 26, wherein the metal surface comprises sodium titanate.

28. The osteoconductive composition of any one of clauses 21 to 27, wherein the metal surface is a porous metal oxide surface.

29. The osteoconductive composition of any one of clauses 21 to 28, wherein the metal surface is a titanium surface that has been treated with hydroxide.

30. The osteoconductive composition of clause 29, wherein the hydroxide has a concentration of 1M or greater.

31. The osteoconductive composition of clause 29 or 30, wherein the hydroxide has a concentration of 2M or greater.

32. The osteoconductive composition of any one of clauses 29 to 31, wherein the hydroxide is sodium hydroxide.

33. The osteoconductive composition of any one of clauses 29 to 32, wherein the hydroxide is potassium hydroxide.

34. The osteoconductive composition of any one of clauses 29 to 33, wherein the titanium surface is not heat treated after being treated with the hydroxide.

35. The osteoconductive composition of any one of clauses 29 to 34, wherein the metal surface has a thickness greater than about 50 nm.

36. The osteoconductive composition of any one of clauses 29 to 35, wherein the metal surface has a thickness between about 50 nm and about 1 μm.

37. The osteoconductive composition of any one of clauses 29 to 36, wherein the metal surface has a thickness between about 50 nm and about 100 nm.

38. The osteoconductive composition of any one of the preceding clauses, wherein the hydroxyapatite has a crystallinity of greater than about 90%.

39. The osteoconductive composition of any one of the preceding clauses, wherein the hydroxyapatite has a crystallinity of about 70 wt % to about 100 wt %.

40. The osteoconductive composition of any one of the preceding clauses, wherein the hydroxyapatite has a phase purity of crystalline hydroxyapatite of greater than 90%.

41. The osteoconductive composition of any one of the preceding clauses, wherein the hydroxyapatite has a shear strength of about 20 MPa to about 80 MPa as determined according to ASTM F1044.

42. The osteoconductive composition of any one of the preceding clauses, wherein the hydroxyapatite has a tensile strength of about 50 MPa to about 100 MPa as determined according to ASTM F1147.

43. The osteoconductive composition of any one of the preceding clauses, wherein the hydroxyapatite, in the absence of colorants, is transparent or translucent.

44. The osteoconductive composition of any one of the preceding clauses, wherein the hydroxyapatite has a Ca/P ratio of 1 to 2.

45. The osteoconductive composition of any one of the preceding clauses, wherein the hydroxyapatite has a surface area of about 15 m$^2$/g to about 200 m$^2$/g.

46. The osteoconductive composition of any one of the preceding clauses, wherein the hydroxyapatite does not release particulates under physiological conditions.

47. The osteoconductive composition of any one of the preceding clauses, wherein the hydroxyapatite is calcium-deficient hydroxyapatite.

48. The osteoconductive composition of any one of the preceding clauses, wherein gallium is distributed throughout the hydroxyapatite.

Additionally, several embodiments of the invention are described by the following enumerated clauses:

1. A method of forming a hydroxyapatite coating, the method comprising contacting a metal surface with a supersaturated solution comprising calcium ions, phosphate ions, and gallium ions and reducing the amount of air in contact with the supersaturated solution during the coating step.

2. A method of forming a hydroxyapatite coating, the method comprising contacting a metal surface with a supersaturated solution comprising calcium ions, phosphate ions, and gallium ions wherein the pH of the solution varies by less than 0.1 pH unit/hour during the contacting step.

3. A method of forming a hydroxyapatite coating, the method comprising contacting a metal surface with a supersaturated solution comprising calcium ions, phosphate ions, and gallium ions wherein hydroxyapatite forms on the metal surface at a rate of 0.05 μm/h to 1.5 μm/h.

4. A method of forming a hydroxyapatite coating, the method comprising mixing a first solution comprising gallium ions and phosphate ions and a second solution comprising calcium ions to form a supersaturated solution and contacting a metal surface with the supersaturated solution.

5. The method of any one of the preceding clauses, wherein the metal surface is a metal oxide surface.

6. The method of any one of the preceding clauses, wherein the hydroxyapatite coating is formed on an orthopedic implant comprising the metal surface.

7. The method of any one of the preceding clauses, further comprising reducing the amount of air in contact with the supersaturated solution during the coating step.

8. The method of any one of the preceding clauses, wherein the pH of the supersaturated solution varies by less than 0.1 pH unit/hour during the contacting step.

9. The method of any one of the preceding clauses, further comprising allowing the pH to decrease during the contacting step by a predetermined value that is less than 0.15 pH units.

10. The method of any one of the preceding clauses, wherein hydroxyapatite forms on the metal surface at a rate of 0.05 μm/h to 1 μm/h.

11. The method of any one of the preceding clauses, wherein the hydroxyapatite coating is a calcium-deficient hydroxyapatite coating.

12. The method of any one of the preceding clauses, wherein the pH of the supersaturated solution is from about 7.5 to about 7.9.

13. The method of any one of the preceding clauses, wherein the concentration of calcium in the supersaturated solution is from about 1.4 mM to about 1.8 mM.

14. The method of any one of the preceding clauses, wherein the concentration of phosphate in the supersaturated solution is from about 2 mM to about 2.3 mM.

15. The method of any one of the preceding clauses, wherein the concentration of gallium in the supersaturated solution is from about 0.01 mM to about 1.0 mM.

16. The method of any one of the preceding clauses, wherein the Gibbs free energy change associated with forming the hydroxyapatite coating is from about 8 kJ/mol to about 8.4 kJ/mol when the contacting step begins.

17. The method of any one of the preceding clauses, wherein the coating forms at a rate per unit surface area from about 0.015 mg/hr·mm$^2$ to 0.05 about mg/hr·mm$^2$.

18. The method of any one of the preceding clauses, further comprising removing the metal surface from the supersaturated solution after from about 0.5 hour to about 12 hours.

19. The method of clause 18, further comprising contacting the metal surface, after the removing step, with an additional amount of the supersaturated solution that has not contacted the metal surface.

20. The method of any one of the preceding clauses, wherein the temperature of the supersaturated solution is from about 45° C. to about 50° C.

21. The method of any one of the preceding clauses, wherein the temperature of the supersaturated solution is from about 46.5° C. to 47.5° C.

22. The method of any one of the preceding clauses, wherein the supersaturated solution further comprises a salt and a buffer.

23. The method of clause 22, wherein the salt is sodium chloride and the buffer is tris(hydroxymethyl)aminomethane.

24. The method of any one of the preceding clauses, further comprising agitating the supersaturated solution during the contacting step.

25. The method of any one of the preceding clauses, wherein heterogeneous crystal growth occurs on the metal surface and homogeneous crystal growth does not occur.

26. The method of any one of the preceding clauses, further comprising forming a titanium layer on an implant body to form the metal surface.

27. The method of any one of the preceding clauses, further comprising activating the metal surface by contacting the metal surface with a base.

28. The method of clause 27, wherein the base is a hydroxide anion.

29. The method of any one of the preceding clauses, wherein the metal surface is a titanium dioxide surface.

30. The method of any one of the preceding clauses, wherein the metal surface is an activated metal surface.

31. The method of any one of the preceding clauses, wherein the metal surface comprises a titanate.

32. The method any one of the preceding clauses, wherein the process occurs under inert atmospheric conditions.

33. The method of any one of the preceding clauses, wherein the process occurs under an argon atmosphere.

34. The method of any one of the preceding clauses, wherein a first solution comprising gallium ions and phosphate ions and a second solution comprising calcium ions are mixed at from about 15° C. to about 35° C.

35. The method of any one of the preceding clauses, wherein the hydroxyapatite coating is not further treated to increase crystallinity after the contacting step.

36. The method of any one of the preceding clauses, wherein the method is validated for the amount of the calcium phosphate coating on the metal surface.

37. The method of any one of the preceding clauses, wherein the hydroxyapatite coating is formed predominantly through heterogeneous nucleation such that the supersaturated solution remains visibly free of turbidity during the contacting step.

38. The method of any one of the preceding clauses, wherein the hydroxyapatite coating forms at a substantially continuous rate throughout the contacting step.

39. The method of any one of the preceding clauses, further comprising determining the amount of the hydroxyapatite coating based on the amounts of the calcium ions and the phosphate ions.

40. The method of any one of the preceding clauses, wherein at least two deposition sequences are employed.

41. The method of any one of the preceding clauses, further comprising determining the amount of the hydroxyapatite coating based on the pH of the supersatured solution.

42. The method of any one of the preceding clauses, further comprising determining the amount of the hydroxyapatite coating based on the duration of the contacting step.

43. The method of any one of the preceding clauses, wherein the pH of the supersaturated solution varies by from about 0.01 to about 0.1 pH unit/hour during the contacting step.

44. The method of any one of the preceding clauses, wherein the coating forms at a rate per unit surface area from about 0.005 mg/hr·mm$^2$ to 0.015 about mg/hr·mm$^2$.

45. The method of any one of the preceding clauses, wherein the initial pH of the supersaturated solution is from about 7.5 to about 7.9, and the temperature of the supersaturated solution is from about 38° C. to about 60° C.

46. The method of any one of the preceding clauses, further comprising heating the coating in a phosphate solution to mitigate surface cracking.

47. The method of any one of the preceding clauses, further comprising contacting the coating with a supercritical fluid to mitigate surface cracking.

48. An osteoconductive composition formed according to the method of any one of the preceding clauses.

49. An orthopedic implant comprising an osteoconductive composition formed according to the method of any one of the preceding clauses.

The above and other objects, features, and advantages of the present invention will become apparent from the following description and the attached drawings.

DETAILED DESCRIPTION OF THE ILLUSTRATIVE EMBODIMENTS

Figure 1:
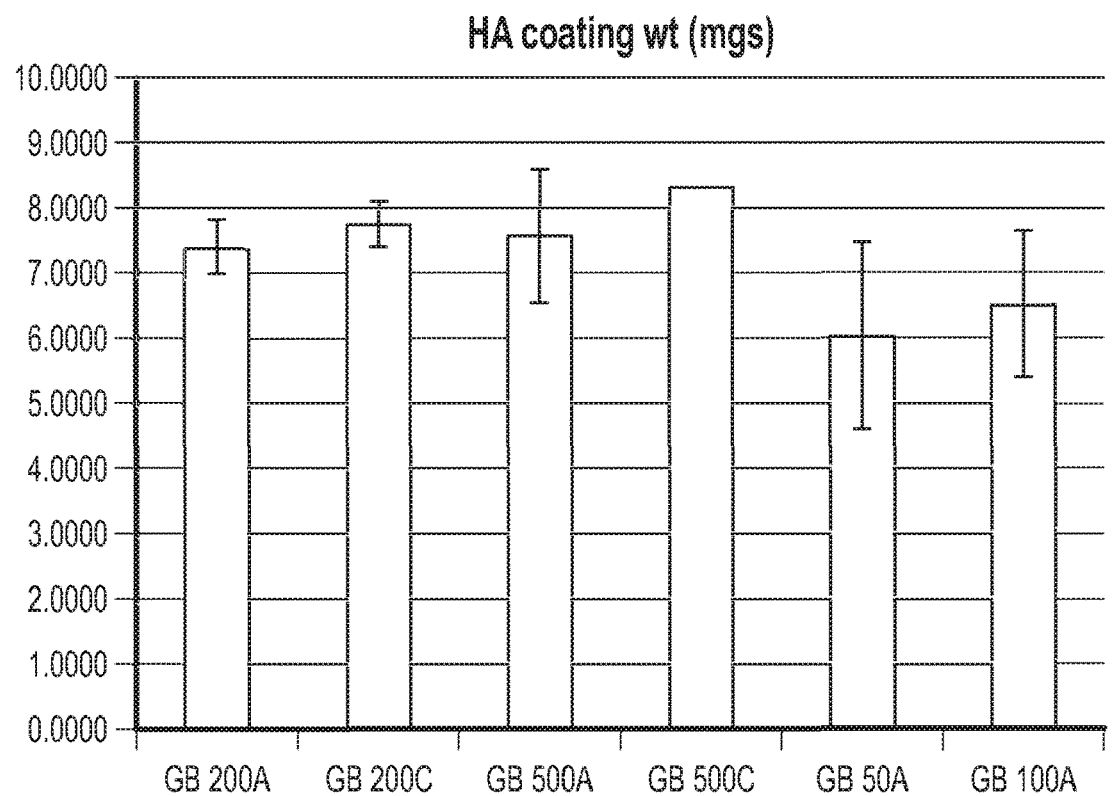
FIG. 1 is a chart showing the weights of hydroxyapatite coatings formed on crystalline and amorphous 50 nm- to 500 nm-thick titanium dioxide ($TiO_2$) coated substrates.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

The present invention relates to calcium phosphate coated orthopedic implants, such as gallium-substituted hydroxyapatite (HA) coated orthopedic implants, and methods of making the same. Without intending to be bound by theory, the presence of gallium in the coatings is believed to allow for enhanced biocompatibility compared to traditional hydroxyapatite coatings. In the present invention, gallium ions ($Ga^{+3}$) are incorporated or doped into an hydroxyapatite (HA) lattice, thus allowing for the localized controlled release of this therapeutic ion as the HA coating resorbs over several weeks in vivo. Gallium may accumulate in newly formed bone, aid in new bone formation, down-regulate inflammation as well as possess anti-bacterial activity. The gallium-substituted HA coatings described herein may be used in multifunctional coatings for enhancing osteogenic potential at the site of implantation and promoting anti-bacterial efficacy.

The gallium-substituted hydroxyapatite coatings described herein have a highly uniform microstructure. When the implants are used in a human or animal, the gallium-substituted hydroxyapatite coating degrades uniformly over an extended period of time without releasing particulates. In some embodiments, this is a period of 6 weeks or less. The coatings described herein also have advantageous adhesion and/or cohesion properties such as increased tensile strength compared to prior coatings. Additionally, the gallium-substituted hydroxyapatite coatings described herein can be rapidly formed on a substrate by a controlled, but rapid, growth process that lends itself to process validation utilizing process diagnostics that allow determination of total coating weight on a batch of parts without having to measure coating weights on parts resulting in the coatings' uniform microstructures and chemical compositions.

Solution deposited ceramic coatings may be predisposed to cracking during drying. As coating thickness is increased this effect may be exacerbated. In some instances, cracking may be observed for solution deposited gallium-substituted SoDHA (SoDHA-G) coatings as they are dried after being formed. Without intending to be bound by theory, compared to SoDHA coatings without gallium, SoDHA-G coatings exhibit a greater propensity for cracking and this could potentially be a result of lattice strain that accompanys doping gallium into the hydroxyapatite lattice. Two exemplary, independent methods to mitigate drying cracks that are described herein include: (1) organic solvent exchange and supercritical solvent extraction, and (2) re-precipitation crack healing via hydrothermal treatment. It is to be understood that organic solvent exchange and re-precipitation crack healing may be performed independent of each other or in combination.

The compositions and methods described herein may improve cementless fixation of orthopedic implants for improved survivorship and expand use of cementless implants to procedures where cemented implants are the current standard of care. One skilled in the art understands that this may allow for reduced operating room time and decreased costs for health care.

Gallium-Substituted Hydroxyapatite Coating

The calcium phosphate coatings described herein comprise gallium-substituted HA. As used herein, HA includes but is not limited to calcium deficient hydroxyapatite (CDHA) where calcium ions have been substituted by gallium. In some embodiments, the HA described herein is non-stoichiometric, gallium substituted HA. The gallium-substituted HA may be of the formula $Ca_{10-x}Ga_x(PO_4)_6(OH)_{2-x}(CO_3)_x$, wherein x is from about 0 to about 1 or about 0.1 to about 1. It is to be understood that the formulas described herein describe stoichiometric equivalents. The HA coatings have characteristic molar ratios of calcium to phosphate (Ca/P ratio). The Ca/P ratio may be from about 1 to about 2, about 1.2 to about 2, about 1.3 to about 2, about 1.39 to about 2, about 1 to about 1.8, about 1.2 to about 1.8, about 1.3 to about 1.8, about 1.39 to about 1.8, about 1 to about 1.7, about 1.2 to about 1.7, about 1.3 to about 1.7, about 1.39 to about 1.7, about 1 to about 1.649, about 1.2 to about 1.649, about 1.3 to about 1.649, about 1.39 to about 1.649, or about 1.5 to about 1.67. It is to be understood that the gallium-substituted HA may be modified by adjusting calcium and phosphate concentrations in the solutions from which the HA coatings may be formed.

In the gallium-substituted HA coatings, some of the calcium ions are substituted by gallium ions, compared to traditional HA. The bioactive gallium-substituted hydroxyapatite coating produced herein desirably contains a molar ratio of gallium ions to calcium ions of about 1:10 to about 1:5000, about 1:10 to about 1:1500, or about 1:20 to about 1:1500. Accordingly, the Ca/P ratios can be altered as a function of Ga substitution into the hydroxyapatite lattice.

As further described below, the gallium-substituted HA coatings are formable from supersaturated solutions that remain substantially free of turbidity, due to homogenous nucleation in solution, throughout the coating process. In some embodiments, the gallium-substituted HA coatings lack carbonate, which assists with pH control during coating formation. Without intending to be bound by theory, deposition from solutions substantially free of turbidity due to homogenous nucleation is believed to play a role in gallium-substituted HA coatings deposited with predictable coating rates and gallium-substituted HA having high crystallinity, uniform microstructure, and enhanced biocompatibility. In some embodiments, the wt. % carbonate in the coatings is about 0% to about 25%, about 0% to about 20%, about 0% to about 15%, about 0% to about 10%, about 0% to about 5%, about 0% to about 3%, about 0% to about 2%, about 0% to about 1%, about 0% to about 0.1%, about 0.1% to about 25%, about 0.1% to about 20%, about 0.1% to about 15%, about 0.1% to about 10%, about 0.1% to about 5%, about 0.1% to about 3%, about 0.1% to about 2%, about 0.1% to about 1%, about 1% to about 25%, about 1% to about 20%, about 1% to about 15%, about 1% to about 10%, about 1% to about 5%, about 1% to about 3%, about 1% to about 2%, about 2% to about 25%, about 2% to about 20%, about 2% to about 15%, about 2% to about 10%, about 2% to about 5%, or about 2% to about 3%. In some embodiments, the concentration of carbonate in the coatings is as measured by spectroscopic methods such as IR spectroscopy. The coatings may be substantially carbonate-free. As used herein, "substantially carbonate-free" coatings refers to coatings that do not have a distinguishable carbonate peak between 1500 cm$^{-1}$ and 1300 cm$^{-1}$ when subjected to IR spectroscopy.

The wt % of crystalline gallium-substituted HA in the coatings described herein is about 50% to about 100%, about 60% to about 100%, about 70% to about 100%, about 80% to about 100%, about 90% to about 100%, about 50% to about 99%, about 60% to about 99%, about 70% to about 99%, about 80% to about 99%, about 90% to about 99%, about 50% to about 95%, about 60% to about 95%, about 70% to about 95%, about 80% to about 95%, or about 90% to about 95%. Without intending to be bound by theory, it is believed that the coatings are formed by heterogeneous nucleation, resulting in coatings that primarily comprise crystalline gallium-substituted HA or OCP.

The gallium-substituted HA component of the gallium-substituted HA coatings has a high crystallinity as measured by, for example, differential scanning calorimetry (DSC). The crystallinity is greater than about 50%, greater than about 80%, greater than about 90%, greater than about 95%, greater than about 96%, greater than about 97%, about 80% to about 99.9%, about 90% to about 99.9%, about 95% to about 99.9%, about 96% to about 99.9%, or about 97% to about 99.9%.

The gallium-substituted HA component of the coatings has a high crystalline phase purity of its predominant phase. The crystalline phase purity is greater than about 80%, greater than about 90%, greater than about 95%, greater than about 96%, greater than about 97%, about 80% to about 99.9%, about 90% to about 99.9%, about 95% to about 99.9%, about 96% to about 99.9%, or about 97% to about 99.9%. The high crystallinity and high crystalline phase purity of the gallium-substituted HA component in the gallium-substituted HA coatings enhances biocompatibility and homogenous degradation in vivo while avoiding particulate release. In some embodiments, crystallinity is measured by differential scanning calorimetry (DSC).

The gallium-substituted HA component of the coatings has low or no amorphous content. The amorphous content is less than about 20%, less than about 15%, less than about 10%, less than about 5%, less than about 4%, less than about 3%, about 0.1% to about 3%, about 0.1% to about 5%, about 0.1% to about 10%, or about 0.1% to about 20%. The amorphous content may be too low to detect. In some embodiments, amorphous content is measured by differential scanning calorimetry (DSC).

The crystal structure of the gallium-substituted HA coatings can be characterized using X-ray spectroscopy, such as X-ray powder diffraction spectroscopy. The gallium-substituted HA coatings exhibit several characteristic 2θ diffraction angles when characterized by X-ray powder diffraction. The numbers shown in parenthesis are the Miller indices associated with each peak. The X-ray spectra of the gallium-substituted HA coatings may exhibit 2θ diffraction angles including about 26±2° (002), about 28±2° (102), about 32±2° (112), about 50±2° (213), and about 53±2° (004) or 26±0.5° (002), about 28±0.5° (102), about 32±0.5° (112), about 50±0.5° (213), and about 53±0.5° (004). The X-ray spectra of the gallium-substituted HA coatings may exhibit 2θ diffraction angles including about 26±1° (002), about 28±1° (102), about 32±1° (112), about 50±1° (213), and about 53±1° (004). The X-ray spectra of the gallium-substituted HA coatings may exhibit 2θ diffraction angles including about 25.58±0.1°, about 28.13±0.1°, about 31.75±0.1°, 32.17±0.1°, about 49±0.1°, and about 53±0.1°. It is to be understood that the diffraction angles recited herein may be systematically shifted due to variations in instrumentation.

The XRD spectra of the gallium-substituted HA coatings have characteristic relative intensities. As used herein, the relative intensity of a peak in an XRD spectrum refers to the intensity of a peak divided by the intensity of the most intense peak in the spectrum. The peaks associated with the (002), (211), (112), (202), (213), and (004) directions may have relative intensities of 100%, 40-50%, 45-55%, 15-25%, 10-20%, and 15-25%, respectively. Any one of the peaks associated with the (002), (211), (112), (202), (213), and (004) directions may have a relative intensity of 100%, 30-60%, 35-65%, 5-35%, 0-30%, and 5-35%, respectively. In some embodiments, the hydroxyapatite layer has a ratio of XRD intensity ratio of the (002) peak: the (211) peak that is greater than about 1, greater than about 1.25, greater than about 1.5, greater than about 1.75, greater than about 2.0, greater than about 2.5, greater than about 3.0, or greater than about 3.5.

As a result of gallium substitution, the 2θ diffraction angle of the (002) peak is shifted compared to a HA coating formed by the solution deposited process without gallium when the coatings are characterized using X-ray spectroscopy. The resulting shift of the (002) diffraction peak may be about up to about 0.25°, up to about 0.2°, up to about 0.15°, about 0.01° to about 0.25°, about 0.01° to about 0.2°, about 0.01° to about 0.15°, about 0.05° to about 0.25°, about 0.05° to about 0.2°, or about 0.05° to about 0.15°. The shift of the (002) diffraction peak may increase with increasing gallium ion concentration. The (002) diffraction peak 2θ shift is associated with a d-spacing shift ranging from about 0.001 Å to about 0.05 Å, about 0.0025 Å to about 0.025 Å, or about 0.0037 Å to about 0.0226 Å.

The gallium-substituted HA coatings can also be characterized using Fourier transform infrared (FTIR) spectroscopy. The gallium-substituted HA coatings exhibit FTIR bands at about 1100 cm$^{-1}$, characteristic of $PO_4^{3-}$. The gallium-substituted HA coatings lack FTIR bands characteristic for carbonate between about 1400 to 1500 cm$^{-1}$.

In some embodiments, the gallium-substituted HA coatings are nanocrystalline. Accordingly, gallium-substituted HA coatings of the instant disclosure result in small crystallites sizes as determined by X-ray diffraction or scanning electron microscopy. The gallium-substituted hydroxyapatite has an average crystallite size ranging from about 1 nm to about 100 nm, about 5 nm to about 100 nm, about 10 nm to about 100 nm, about 15 nm to about 100 nm, about 1 nm to about 80 nm, about 5 nm to about 80 nm, about 10 nm to about 80 nm, about 15 nm to about 80 nm, or about 15 nm to about 70 nm. The average crystallite size in the (002) direction is from about 60 nm to about 80 nm, about 65 nm to about 75 nm, about 66 nm to about 73 nm, or about 68 nm to about 69 nm. The average crystallite size in the (200) direction is from about 10 nm to about 30 nm, about 15 nm to about 25 nm, about 16 nm to about 23 nm, or about 18 nm to about 22 nm. The average crystallite size in the (210) direction is from about 40 nm to about 60 nm, about 45 nm to about 55 nm, about 46 nm to about 53 nm, or about 48 nm to about 52 nm. In some embodiments, the gallium-substituted HA films have a crystallite size in at least one direction that is less than the wavelength of light, and the grains are bonded to one another without the presence of a second amorphous or crystalline phase having a different refractive index. In such embodiments, the coatings are transparent or translucent.

Gallium-substituted HA coatings of the instant disclosure are highly porous and have high surface areas. The surface area is about 5 m$^2$/g to about 100 m$^2$/g, about 10 m$^2$/g to about 75 m$^2$/g, about 10 m$^2$/g to about 50 m$^2$/g, about 10 m$^2$/g to about 200 m$^2$/g, about 10 m$^2$/g to about 150 m$^2$/g, about 10 m$^2$/g to about 100 m$^2$/g, about 50 m$^2$/g to about 200 m$^2$/g, about 50 m$^2$/g to about 150 m$^2$/g, about 50 m$^2$/g to about 100 m$^2$/g, or about 15 m$^2$/g to about 35 m$^2$/g. The surface area may be determined using Brunauer-Emmett-Teller (BET) method. This surface area may lead to significant improvements in adsorption of therapeutic agents onto these coatings, as further discussed below. The increased loading capability may be utilized to tailor the dose and prolonged release of the therapeutic agents thereby increasing treatment efficacy.

Without intending to be bound by theory, another benefit of gallium-substituted HA crystallite size reduction may be in refining the surface nano-topography of implant surfaces thereby increasing adsorption of fibrinogen from blood after implantation. This subsequently increases platelet adhesion and activation, which is an initiator of the inflammatory cascade and healing process. Nano-topography has also shown to improve the adhesion strength of the fibrin clot (or extracellular matrix) to the implant surface thereby ensuring its integrity during new bone formation and wound contraction throughout the healing process.

The coatings described herein may release calcium and/or gallium at a substantially continuous rate or at a continuous rate over an extended period of time in vitro as measured by calcium electrodes as described in ASTM F1926. As used herein, a substantially continuous rate is a rate that changes by less than 20% each hour. As used herein, a continuous rate is a rate that changes by less than 5% each hour. The coatings may release calcium at a substantially continuous rate for at least about 5 hours, at least about 10 hours, at least about 15 hours, at least about 20 hours, about 5 hours to about 100 hours, about 5 hours to about 50 hours, about 5 hours to about 30 hours, about 5 hours to about 25 hours, about 10 hours to about 100 hours, about 10 hours to about 50 hours, about 10 hours to about 30 hours, about 10 hours to about 25 hours, about 15 hours to about 100 hours, about 15 hours to about 50 hours, about 15 hours to about 30 hours, or about 15 hours to about 25 hours. The coatings may release calcium at a continuous rate for at least about 5 hours, at least about 10 hours, at least about 15 hours, at least about 20 hours, about 5 hours to about 100 hours, about 5 hours to about 50 hours, about 5 hours to about 30 hours, about 5 hours to about 25 hours, about 10 hours to about 100 hours, about 10 hours to about 50 hours, about 10 hours to about 30 hours, about 10 hours to about 25 hours, about 15 hours to about 100 hours, about 15 hours to about 50 hours, about 15 hours to about 30 hours, or about 15 hours to about 25 hours.

The gallium-substituted HA coatings described herein may have high adhesion to a substrate and have high cohesion compared to previously described coatings. Adhesion and cohesion can be quantified by measuring tensile and shear peak stress values. The coatings described herein extend outward from a surface of an orthopedic implant. As used herein, shear stress is the stress component parallel to the bulk direction surface, and tensile stress is the stress component away from the bulk direction surface.

The shear peak stress of the gallium-substituted HA coatings, as determined according to ASTM F1044, may be about 10 MPa to about 150 MPa, about 10 MPa to about 100 MPa, about 10 MPa to about 75 MPa, about 10 MPa to about 65 MPa, or about 28.2 MPa to about 63.6 MPa. The tensile peak stress, as determined according to ASTM F1147, may be about 25 MPa to about 120 MPa, about 40 MPa to about 120 MPa, about 50 MPa to about 120 MPa, about 60 MPa to about 120 MPa, about 68 MPa to about 120 MPa, 25 MPa to about 100 MPa, about 40 MPa to about 100 MPa, about 50 MPa to about 100 MPa, about 60 MPa to about 100 MPa, about 68 MPa to about 100 MPa, 25 MPa to about 95 MPa, about 40 MPa to about 95 MPa, about 50 MPa to about 95 MPa, about 60 MPa to about 95 MPa, about 68 MPa to about 95 MPa, 25 MPa to about 90 MPa, about 40 MPa to about 90 MPa, about 50 MPa to about 90 MPa, about 60 MPa to about 90 MPa, or about 68 MPa to about 90 MPa.

The gallium-substituted HA coatings may have an average thickness, as measured from the surface of the orthopedic implant to which it adheres, of about 150 nm or more, about 1 μm to about 50 μm, about 1 μm to about 25 μm, about 1 μm to about 20 μm, about 1 μm to about 15 μm, about 1 μm to about 10 μm, about 1 μm to about 8 μm, about 3 μm to about 50 μm, about 3 μm to about 25 μm, about 3 μm to about 20 μm, about 3 μm to about 15 μm, about 3 μm to about 10 μm, about 3 μm to about 8 μm, about 5 μm to about 50 μm, about 5 μm to about 25 μm, about 5 μm to about 20 μm, about 5 μm to about 15 μm, about 5 μm to about 10 μm, about 5 μm to about 8 μm, or about 7 μm.

When applied to porous ingrowth surfaces like porocoat or gription, the gallium-substituted HA coatings may have a weight per unit surface area of about 1 to about 100 mg/cm$^2$, about 1 to about 75 mg/cm$^2$, about 1 to about 50 mg/cm$^2$, about 1 to about 25 mg/cm$^2$, about 1 to about 12 mg/cm$^2$, about 5 to about 100 mg/cm$^2$, about 5 to about 75 mg/cm$^2$, about 5 to about 50 mg/cm$^2$, about 5 to about 25 mg/cm$^2$, about 5 to about 12 mg/cm$^2$, about 7 to about 15 mg/cm$^2$, about 7 to about 14 mg/cm$^2$, about 7 to about 12 mg/cm$^2$, about 9 to about 15 mg/cm$^2$, about 9 to about 14 mg/cm$^2$, about 9 to about 12 mg/cm$^2$, about 9 to about 11 mg/cm$^2$, about 9 to about 12 mg/cm$^2$, or about 8 to about 12 mg/cm$^2$.

When an orthopedic implant coated with the gallium-substituted HA coatings described herein is used in a patient or animal (e.g. canine), the in vivo resorption rates are such that the gallium-substituted HA coating is resorbed within about 3 to about 15 weeks, about 4 to about 15 weeks, about 5 to about 15 weeks, about 6 to about 15 weeks, about 3 to about 14 weeks, about 4 to about 14 weeks, about 5 to about 14 weeks, about 6 to about 14 weeks, about 3 to about 12 weeks, about 4 to about 12 weeks, about 5 to about 12 weeks, about 6 to about 12 weeks, about 1 to about 6 weeks, or less than about 6 weeks.

In some embodiments, the gallium-substituted HA coating further comprises one or more additional therapeutic agents. The coating may be doped with an additional material for improved osteoconduction and/or delivery of anti-infective materials.

The therapeutic agent may include proteins, lipids, (lipo)polysaccharides, growth factors, cytostatic agents, hormones, antibiotics, anti-infective agents, anti-allergenic agents, anti-inflammatory agents, progestational agents, humoral agents, antipyretic agents, and nutritional agents. The therapeutic agent may be an osteoinductive substance, osteoconductive substance, or a substance that is both osteoinductive and osteoconductive.

Metal Surface

The calcium phosphate layers described herein are disposed about a surface of an orthopedic implant. The surface may be a metal surface, such as a titanium or CoCr alloy surface or a titanium dioxide (TiO$_2$) surface. In some embodiments, the outer surface of the metal layer is amorphous and the rest of the metal layer is crystalline. In other embodiments, the entire metal layer is crystalline. For example, the interface between the surface and the calcium phosphate coating may comprise an activated layer from which the calcium phosphate coating nucleates and grows outward. It is to be understood that the entire surface may be coated with HA or the surface may be masked such that a predetermined part of the surface is coated with HA.

The surface may be an activated metal surface. For example, when the metal surface is a titanium surface, the surface may be activated to form a titanate outer surface, which facilitates nucleation and increased adhesion between the titanium surface and the calcium phosphate coating. Activation of the titanium surface also facilitates controlled crystal growth of the calcium phosphate layer therefrom without further heat treatment, as will be further described below. In some embodiments, the native oxide or oxide produced by passivation processes, is converted to titanate by hydroxide treatment. In some embodiments, the titanate is sodium titanate. Alternatively, crystalline TiO$_2$ may be applied to the implant core. Such crystalline films induce nucleation without further treatment. In some embodiments, the implant surface is comprised of something other than titanium alloys. In this case, activation may be accomplished by deposition of nm scale films of crystalline TiOx on the implant surface. Alternatively, thin amorphous TiOx layers may be deposited and converted to titanate by hydroxide treatment of the amorphous film. Additional means of activation include creating surfaces that contain COOH, NH$_2$, or other charged moieties as will be apparent to those skilled in the art.

In some embodiments, the entire core of the implant is titanium. In other embodiments, titanium is coated on at least part of an implant core, which, in turn, is coated with a calcium phosphate coating described herein. The implant core and/or surface may comprise a material such as CoCrMo or PEEK.

Alternatively, the implant may comprise a suitable material, such as silicon based materials, ceramic based materials, or polymer based materials. Other contemplated materials include cobalt, chromium, iron, tantalum, niobium, zirconium, and alloys thereof (e.g., titanium alloys and tantalum alloys), as well as cobalt, cobalt-chromium alloys, and stainless steel. The implant may comprise biocompatible polymers, natural or synthetic polymers, such as polyethylene (e.g., ultrahigh molecular weight polyethylene or polyethylene oxide), polypropylene, polytetrafluoroethylene, polyglycolic acid, polylactic acid, other polysaccharides, and copolymers of any of the foregoing (e.g., copolymers of polylactic acid and polyglycol acid) including tissue engineering scaffolds composed of synthetic polymers (e.g. poly HEMA) and biological macromolecules (e.g. collagen and chondroitin sulfate).

The metal or metal oxide layer may have a thickness of at least about 25 nm, at least about 30 nm, at least about 35 nm, at least about 40 nm, at least about 45 nm, at least about 50 nm, at least about 60 nm, at least about 70 nm, at least about 80 nm, at least about 90 nm, or at least about 100 nm. In some embodiments, the layer may have a thickness of about 25 nm to about 125 nm, about 30 nm to about 125 nm, about 35 nm to about 125 nm, about 40 nm to about 125 nm, about 45 nm to about 125 nm, about 50 nm to about 125 nm, about 25 nm to about 100 nm, about 30 nm to about 100 nm, about 35 nm to about 100 nm, about 40 nm to about 100 nm, about 45 nm to about 100 nm, or about 50 nm to about 100 nm. Films under 100 nm may cease to display interference colors after hydroxide processing. The preferred thickness of the layer may be determined based on the desired color profile of the orthopedic implant.

The crystal structure of the titanium surface can be characterized using X-ray spectroscopy, such as X-ray powder diffraction. The titanium surfaces exhibit several characteristic 2θ diffraction angles when characterized by X-ray powder diffraction. The X-ray spectra of titanium films exhibit 2θ diffraction angles at about 26°, about 28°, about 32°, about 49°, and about 53°.

The metal surface may be modified prior to being coated with the HA coating. For example, the metal surface may be modified with respect to surface roughness in order to facilitate the adherence of the apatite coating to the biocompatible substrate. Possible methods of modifying the roughness of the metal surface include acid etching or grit blasting.

Titanium Oxide Formation and Activation

As discussed above, a titanium oxide layer may be formed on an orthopedic prosthetic surface. Preferable processes for TiO$_2$ layer formation are conformal (non-line of sight) and produce films that strongly adhere to a core. Atomic layer deposition has been shown to be capable of producing both amorphous and crystalline films that are well adhered and of uniform thickness. Sol-gel processes and electrodeposition of TiO$_2$ films also may be utilized.

After the surface is formed or otherwise available, surface activation may be performed to encourage nucleation and growth of calcium phosphate. Basic conditions may be applied to the titanium oxide surface to activate it. In some embodiments, the titanium surface is treated with a hydroxide source, such as sodium hydroxide. Hydroxide treatment produces a porous titanate surface on the metal that facilitates nucleation and growth of calcium phosphate.

Gallium Substituted Solution Deposited Hydroxyapatite (SoDHA-G) Process

The gallium-substituted hydroxyapatite coatings described herein are formed on the activated surfaces by deposition from supersaturated solutions. At sufficiently optimized supersaturation values, stable nuclei form and grow from active surfaces, resulting in the calcium phosphate coatings described herein. Without intending to be bound by theory, it is believed that the growth predominantly occurs by a heterogeneous nucleation mechanism rather than a homogeneous mechanism under the conditions further described below. The process results in a gallium-substituted hydroxyapatite product, such as the coatings described above.

Calcium and phosphate/gallium solutions are prepared and adjusted to desired concentrations by dilution. The calcium and phosphate/gallium solutions are mixed together, resulting in a solution that is supersaturated with respect to hydroxyapatite. Orthopedic implant precursors, which have activated surfaces, are contacted with the supersaturated solution, resulting in gallium-substituted hydroxyapatite coating formation at a reproducible rate, under solution conditions that do not result in turbidity. In some embodiments, the substrate has a crystalline $TiO_2$ film surface, which is not necessarily activated. In some embodiments, the substrate has an amorphous film surface that has been treated with a base such as hydroxide. It is contemplated that implants may be masked to allow deposition only on selected portions of the implants.

Solution turbidity may be determined with the aid of optical sensors that evaluate the UV range. An Optek AS16F probe sensor operating at 430 nm was utilized to detect turbidity due to homogenous nucleation in solution. Without intending to be bound by theory, coating at controlled rates is believed to have occurred primarily by heterogeneous nucleation.

The degree of supersaturation in the coating solution depends on the activities of calcium, phosphate, and gallium ions in solution, and solution pH. Activities depend in turn on solution concentration, speciation, and ionic strength. The calcium and phosphate stock solutions are mixed together, resulting in a solution that is supersaturated with respect to the desired calcium phosphate product. Orthopedic implants, which have activated surfaces, are contacted with the supersaturated solution, resulting in gallium-substituted hydroxyapatite coating formation at a rapid, reproducible rate.

Implants are coated in a solution that is supersaturated with respect to HA phases. In some embodiments, the supersaturated solution comprises $Ga(NO_3)_3$, $Ca(NO_3)$, $K_2HPO_4$, $KH_2PO_4$, NaCl, and tris(hydroxymethyl)aminomethane (TRIS) buffer. The ratio of $HPO_4^{2-}/H_2PO_4^-$ may be selected to achieve the target solution pH. Other counterions besides $NO_3$ and K may be utilized as those skilled in the art will appreciate. Calcium and phosphate/gallium concentrates may be obtained with a certified concentration and then diluted to working concentrations prior to blending to create the final supersaturated solutions.

The solutions used in forming HA include calcium cations at a concentration of about 0.5 to about 1.5 mM, about 0.6 to about 1.5 mM, about 0.7 to about 1.5 mM, about 0.5 to about 1.3 mM, about 0.6 to about 1.3 mM, about 0.7 to about 1.3 mM, about 0.5 to about 1.1 mM, about 0.6 to about 1.1 mM, about 0.7 to about 1.1 mM, about 0.5 to about 1.05 mM, about 0.6 to about 1.05 mM, about 0.7 to about 1.05 mM, or about 0.62 to about 1.05 mM. In some embodiments the calcium ion is $Ca^{2+}$.

The solutions used in forming HA include phosphate anions at a concentration of about 0.75 mM to about 1.75 mM, about 1.0 mM to about 1.75 mM, about 1.25 mM to about 1.75 mM, about 0.75 mM to about 1.5 mM, about 1.0 mM to about 1.5 mM, about 1.25 mM to about 1.5 mM, about 0.75 mM to about 1.35 mM, about 1.0 mM to about 1.35 mM, about 1.25 mM to about 1.35 mM, about 0.75 mM to about 1.3 mM, about 1.0 mM to about 1.3 mM, or about 1.25 mM to about 1.3 mM. In some embodiments the phosphate ions are $PO_4^{3-}$, $HPO_4^{2-}$, $H_2PO_4^-$, or a combination thereof.

The phosphate solutions used in forming HA include gallium cations at a concentration of about 0.01 mM to about 0.4 mM, about 0.01 mM to about 0.3 mM, about 0.01 mM to about 0.2 mM, about 0.01 mM to about 0.1 mM, about 0.01 mM to about 0.4 mM, about 0.05 mM to about 0.3 mM, about 0.05 mM to about 0.2 mM, or about 0.05 mM to about 0.1 mM. In some embodiments the gallium ion is $Ga^{3+}$. In some embodiments, the source of gallium is $Ga(NO_3)_3$.

The solutions used in forming gallium-substituted HA have a pH of about 7.5 to about 8, about 7.55 to about 8, about 7.6 to about 8, about 7.65 to about 8, about 7.5 to about 7.9, about 7.55 to about 7.9, about 7.6 to about 7.9, about 7.65 to about 7.9, 7.5 to about 7.85, about 7.55 to about 7.85, about 7.6 to about 7.85, about 7.65 to about 7.85, 7.5 to about 7.8, about 7.55 to about 7.8, about 7.6 to about 7.8, about 7.65 to about 7.8, 7.5 to about 7.75, about 7.55 to about 7.75, about 7.6 to about 7.75, about 7.65 to about 7.75, 7.5 to about 7.7, about 7.55 to about 7.7, about 7.6 to about 7.7, about 7.65 to about 7.7, or about 7.684. The pH may be the pH at the beginning of the coating process for a given coating iteration. The pH may be the pH when the solution is at 25° C.

In some embodiments, a buffer is included in the supersatured solution to stabilize pH. In some embodiments, the buffer is tris(hydroxymethyl)aminomethane (tris) buffer. The concentration of tris is from about 1 mM to about 10 mM, about 2 mM to about 10 mM, about 3 mM to about 10 mM, 1 mM to about 8 mM, about 2 mM to about 8 mM, about 3 mM to about 8 mM, 1 mM to about 6 mM, about 2 mM to about 6 mM, about 3 mM to about 6 mM, or about 5 mM.

A salt may be included in the supersatured solution to increase ionic strength. In some embodiments, the salt is sodium chloride. The concentration of salt is from about 100 mM to about 200 mM, about 100 mM to about 175 mM, about 100 mM to about 160 mM, 125 mM to about 200 mM, about 125 mM to about 175 mM, about 125 mM to about 160 mM, 140 mM to about 200 mM, about 140 mM to about 175 mM, or about 140 mM to about 160 mM.

The temperature of the solution during the coating process is from about 40° C. to about 50° C., 42° C. to about 50° C., 44° C. to about 50° C., 46° C. to about 50° C., about 40° C. to about 48° C., 42° C. to about 48° C., 44° C. to about 48° C., 46° C. to about 48° C., 46.5° C. to about 47.5° C., or about 47° C. Implants may be maintained at a process temperature within 0.5° C.

HA is a sparingly soluble salt with a $K_{sp}$ on the order of $10^{-120}$, and thus has a very narrow "meta-stable zone" from which controlled heterogeneous nucleation may occur. Surprisingly, a window was found to exist, allowing for relatively stable supersaturated solutions to precipitate crystalline gallium-substituted HA onto an activated surface of an orthopedic implant in a controlled manner. In identifying this window, it was observed that low supersaturated concentrations led to slow nucleation rates, while high supersaturated concentrations led to uncontrolled, fast nucleation rates, accretion, and inconsistent growth on the substrate. Without intending to be bound by theory, coating under conditions of excessive supersaturation is believed to occur primarily by homogenous nucleation and accretion.

Various conditions, may lead to increased solution stability. In some embodiments, solutions are mixed at room temperature rather than the temperature at which the deposition process takes place. In some embodiments, calcium stock solutions are added to phosphate stock solutions containing NaCl and tris. In some embodiments, the temperature of stock solutions is not below room temperature. In some embodiments, the solution is housed in a vessel having smooth walls rather than rough walls.

Surprisingly, it was possible to identify a window of supersaturated solution concentrations or, alternatively, a window of Gibbs free energy, that allowed for controlled gallium-substituted HA crystal growth in a desirable timeframe. The solutions used in the gallium-substituted SoDHA process were configured such that dG for formation of gallium-substituted HA was from about 7 kJ/mol to about 9 kJ/mol, 7 kJ/mol to about 8.8 kJ/mol, 7 kJ/mol to about 8.6 kJ/mol, 7 kJ/mol to about 9.4 kJ/mol, 7 kJ/mol to about 8.2 kJ/mol, 7.2 kJ/mol to about 9 kJ/mol, 7.2 kJ/mol to about 8.8 kJ/mol, 7.2 kJ/mol to about 8.6 kJ/mol, 7.2 kJ/mol to about 9.4 kJ/mol, 7.2 kJ/mol to about 8.2 kJ/mol, 7.4 kJ/mol to about 9 kJ/mol, 7.4 kJ/mol to about 8.8 kJ/mol, 7.4 kJ/mol to about 8.6 kJ/mol, 7.4 kJ/mol to about 9.4 kJ/mol, 7.4 kJ/mol to about 8.2 kJ/mol, 7.6 kJ/mol to about 9 kJ/mol, 7.6 kJ/mol to about 8.8 kJ/mol, 7.6 kJ/mol to about 8.6 kJ/mol, 7.6 kJ/mol to about 9.4 kJ/mol, 7.6 kJ/mol to about 8.2 kJ/mol, 7.8 kJ/mol to about 9 kJ/mol, 7.8 kJ/mol to about 8.8 kJ/mol, 7.8 kJ/mol to about 8.6 kJ/mol, 7.8 kJ/mol to about 9.4 kJ/mol, 7.8 kJ/mol to about 8.2 kJ/mol, about 8.0 kJ/mol to about 8.4 kJ/mol, about 8 kJ/mol, about 8.2 kJ/mol, or about 8.4 kJ/mol.

The dG for formation of HA without gallium and the relative supersaturations of the solutions with respect to HA without gallium of the SoDHA HA process are listed Table 1. These representative values are not limiting as to the possible values associated with the methods disclosed herein.

TABLE 1

Changes in Energy and Supersaturation Values for SoDHA Process (without gallium)

| dG HA | dG OCP | SS OCP | SS HA |
|---|---|---|---|
| −8.06451 | −3.11966 | 3.230353 | 20.72261 |
| −8.11148 | −3.14875 | 3.265878 | 21.09168 |
| −8.14687 | −3.16101 | 3.280953 | 21.37415 |
| −8.16934 | −3.18283 | 3.307977 | 21.55537 |
| −8.24149 | −3.25443 | 3.398208 | 22.14794 |
| −8.27348 | −3.25519 | 3.399187 | 22.41587 |
| −8.34018 | −3.32947 | 3.495425 | 22.985 |

TABLE 1-continued

Changes in Energy and Supersaturation Values for SoDHA Process (without gallium)

| dG HA | dG OCP | SS OCP | SS HA |
|---|---|---|---|
| −8.34495 | −3.33445 | 3.501971 | 23.0262 |
| −8.34869 | −3.33828 | 3.507014 | 23.05862 |
| −8.3538 | −3.34325 | 3.513581 | 23.10291 |

As further described below, the gallium-substituted hydroxyapatite coatings are formable from supersaturated solutions that remain substantially free of turbidity due to homogenous nucleation in solution throughout the coating process. Without intending to be bound by theory, deposition from solutions substantially free of turbidity due to homogenous nucleation is believed to play a role in gallium-substituted hydroxyapatite coatings deposited with predictable coating rates and having high crystallinity, uniform microstructure, and enhanced biocompatibility.

Gallium-substituted HA is a sparingly soluble salt and has a very narrow "metastable zone" from which controlled heterogeneous nucleation and growth can occur. Surprisingly, it was possible to identify windows of supersaturation levels and temperatures that allowed for controlled gallium-substituted hydroxyapatite crystal heterogeneous nucleation and growth in a desirable timeframe. At these supersaturation values, stable nuclei form and grow from active surfaces, resulting in the gallium-substituted hydroxyapatite coatings described herein.

The gallium-substituted SoDHA process additionally comprises agitating the solution when it is in contact with the substrate. Too little agitation during blending of stock solutions may destabilize the solution. High shear agitation during blending of stock solutions may destabilize the solution. Agitation may occur by stirring.

The process may include reducing the amount of air in contact with the supersaturated solution. In some embodiments, the process may be performed under inert atmospheric conditions, such as under an argon or nitrogen atmosphere. The inert atmosphere limits the dissolution of carbon dioxide into the supersaturated solution, which can change the pH without CaP precipitation, interfering with the use of pH as an internal process monitor. Under such conditions, the resulting gallium-substituted hydroxyapatite coatings are substantially free of carbonate.

Figure 11:
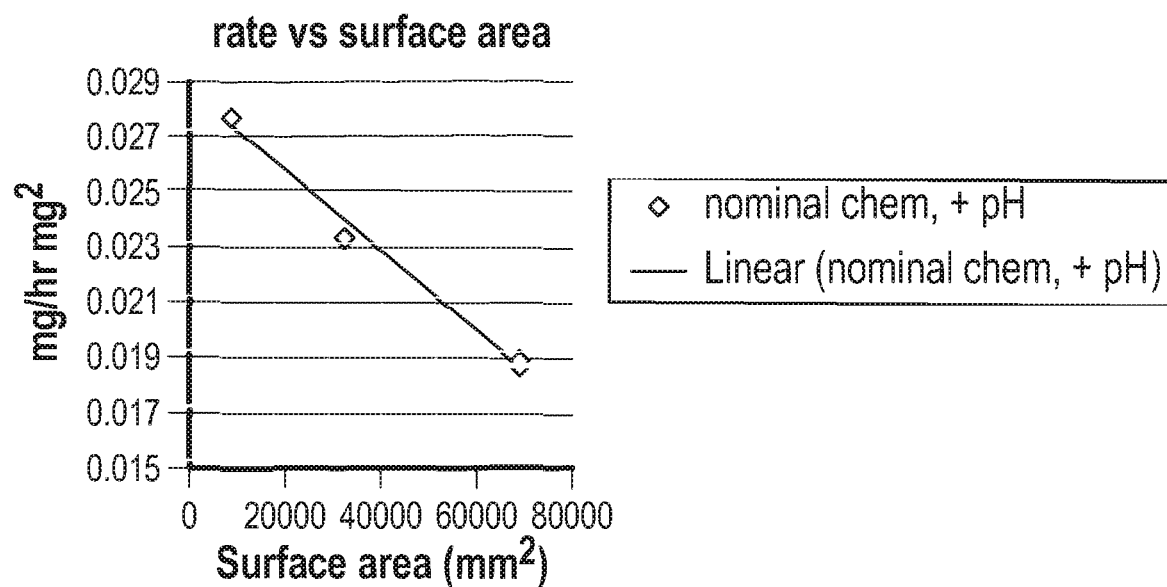
FIG. 11 is a chart showing deposition rates at different surface areas for a solution deposited hydroxyapatite (SoDHA) process.

The process occurs at a controlled, but relatively rapid coating rate. Coating rate can be described in terms of coating mass or coating thickness. For a fixed number of implants in the coating solution, higher coating weights are obtained on implants with high specific surface area like those coated with porous metal in-growth structures. Coating thickness however, is approximately independent of the specific surface area of the implant. Finally, both mass and thickness based coating rates are a function of total surface area/coating solution volume as seen in FIG. 11.

The process deposits gallium-substituted HA such that thickness increases at a rate of about a rate of about 0.01 μm/h to about 10 μm/h, about 0.01 μm/h to about 5 μm/h, about 0.01 μm/h to about 4 μm/h, about 0.01 μm/h to about 3 μm/h, about 0.01 μm/h to about 2 μm/h, about 0.01 μm/h to about 1 μm/h, a rate of about 0.1 μm/h to about 10 μm/h, about 0.1 μm/h to about 5 μm/h, about 0.1 μm/h to about 4 μm/h, about 0.1 μm/h to about 3 μm/h, about 0.1 μm/h to about 2 μm/h, about 0.1 μm/h to about 1 μm/h, a rate of about 0.5 μm/h to about 10 μm/h, about 0.5 μm/h to about 5 μm/h, about 0.5 µm/h to about 4 µm/h, about 0.5 µm/h to about 3 µm/h, about 0.5 µm/h to about 2 µm/h, or about 0.5 µm/h to about 1 µm/h.

The process deposits HA on Gription at a rate of about 0.005 mg/hr·mm² to about 0.09 mg/hr·mm², about 0.005 mg/hr·mm² to about 0.025 mg/hr·mm², 0.005 mg/hr·mm² to about 0.0225 mg/hr·mm², 0.005 mg/hr·mm² to about 0.02 mg/hr·mm², 0.005 mg/hr·mm² to about 0.0175 mg/hr·mm², about 0.005 mg/hr·mm² to about 0.015 mg/hr·mm², about 0.0075 mg/hr·mm² to about 0.09 mg/hr·mm², about 0.0075 mg/hr·mm² to about 0.025 mg/hr·mm², 0.0075 mg/hr·mm² to about 0.0225 mg/hr·mm², 0.0075 mg/hr·mm² to about 0.02 mg/hr·mm², 0.0075 mg/hr·mm² to about 0.0175 mg/hr·mm², about 0.0075 mg/hr·mm² to about 0.015 mg/hr·mm², about 0.025 mg/hr·mm² to about 0.09 mg/hr·mm², about 0.01 mg/hr·mm² to about 0.025 mg/hr·mm², 0.01 mg/hr·mm² to about 0.0225 mg/hr·mm², 0.01 mg/hr·mm² to about 0.02 mg/hr·mm², 0.01 mg/hr·mm² to about 0.0175 mg/hr·mm², or about 0.01 mg/hr·mm² to about 0.025 mg/hr·mm².

The coating process may be a "Constant Composition" or "Variable Composition" process.

In a constant composition process, reactants that are consumed by deposition of gallium-substituted hydroxyapatite on implants are semi-continuously added back to the deposition solution throughout the coating process. The addition of reagents is performed based on the drop in pH that corresponds to precipitation of gallium-substituted hydroxyapatite from solution. Thus, the amount of process reagents that are added back to the deposition solution become a surrogate for the amount of gallium-substituted hydroxyapatite deposited on the implants. Without intending to be bound by theory, the equations that calculate the composition of the "titrant" (the solutions that are added back to the deposition vessel in response to a change in pH induced by CDHA precipitation), when gallium is not included in the HA, may be:

$$TCaNO3=(Nb)(W_{CaNO3})+(10-x)Ceff$$

$$TP=(Nb)(W_{PO4})+6Ceff$$

$$TNaCl=(Nb)(W_{NaCl})-(20-2x)Ceff$$

$$TKOH=(Nb)(W_{KOH})+(14-2x)Ceff$$

where Ceff is equal to the moles of CaP precipitated per Liter of added titrant and x is the non-stoichiometric coefficient in CDHA, Nb=number of burets adding titrants to solution, and W is the concentration of reactants in the supersaturated solution.

In the variable composition process, chemical driving forces for precipitation are allowed to fall from their initial conditions by an amount that maintains a high range of driving force rather than a constant high driving force as is accomplished by the constant composition process. When the low limit of driving force is reached by depletion of some fraction of coating reagents by precipitation of CaP from solution, the coating solution is discarded and a new coating solution is added to the deposition process vessel. One embodiment of the variable composition process utilizes the quantitative relationship between change in solution pH and the amount and composition of gallium-substituted hydroxyapatite that precipitates from the coating solution. This relationship can be used to determine when to discard coating solutions and replace them with fresh solution as well as to determine the predetermined process endpoint where gallium-substituted hydroxyapatite coating weights have been met. The amount of buffer is selected to lessen the pH reduction that accompanies gallium-substituted hydroxyapatite precipitation while allowing pH to reduce enough to allow the use of pH change as an internal process diagnostic. In some embodiments, the pH measurements may be made intermittently rather than continuously. Coating rates are increased at lower deposition sequence times with greater numbers of coating sequences. In some embodiments, the coating solutions lack carbonate, which may assist with the use of pH as a process monitor or control during coating formation.

Without intending to be bound by theory, the reactions, when gallium is not included, are believed to proceed by the stoichiometry indicated by Table 2.

TABLE 2

| Stoichiometry for HA and OCP Processes | | | | | |
|---|---|---|---|---|---|
| HA | | | OCP | | |
| $Ca_{10}$ | $(PO4)_6$ | $(OH)_2$ | $Ca_8$ | $(HPO_4)_2$ | $(PO_4)_4$ |
| | $-6\ H_2PO_4$ | | | $-2\ HPO_4$ | $-4\ H_2PO_4$ |
| | $+12\ H$ | $+2\ H$ | | | $+8\ H$ |
| | $+14\ H_2PO_4$ | $-14\ HPO_4$ | | $-8\ HPO_4$ | $+8\ H_2PO_4$ |
| Totals | $+8\ H_2PO_4$ | $-14\ HPO_4$ | | $-10\ HPO_4$ | $+4\ H_2PO_4$ |

As shown in Table 2, precipitation of calcium phosphate is accompanied by a drop in calcium and phosphate concentrations, and a decrease in pH. These changes in concentration and pH result in a reduction in degree of supersaturation as the reaction progresses, along with a decrease in deposition rate.

The relationship between pH and amount of precipitate is scalable to different solution volumes. This relationship between change in pH and amount of phase precipitated may be utilized as a process monitor to ensure that a predictable amount of precipitate is formed.

The pH of the supersaturated solution may be monitored to determine the extent of coating that has taken place. In some embodiments, the substrate is contacted by the solution until one or more of the calcium concentration, phosphate concentration, and pH decrease to a predetermined level.

Although nucleation rates, growth rates, and relative driving forces for gallium-substituted SoDHA change as gallium-substituted HA precipitates, a process was developed to minimize changes in these values as precipitation proceeds. The process used for coating the implants was a variable composition process. As used herein, a variable composition process refers to a process that allows for change in thermodynamic variables over the course of the process. In the variable composition process described herein, implants may be coated by multiple batches of solution, allowing ion concentrations and pH to fall only to a predetermined level during each of the iterations. To reduce the extent of concentration changes, multiple sequential depositions were used, with each deposition sequence comprising contacting the orthopedic implant with fresh solution. The pH change associated with deposition may be reduced by buffering the solution with a buffer, such as TRIS buffer.

In some embodiments, three sequential depositions were performed. For a three sequential deposition process, concentration changes during each deposition sequence are reduced by two thirds compared to one deposition sequence. In some embodiments, only one deposition sequence is performed. In some embodiments, 2 or 3 deposition sequences are performed. 1 to 10, 2 to 10, 3 to 10, 1 to 5, 2 to 5, or 3 to 5 deposition sequences may be performed. In some embodiments, the number of deposition sequences employed depends on the ratio of the surface area of the implant to the volume in the coating vessel. Larger implant surface area/volume ratios may correspond with a larger number of shorter coating sequences. Lower surface area/volume ratios may correspond with fewer sequences of longer duration per sequence. The combination of pH buffering and refreshing of solutions minimizes the change in thermodynamic driving forces and may help to ensure that the same calcium phosphate phase is produced throughout the deposition process.

The total contact time with the solution deposition composition in accordance with the inventive method typically is about 30 minutes or more. The total contact time preferably is about 8 hours or less. More preferably, the biocompatible substrate is subjected to multiple sequence contact times of about 1 minute to about 2 hours, about 1 minute to about 1 hour, about 1 minute to about 30 minutes, about 5 minutes to about 2 hours, about 5 minutes to about 1 hour, about 5 minutes to about 30 minutes, about 2 hours or less, about 1 hour or less, or about 30 minutes or less. In general, longer total contact times and shorter coating sequences provide greater thicknesses of the bioactive hydroxyapatite coating. Additionally, the contact time is dependent on the number of bioactive substrates being coated at any one time.

In some embodiments, the relationship between weight of precipitate and change in pH is used to monitor the progression of the SoDHA-G process. In additional embodiments, the relationship between weight of precipitate and change in calcium and/or phosphate concentration may be used to monitor the progression of the SoDHA-G process. In other embodiments, the process is performed for a predetermined amount of time and pH, calcium concentration, and phosphate concentration are not monitored.

In some embodiments, a supercritical fluid may be employed to dry SoDHA-G coatings. This process includes displacing water from a coating with an organic solvent followed by supercritical fluid extraction. After SoDHA-G coating formation, organic solvent exchange is performed by immersing coated articles in the organic solvent for a predetermined period of time. After displacement of the organic solvent in the coating, the coated article is placed in a vessel where a supercritical fluid is introduced. Next, the vessel is depressurized to atmosphere while maintaining the temperature above the critical temperature of the supercritical fluid. In this way the supercritical fluid is depressurized directly from a supercritical state to a gas, which avoids creation of liquid capillary forces that may cause cracks.

In some embodiments, the organic solvent is an alcohol. For example, the organic solvent may be methanol, ethanol, or isopropanol. In some embodiments, the supercritical fluid is supercritical $CO_2$ (sc$CO_2$).

Additionally, in some embodiments, the SoDHA-G coatings may be exposed to hydrothermal re-precipitating conditions. After SoDHA-G coating formation, the coatings may be placed in phosphate-gallium solution and heated. This hydrothermal treatment may be performed at temperatures from about 50° C. to about 350° C., about 60° C. to about 350° C., about 70° C. to about 350° C., about 80° C. to about 350° C., about 50° C. to about 150° C., about 60° C. to about 150° C., about 70° C. to about 150° C., about 80° C. to about 150° C., about 50° C. to about 99° C., about 60° C. to about 99° C., about 70° C. to about 99° C., about 80° C. to about 99° C., about 50° C. to about 95° C., about 60° C. to about 95° C., about 70° C. to about 95° C., about 80° C. to about 95° C., about 50° C. to about 90° C., about 60° C. to about 90° C., about 70° C. to about 90° C., about 80° C. to about 90° C., about 50° C. to about 85° C., about 60° C. to about 85° C., about 70° C. to about 85° C., about 80° C. to about 85° C., about 50° C. to about 80° C., about 60° C. to about 80° C., or about 70° C. to about 80° C. The coatings may be heated for times from about 15 minutes to about 24 hours, about 15 minutes to about 4 hours, about 15 minutes to about 3 hours, about 15 minutes to about 2 hours, about 30 minutes to about 24 hours, about 30 minutes to about 4 hours, about 30 minutes to about 3 hours, about 30 minutes to about 2 hours, about 1 hour to about 24 hours, about 1 hour to about 4 hours, about 1 hour to about 3 hours, about 1 hour to about 2 hours, or about 2 hours.

The methods described herein maximize the amount of material that grows on the substrate, and minimize the amount that accretes onto the surface from material homogeneously precipitated in suspension. Additionally, these methods provide for a controlled, predictable deposition rate, produce films with high adhesion and cohesion, and produce a uniform microstructure that degrades uniformly without release of particulates. Predictable deposition rates allow targeted film thicknesses to be readily achieved. The methods also provide suitable coverage of porous structures and are suitable for various implant geometries.

Definitions

As used herein, relative supersaturation of a product (S) is defined by the following equation: $S=[IAP/K_{sp}]^{1/v}$, where IAP is the ionic activity of the product, $K_{sp}$ is the solubility constant of the product, and v is the number of ions in the unit formula of the product.

As used herein, Gibbs free energy change (dG) associated with a phase change is defined by the following equation: $dG=RT/v*\ln[IAP/K_{sp}]$, where R is the universal gas constant, T is absolute temperature, IAP is the ionic activity of the product, $K_{sp}$ is the solubility constant of the product, and v is the number of ions in the unit formula of the product.

As used herein, relative supersaturation S, is equal to $(IAP/K_{sp})^{1/v}$.

As used herein, homogenous precipitation or homogenous nucleation refers to nucleation of a solid phase from a supersaturated solution that does not involve a foreign surface, resulting in a turbid supersaturated coating solution.

As used herein, heterogeneous precipitation or heterogeneous nucleation refers to nucleation of a solid phase on an impurity phase from a supersaturated solution that is substantially free of turbidity during the deposition process.

As used herein, "octacalcium phosphate" or "OCP" refers to a calcium phosphate having the formula $Ca_8(HPO_4)_2(PO_4)_4$.

As used herein, supersaturated refers to a solution in which a solute is concentrated beyond equilibrium. When concentration is above the saturation point, the solution is said to be supersaturated.

As used herein, in vitro, in reference to dissolution studies, means in a tris buffered saline solution at pH 7.4, as described in ASTM F1926.

Example 1—Activation of CoCr by Atomic Layer Deposition of $TiO_2$ Films $TiO_2$ films were prepared on CoCr grit blast surfaces by Beneq (Helsinki, Finland) by atomic layer deposition. The films were produced from $TiCl_4$ and $H_2O$ precursors. Amorphous films were produced at 90° C. and crystalline (Anatase plus Rutile) films were produced at 200° C. Films were activated with hydroxide, according to the methods described in Example 3 (4 hrs, 5M NaOH, 60° C.). 500, 200, 100, and 50 nm amorphous films (500 A, 200 A, 100 A, and 50 A) and 500 and 200 nm crystalline films (500° C., 200° C.) were evaluated for their ability to form hydroxyapatite coatings according to the SoDHA method using nominal concentrations, as further described in Examples 5 and 6.

HA coating weight for the samples ranged from about 6 mg to about 8 mg, as shown in FIG. 1. Both amorphous and crystalline films were able to nucleate HA after activation by strong base. Coating experiments showed that deposition occurred for as deposited crystalline titanium oxide, but at lower rates than observed for NaOH etched amorphous or crystalline titanium oxide.

Figure 2:
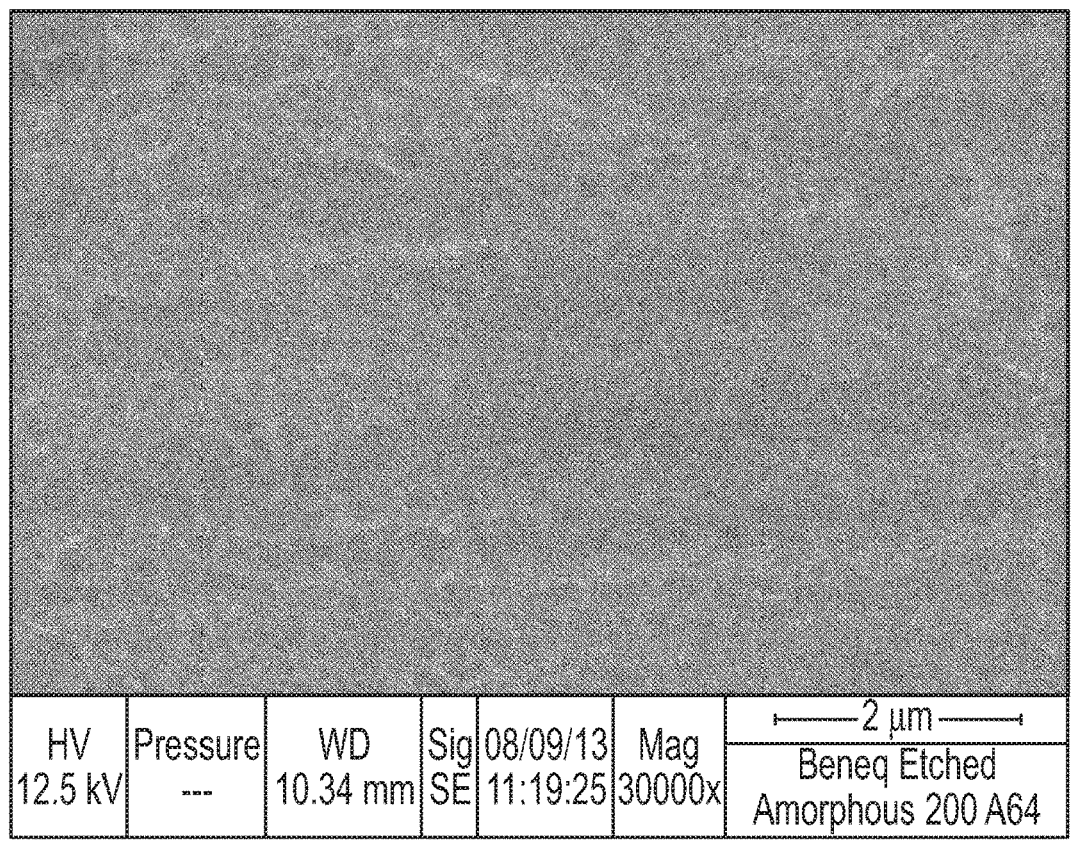
FIG. 2 is a scanning electron microscopy (SEM) image of a 200 nm-thick amorphous $TiO_2$ coating after treatment with hydroxide.
Figure 3:
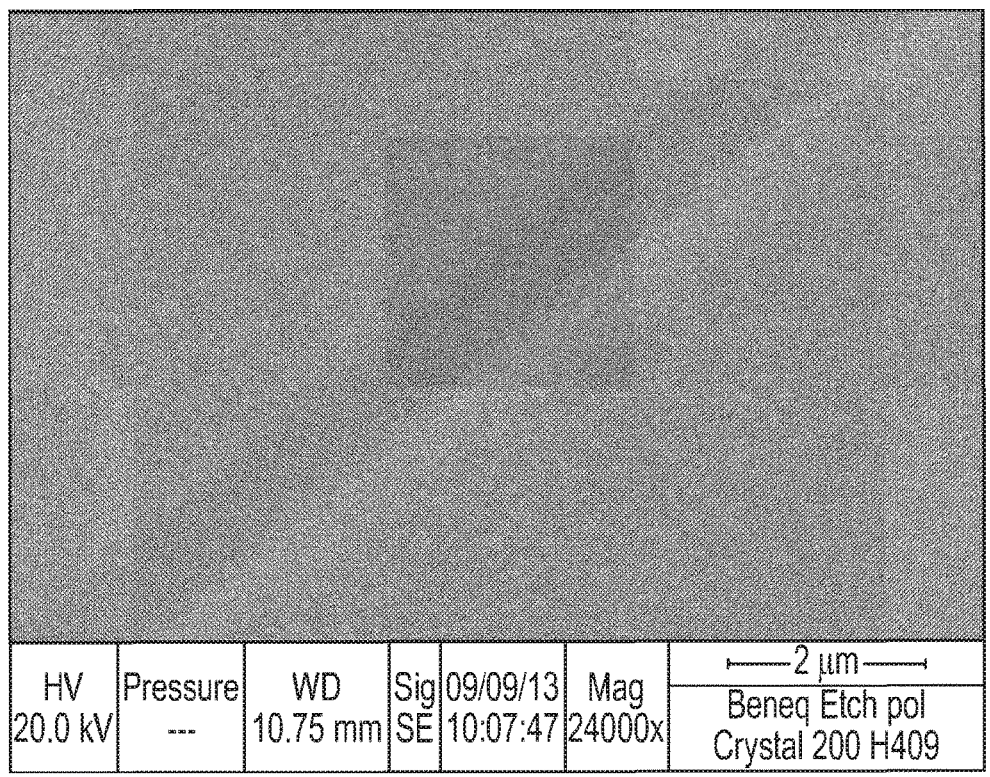
FIG. 3 is an SEM image of a 200 nm-thick crystalline $TiO_2$ coating that was not treated with hydroxide.

A scanning electron microscopy (SEM) image of the 200 nm-thick, activated amorphous film, prior to HA coating is shown in FIG. 2. An SEM image of the 200 nm-thick, activated crystalline film, prior to HA coating is shown in FIG. 3. The characteristic titanate topography was apparent on amorphous films. Films prepared over 100 nm thick showed interference colors after hydroxide treatment.

Figure 4:
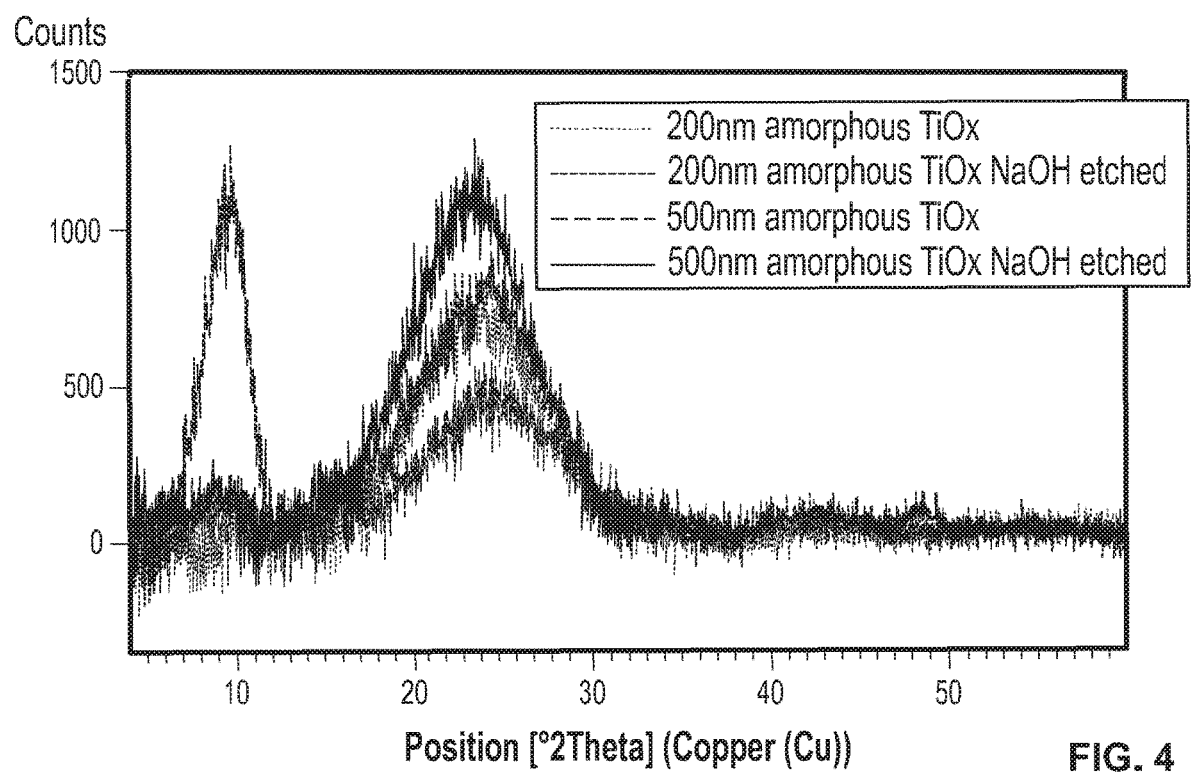
FIG. 4 is a grazing angle X-ray diffraction (XRD) spectrum overlay, showing spectra for 200 nm-thick amorphous $TiO_2$ coatings, with and without hydroxide treatment, and 500 nm-thick amorphous $TiO_2$ coatings, with and without hydroxide treatment.
Figure 5:
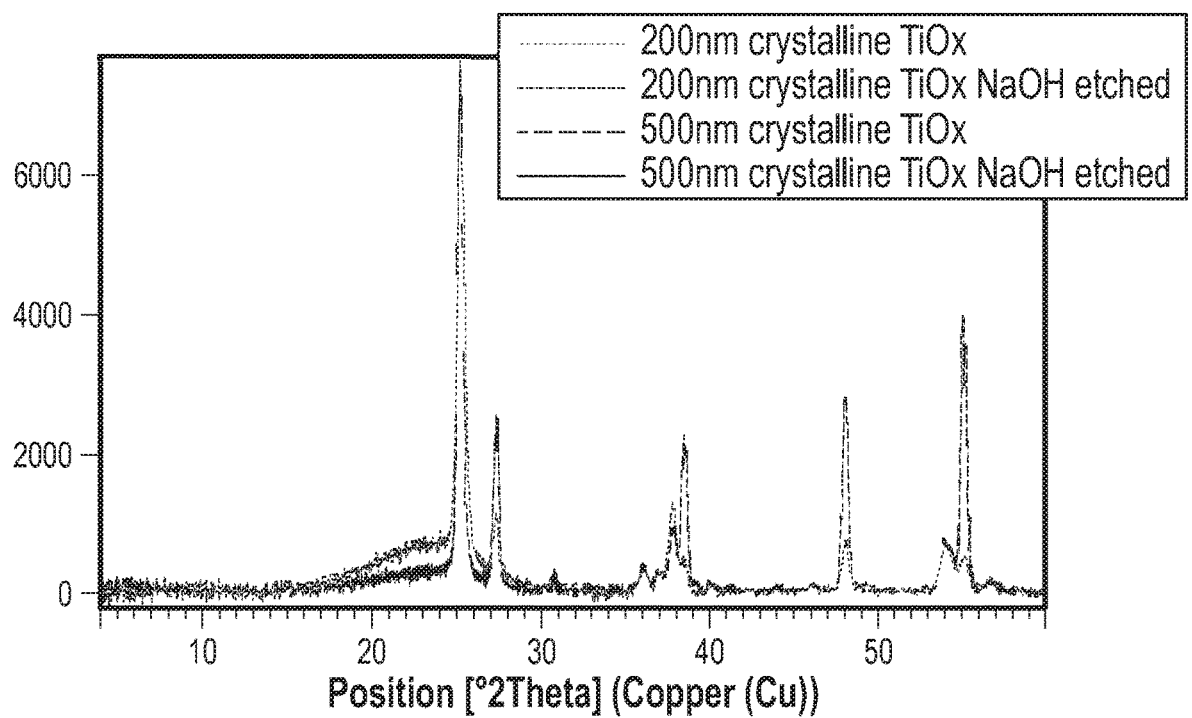
FIG. 5 is a grazing angle XRD spectrum overlay, showing spectra for 200 nm-thick crystalline $TiO_2$ coatings, with and without hydroxide treatment, and 500 nm-thick crystalline $TiO_2$ coatings, with and without hydroxide treatment.

Grazing angle X-ray diffraction (XRD) spectra were obtained for amorphous and crystalline titanium coatings at 200 nm-thick and 500 nm-thick before and after activation with NaOH. The XRD spectra for the amorphous films are shown in FIG. 4. The XRD spectra for the crystalline films are shown in FIG. 5.

Example 2—Electrolytic Formation of $TiO_2$ Films on CoCr Alloy

An electrolyte solution of 0.05 M $TiCl_4$ and 0.25 M $H_2O_2$ in a mixed methanol/water (3/1 vol %) solvent was prepared. The pH of the solution was fixed between 0.9 and 1.0. All chemicals were ACS grade. To prepare the electrolyte solution, $TiCl_4$ was slowly added to the solvent, followed by $H_2O_2$. During the addition of $H_2O_2$, an immediate color change from transparent to dark orange was observed, indicating the formation of a peroxo-complex. Electrolytes were stored at about 4° C. after preparation and pH measurement and, if necessary, pH adjustment. Electrodeposition was performed galvanostatically up to the desired charge density. The temperature was fixed by a cryostat to 0° C. A homemade Labview program (controlling a Xantrex XDC 300-20 power source) was built to control current charge density while recording voltage-time curves. The applied charge density was fixed in the range form 2.5 $C/cm^2$ to 40 C $C/cm^2$. The current density was varied between −50 $mA/cm^2$ to −50 $mA/cm^2$.

Figure 6:
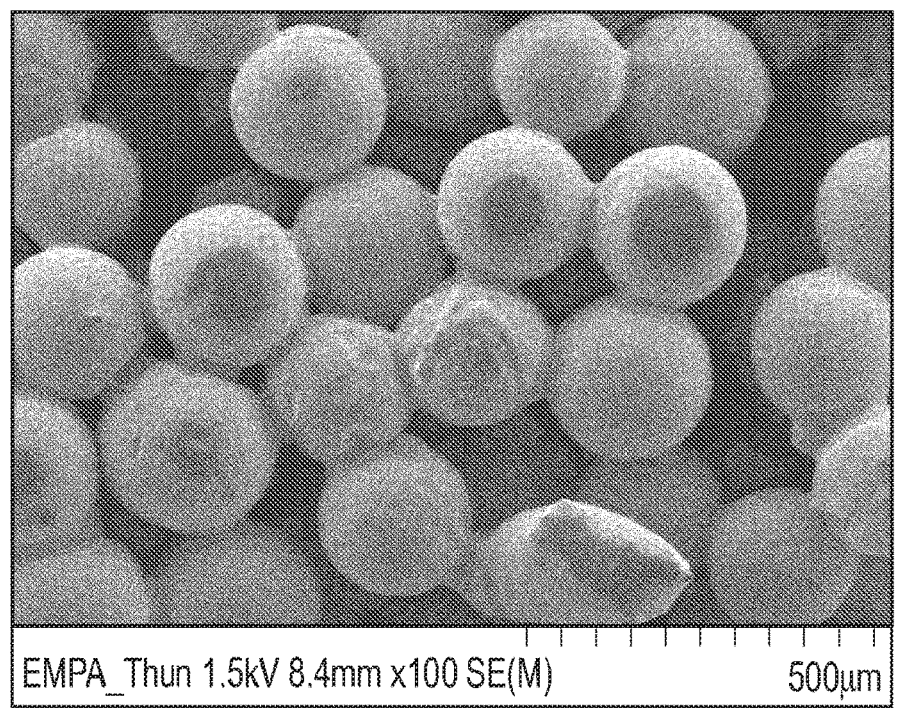
FIG. 6 is an SEM image of a titanium layer that has been electrodeposited onto a CoCrMo core.

Good film uniformity was obtained in 0.05 M $TiCl_4$, 0.5 M $H_2O_2$ in a mixed methanol/water (3:1 vol. %) solvent (pH=0.97). Good growth occurred at −1.1 V for 1 hour at 60° C. FIG. 6 is an SEM image showing a titanium coating electrodeposited under these conditions on a CoCrMo substrate.

Example 3: Titanium Surface Activation 1 inch diameter Ti6-4 disks coated with DePuy Gription porous metal coating were cleaned and activated by the following steps. Disks were set in a container with reverse osmosis (RO) water and alkaline detergent for 15 min with a sonicator 2 times. Next, disks were set in a container with only RO water for 15 minutes with a sonicator 2 times. 4 disks were placed in a 500 mL beaker and 200 mL of 5M NaOH was added. The disks were placed in secondary containment and a loose cap was set over the top of the beaker. The temperature of the beaker was set to 60° C. and held for 4 hrs. The desks were removed from the beaker and rinsed in RO water in a sonicator for 15 minutes 4 times. Disks were left in a 60° C. oven overnight to dry. No effect of heat treatment of this activation layer on the tendency to promote nucleation and growth of CaP coatings was found in the methods disclosed herein, and examples reported below were performed without heat treatment of the activated surface. Coating experiments showed that deposition occurred for crystalline titanium, but at lower rates than observed for NaOH etched amorphous titanium.

Example 4: Stock Solution Preparation

Concentrate and stock solutions for HA coating of 1 inch diameter disks in a 1 L vessel were prepared by the following steps.

A 36 mM Ca solution was prepared. A clean 2-liter bottle was obtained and a magnetic stir bar was placed in the bottle. 8.50194 g of $Ca(NO_3)$ was weighed out and poured into the 2-liter bottle. The bottle was purged with Argon for 3-5 minutes. 1000 mls of deionized (DI) water with a resistivity of 18 MΩ or higher was added to the bottle. The bottle was placed on stir plate and its contents were stirred until $Ca(NO_3)$ was fully dissolved. The solution was filtered using a 0.22 μm cell culture vacuum filter (Corning, Funnel Volume, 1000 mL; Receiver: 90 mm; Pore Size: 0.22 um; PES, No.: 431098).

A 40 mM phosphate (Pt) solution was prepared. A clean 2-liter bottle was obtained and a magnetic stir bar was placed in the bottle. 5.444 g of $KH_2PO_4$ was weighed out and poured into the 2-liter bottle. 19.0387 g of Tris and 273.675 g NaCl were weighed out and added to the bottle. The bottle was purged with Argon for 3-5 minutes. 898.1 mL of 18 MΩ or higher DI water was added. Using a manual pipette, 5.8 mL of 6N HCl was added to the bottle. The bottle was placed on a stir plate and stirred until the Tris, NaCl, and $KH_2PO_4$ were fully dissolved. The final volume of the solution was 1 L and the pH of the solution was approximately 8.23 at 25° C. If necessary, pH may be adjusted to this value using HCl or NaOH. The solution was filtered using a 0.22 um cell culture vacuum filter (Corning, Funnel Volume, 1000 mL; Receiver: 90 mm; Pore Size: 0.22 um; PES, No.: 431098).

495.3 mls of a 2.0787 mM Ca stock solution was prepared. The previously prepared 36 mM calcium solution was placed on a stir plate and stirred for five minutes. A clean 1-liter bottle was purged with Argon. 28.6 mL of 36 mM calcium solution was added using a pipette. 466.7 mL of 18 MΩ or higher DI water was added.

500 mL of 2.5690 mM $P_i$ stock solution was prepared. The previously prepared 40 mM phosphate solution was placed on stir plate for five minutes. A clean 1-liter bottle was purged with Argon. 32.112 mL of 40 mM phosphate solution was added using a pipette. 467.888 mL of 18 MΩ or higher DI water was added.

A 1.7792 mM Ca solution was prepared. The previously prepared 36 mM calcium solution was placed on a stir plate and stirred for five minutes. A clean 1-liter bottle was purged with Argon. 36 mM calcium solution and 18 MΩ DI water were mixed to achieve the desired concentration.

A 2.2262 mM 500 mL $P_i$ solution was prepared. The previously prepared 40 mM phosphate solution was placed on stir plate for five minutes. A clean 1-liter bottle was purged with Argon. 40 mM phosphate solution and 18 MΩ DI water were mixed to achieve the desired concentration.

A gallium/phosphate stock solution was prepared. First, approximately 2 L of 1.2730 mM Phosphate stock solution was prepared by dilution of 40 mM phosphate concentrate, as described above. This solution was set aside and a second, clean 2 L bottle was obtained. $GaNO_3$ hydrate was weighed on a balance, based on the desired wt % Ga in the $GaNO_3$/Phosphate solution, and added to a second empty, clean 2 L bottle. Approximately 200-300 mL of phosphate stock was added to the 2 L bottle containing the $GaNO_3$. A cap was placed on the bottle containing the $GaNO_3$ and 200-300 mL of phosphate stock. A cloudy solution was formed by shaking the bottle. The solution was transferred into a clean, 500 mL volumetric flask. Phosphate stock was added to the volumetric flask until the fill line was reached. The contents of the volumetric flask were transferred back into the 2 L bottle that previously contained the solution. The volumetric flask was filled two more times with phosphate stock and each time the stock was added to the 2 L bottle with $GaNO_3$. Another 50 mL of phosphate stock was measured out in a graduated cylinder and added to the $GaNO_3$ solution. The 2 L bottle containing the solution was capped and shaken again to double-check that all solids have been dissolved to form the $GaNO_3$/Phosphate solution.

The gallium/phosphate prepared at ratios of 5 to 20 wt % Ga. After thorough mixing the pH was adjusted between 8.3 and 8.4 with micro-liter additions of 6N NaOH.

Example 5: HA Coating by Solution Deposition in 1 L Vessel 1 inch diameter porous metal coated titanium coupons were coated. A cover for a 1 L jacketed vessel was provided to allow for an Ar cover gas during process the deposition process. 500 mLs of 2.569 mM phosphate stock solution prepared according to Example 4 was added into the 1 L jacketed vessel, and the vessel was placed on a stir bar plate. The stir bar was turned on at 200 rpm. Next, 495.3 mL of 2.0787 mM Ca stock solution, prepared according to Example 4 was poured into the vessel. Total volume at 25° C. was 1 L due to volume expansion associated with NaCl dilution. The pH of the solution was 7.68 and the calculated dG was 8.242. Relative SS for HA was 22.15 at the initiation of the coating process. A heated water bath was circulated through the jacketed vessel, and the solution was allowed to reach 47° C. The temperature was controlled within 0.5° C. Temperature sensors were calibrated to a NIST traceable RTD. The etched (activated) disks were placed in fixtures that allowed disks to be suspended in the 1 L jacketed vessel.

After coating, the disks were moved into a first container of DI water and allowed to soak for 1 minute. Next, the disks were moved from the first container to a second container of DI water and allowed to soak for 1 minute. Then, disks were moved from the second container to a third container of DI water and allowed to soak for 1 minute. After soaking, the disks were moved to a 6-well tray and placed in a 60° C. oven to dry for 60 min.

This process was repeated three times with a fresh solution each time. Each sequence was controlled to a fixed value of dpH. For larger implant SA/V ratios a larger number of shorter coating sequences may be used. For lower SA/V ratios, fewer sequences of longer duration per sequence may be used. At the SA/V ratio equal to 941 $mm^2/L$ used in the animal study (Example 17), a total coating time of 5.73 hours with 2.35 coating sequences of 2.44 hour duration per sequence was used.

After coating, the disks were moved into a first container of DI water and allowed to soak for 1 minute. Next, the disks were moved from the first container to second container of DI water and allowed to soak for 1 minute. Then, disks were moved from the second container to a third container of DI water and allowed to soak for 1 minute. After soaking, the disks were moved to a 6-well tray and placed in a 60° C. oven to dry for 60 min.

Example 6: Full Scale Process Validation

Figure 7:
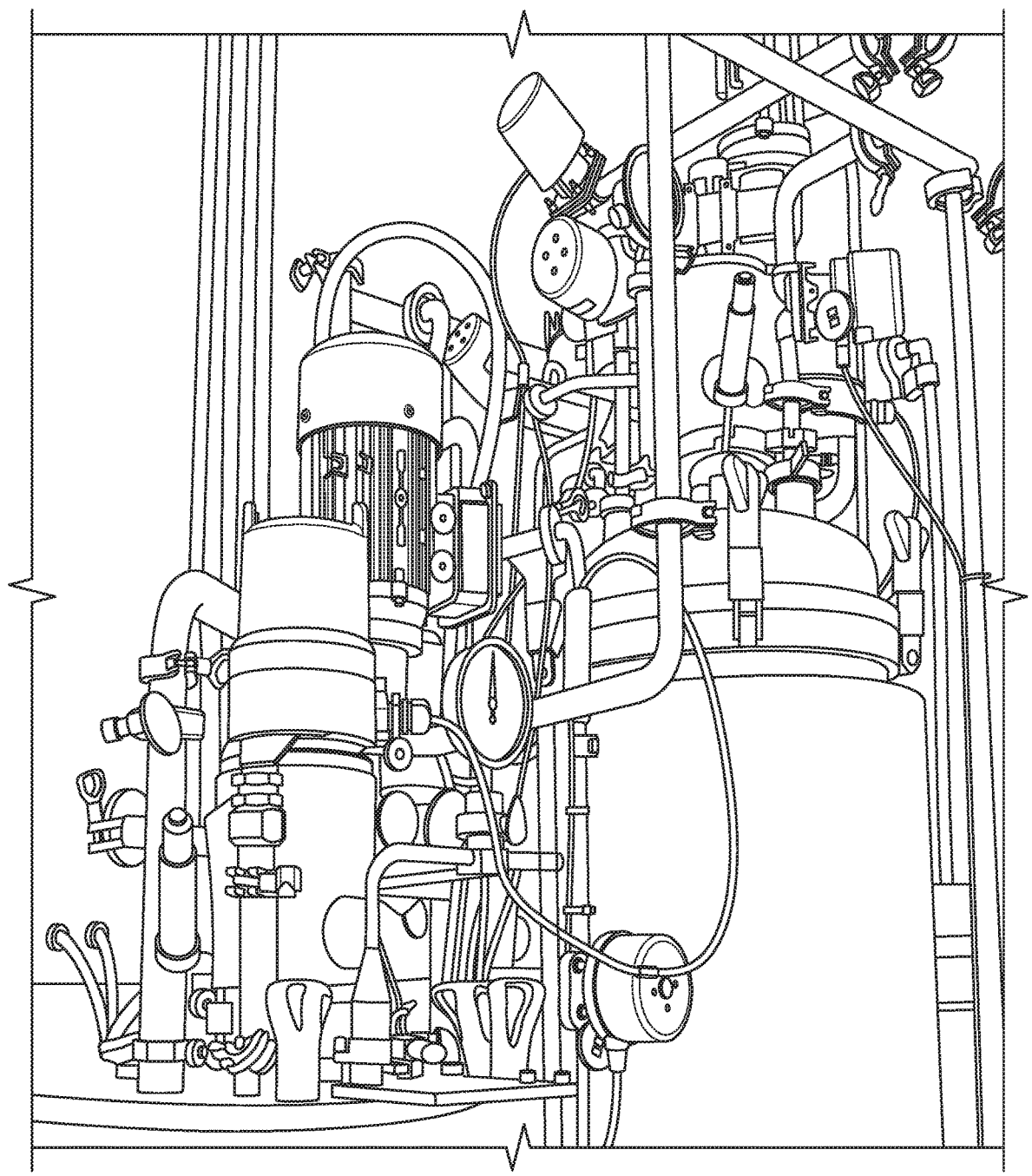
FIG. 7 is an image of a full scale coating vessel.
Figure 17:
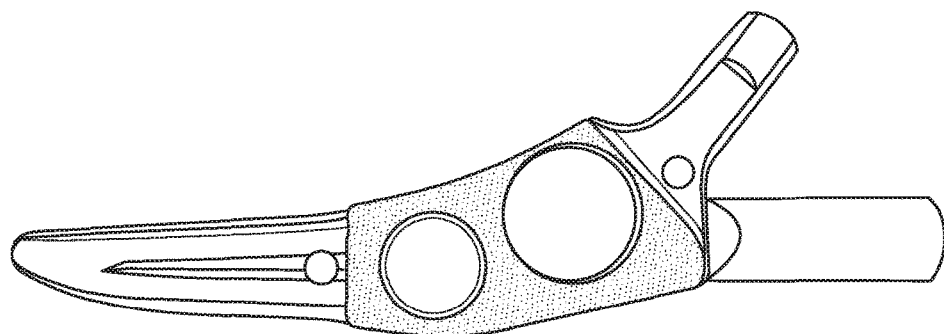
FIG. 17 shows a hip stem coupon fixture used in the XRD characterization study described herein.

The nominal process described in Example 5 was repeated using a "full scale" system shown in FIG. 7. The full scale system is designed to coat up to 40 acetabular cups or 16 hip stems in a single coating run of one or more coating sequences. A series of coating runs were made utilizing both standard DePuy TriLock BPS hip stems or hip stems modified to accept one-inch diameter coupons (shown in FIG. 17) were made at nominal as well as + and − process limits. Process limits were defined as + and −2% of Ca and Phosphate concentrations and +−0.06 pH units. Coatings were characterized by various methods as described in the examples.

Figure 10:
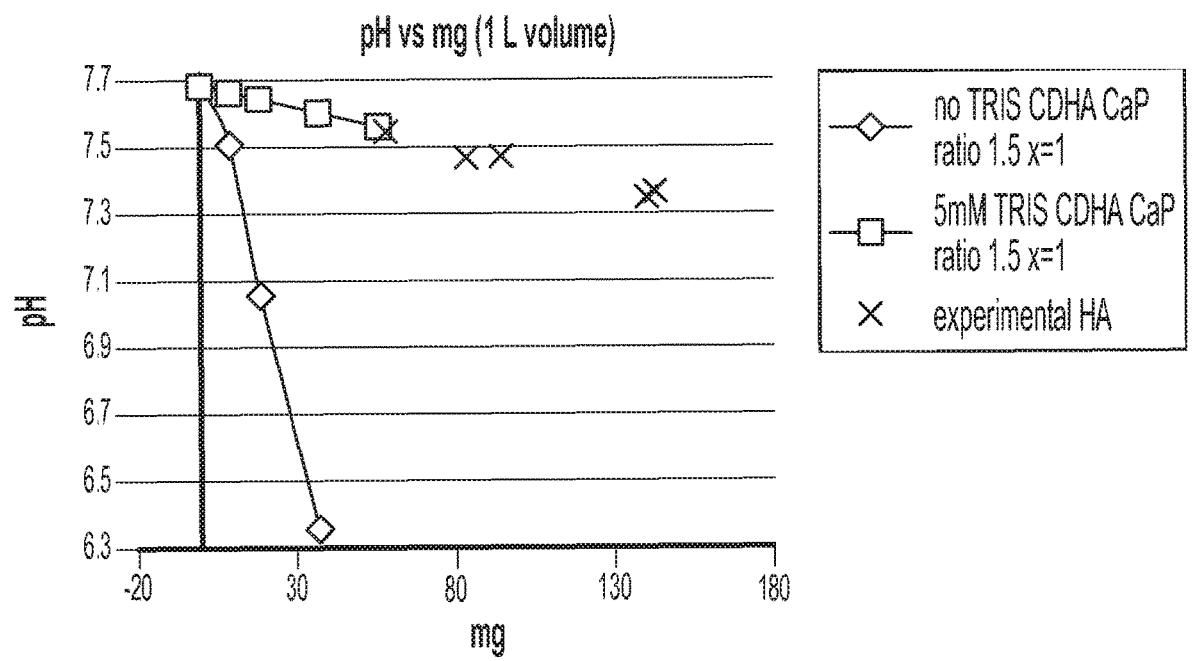
FIG. 10 is a chart showing a relationship between pH and the weight of hydroxyapatite precipitate precipitate over the course of their respective deposition processes.

Example 7: Use of dpH as a Process Monitor pH and precipitate mass were monitored for the SoDHA process described in Example 5 at nominal values, the SoDHA process described in Example 5 at nominal values without tris, and the SoDHA process described in Example 5 at nominal values with 5 mM. The relationship between pH and amount of precipitate is scalable to different solution volumes and buffer strengths using a solution thermodynamics software such as "Chemist" version 1.0.3 from Micromath Scientific Software, 9202 Litzsinger Road Saint Louis, Mo. 63144. This relationship between change in pH and amount of phase precipitated may be utilized as a process monitor to verify that a targeted amount of precipitate is formed. A spreadsheet calculator was constructed based on the relationships summarized in Table 2 to calculate the concentrations and activities of reactants as a function of amount of CaP phase precipitated. CaP phases that can be modeled by this calculator include stoichiometric HA, stoichiometric OCP, non-stoichiometric CDHA, and mixtures of HA or CDHA with OCP. For each increment of CaP phase precipitated, the reduced reactant concentrations were input into Chemist, which calculates the system pH based on buffer type and levels being analyzed. FIG. 10 shows predicted vs experimental plots of pH as a function of total mg precipitated of CaP comprised of:

1) CDHA of formula $Ca_{10-x}(PO_4)_{6-x}(HPO_4)_x(OH)_{2-x}$ with x=to 1.0
   a) without TRIS buffer
   b) with 5 mM TRIS buffer
2) A mixture of 80% OCP and 20% CDHA with x=1.5 with 5 mM TRIS.

Experimental values in this plot are taken from Example 5.

Example 8: Characterization of HA Coating

Figure 8:
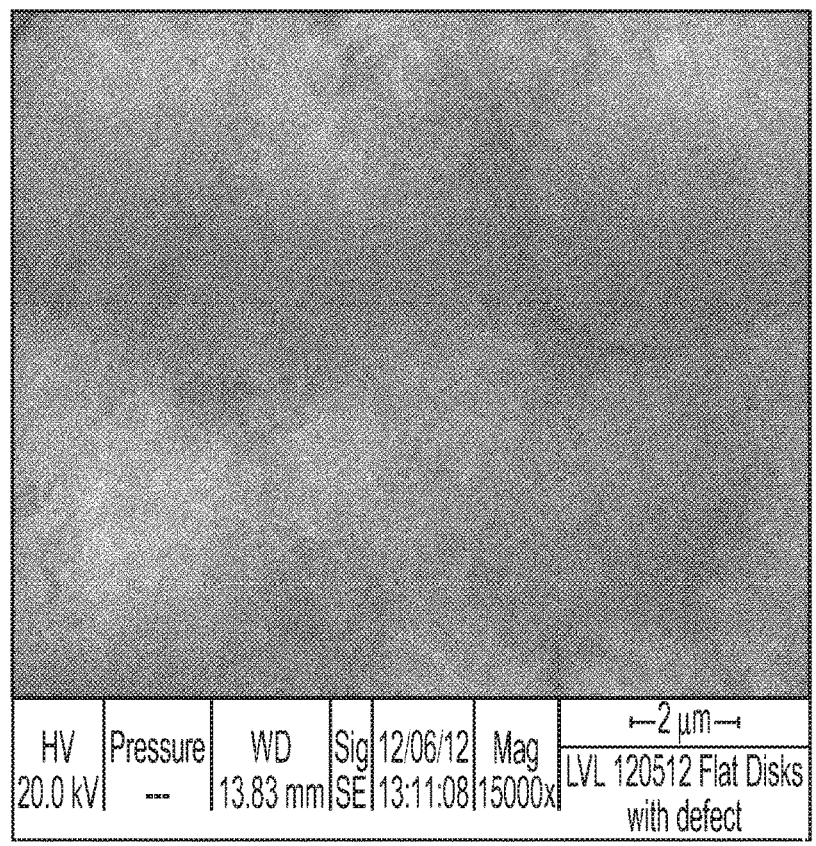
FIG. 8 is an SEM image of a SoDHA coating at 15000× magnification.
Figure 9A:
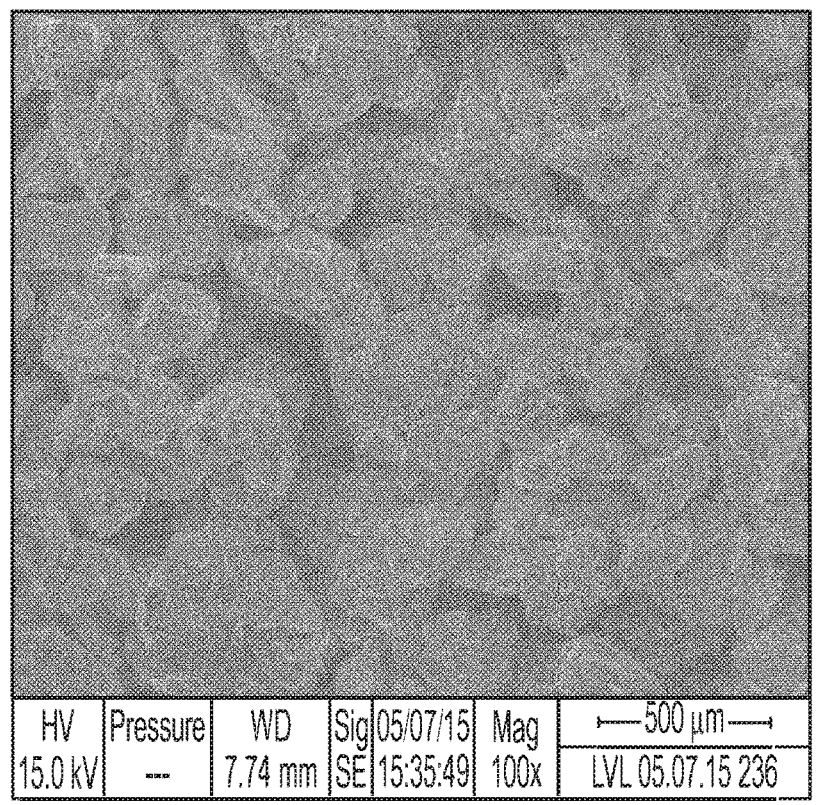
FIG. 9A is an SEM image of a SoDHA coating at 100× magnification.
Figure 9B:
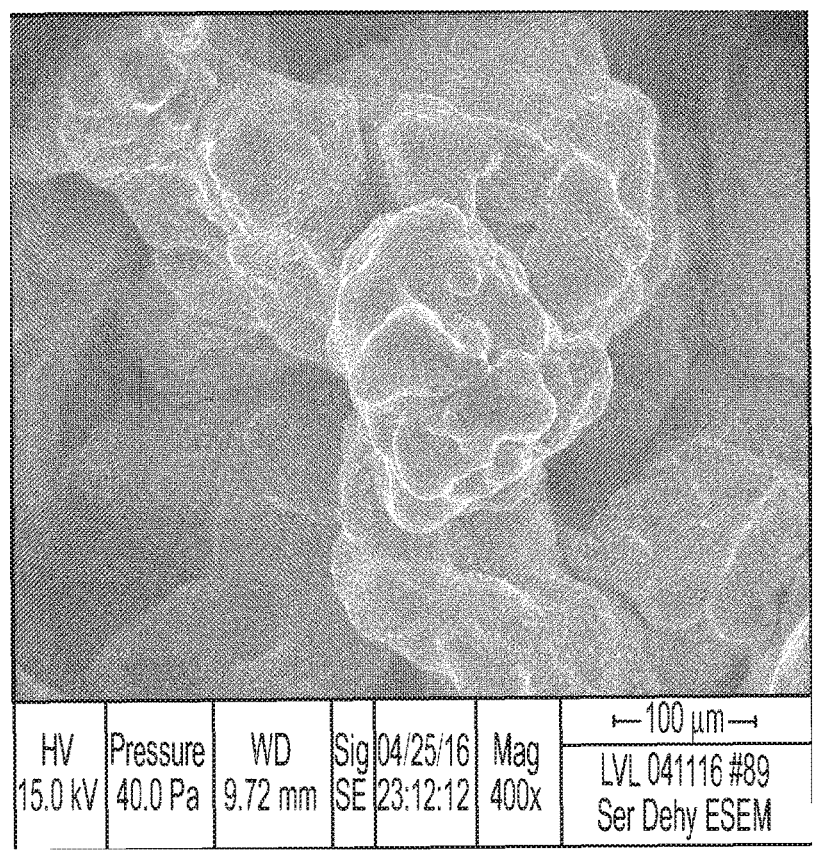
FIG. 9B is an SEM image of a SoDHA coating at 400× magnification.

FIG. 8 shows a scanning electron microscope (SEM) image of SoDHA HA coated flat titanium disc at 15000× magnification. FIGS. 9A and 9B show scanning electron microscope (SEM) images of a SoDHA HA coated porous ingrowth structure (Gription) at 100× and 400× magnification, respectively. It is seen the HA coating was continuous over the disc surface.

FIG. 11 shows the effect of substrates having various surface area (mm$^2$) on deposition rate (mg/hr) at fixed dG, temperature, and degree of agitation. Materials were coated with HA at nominal values in the full scale deposition system, using nominal conditions as described in Example 5. It can be seen that coating rate decreased as surface area increased. This trend may be utilized to estimate coating time based on surface area for a given substrate.

The density of bulk HA and OCP are similar at about 3.1 g/cm$^3$. Deposits of HA prepared at nominal values according to Example 5 weighed 7 mgs on flat coupons, had a surface area of 5.07 cm$^2$, and had a thickness of about 7 microns, corresponding to an actual density of about 1.97 g/cm$^3$ and a porosity of about 36%.

Example 9: Full Scale Process Characterization

The coating prepared according to the full scale system process of Example 5 at nominal and process limit values met the following specifications:
Coating weight: 0.08 to 0.12 mg/mm$^2$ of projected surface area
% crystalline HA by Rietveld analysis: >70%
% of amorphous calcium phosphate: <detection limit by DSC, as described in Example 11.
XRD crystallite size parameters:
1/β (200) 1.63+−0.13
1/β (002) 4.15+−0.10
1/β (210) 1.5+−0.10
Tensile adhesion as determined according to ASTM F1147 (measured on grit blasted flat): >68 MPa Ca/P ratio: 1.39 to 1.65

FIGS. 12-16 summarize data obtained from the full scale system evaluated at nominal and process limit conditions. In all cases, the error bars are equal to 3 standard deviations of the data.

Figure 12:
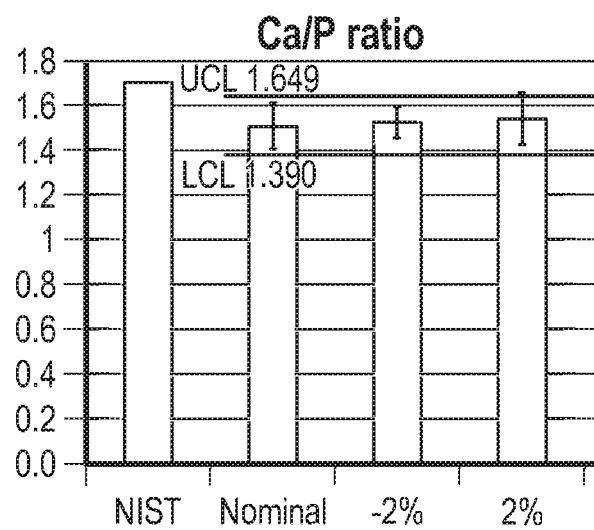
FIG. 12 is a chart showing the Ca/P ratios of five samples created according to the SoDHA process in the full scale deposition system shown in FIG. 7.

FIG. 12 shows the Ca/P ratio for HA coated materials prepared by deposition in the full scale system according to Example 6 at nominal and process limits. Ca/P ratio was determined by wet chemical methods. "NIST" refers to National Institute of Standards and Technology standard hydroxyapatite.

Figure 13:
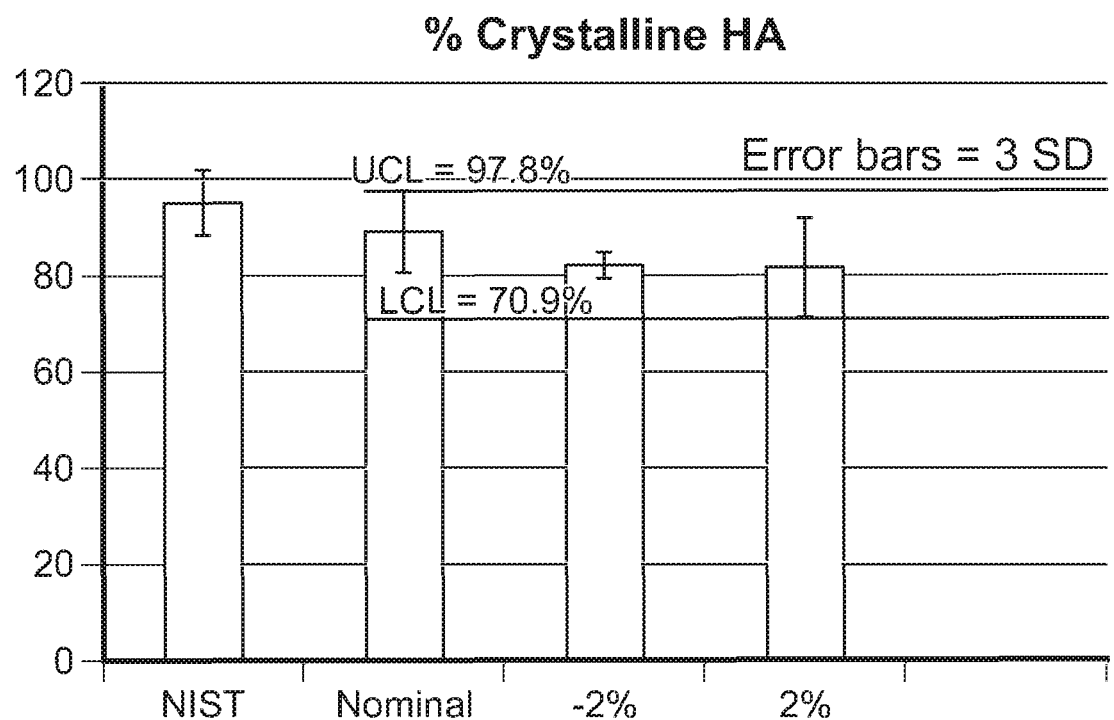
FIG. 13 is a chart showing the crystallinity of the hydroxyapatite in the five samples described in FIG. 12.

FIG. 13 shows the crystallinity of the coatings as determined by XRD for HA coated materials prepared by deposition in the full scale system according to Example 6 at nominal and process limits. Crystallinity was determined based on areas under selected diffraction peaks on the coating and compared to the same peak areas on the highly crystalline NIST standard. The balance of material not reported is not amorphous as found in PSHA deposits. Crystallinity values less than 100% reflect the fine grain size of the films and the fact that grain boundaries are disordered and do not contribute much to diffracted peak areas. Amorphous content is determined by DSC.

Figure 14:
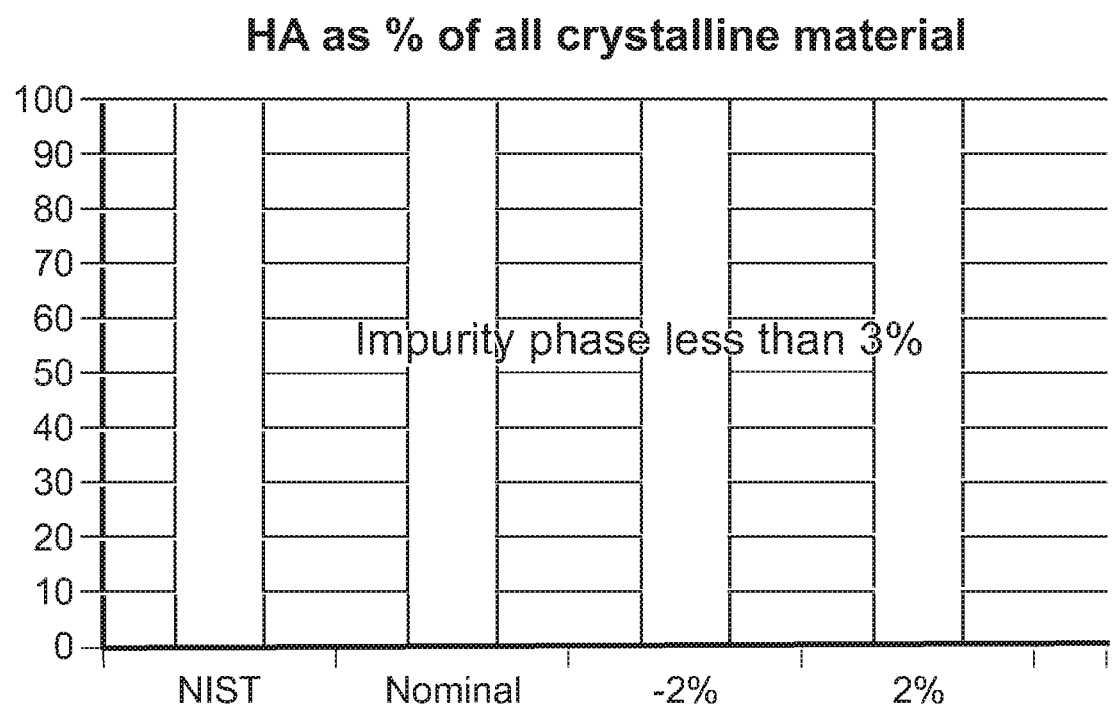
FIG. 14 is a chart showing the percentage of crystalline hydroxyapatite in the materials formed by the SoDHA process in the five samples described in FIG. 12.

FIG. 14 shows the percentage of HA as crystalline material out of all crystalline material in the HA coated substrates prepared by deposition in the full scale system according to Example 6. In other words, it is a measure of the phase purity of the films.

Figure 15:
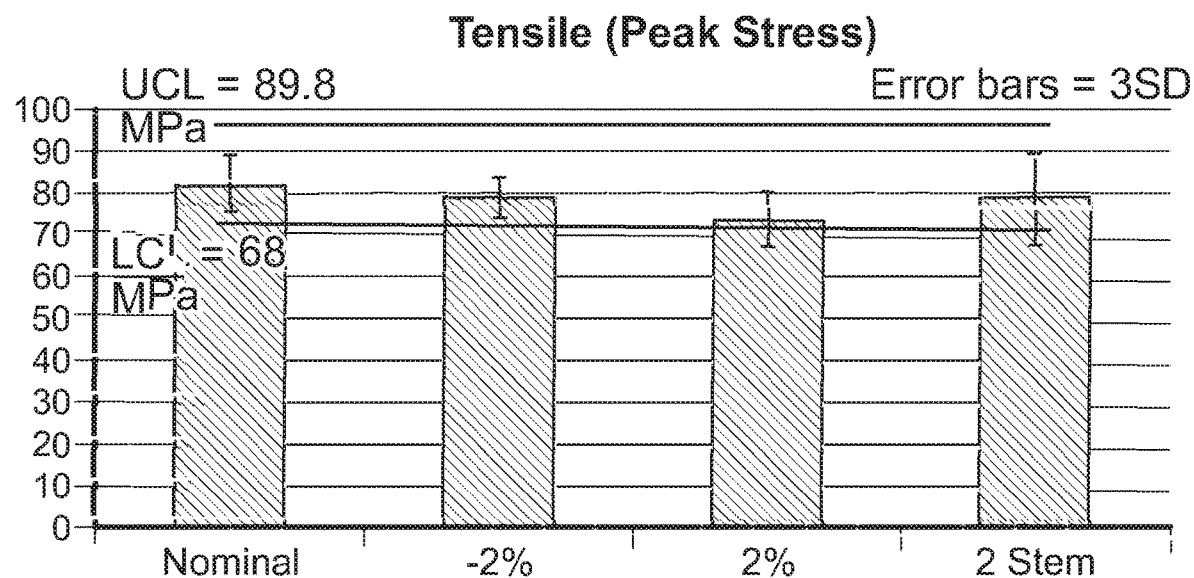
FIG. 15 is a chart showing the tensile strength of the hydroxyapatite in the five samples described in FIG. 12.

FIG. 15 shows tensile adhesion as determined by ASTM F1147 of HA films prepared by deposition in the full scale system according to Example 6.

Figure 16:
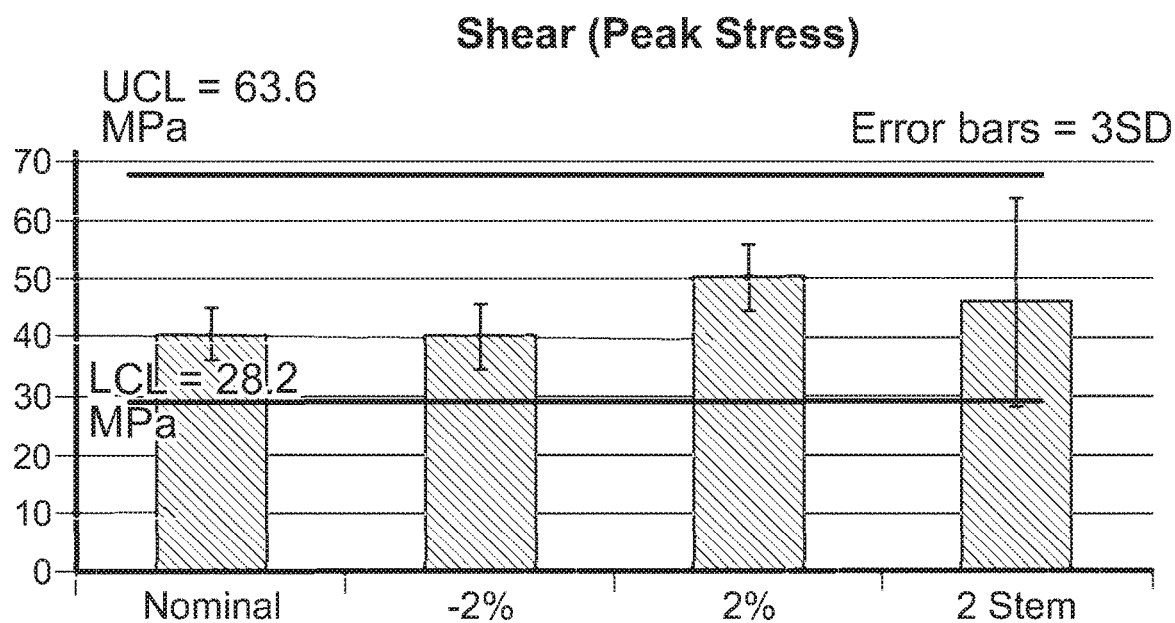
FIG. 16 is a chart showing the shear strength of the hydroxyapatite in the five samples described in FIG. 12.

FIG. 16 shows shear adhesion as determined by ASTM F1044 of HA films prepared by deposition in the full scale system according to Example 6.

Example 10—Differential Scanning Calorimetry (DSC)

Differential Scanning calorimetry (DSC) has been previously investigated to directly observe, and qualitatively measure, the thermal recrystallization of amorphous calcium phosphate phases in plasma sprayed hydroxyapatite materials. It has been reported that amorphous calcium phosphate recrystallizes by a series of exothermic reactions that occur at different temperatures (within the range of 500° C. and 750° C.) and with different amplitudes dependent upon changes in the plasma spraying parameters (e.g. plasma power, feed rate, coating thickness etc.). Reactions are seen by the exothermic peak at approximately 500-550° C. (the crystallization of hydroxyl-rich amorphous regions in the material), the exothermic peak at approximately 600-650° C. (the diffusion of hydroxyl ions into hydroxyl-depleted regions), and the exothermic peak approximately 720-750° C. (crystallization of oxyapatite phase).

In this example, DSC was used to observe any phase transitions (e.g. recrystallization) that can occur in hydroxyapatite/calcium phosphate materials as a consequence of impurities and/or amorphous phases on heating up to 725° C.

Solution deposited SoDHA HA powders prepared according to Example 5 were scraped from flat Ti64 witness coupons. Each powder material was tested a minimum of 3 times using the DSC. The Pyris DSC analysis software was used to measure the peak areas and peak positions (between 550 and 710° C.) for all powder samples, and the resulting recrystallization energies (J/g) were calculated.

Figure 24:
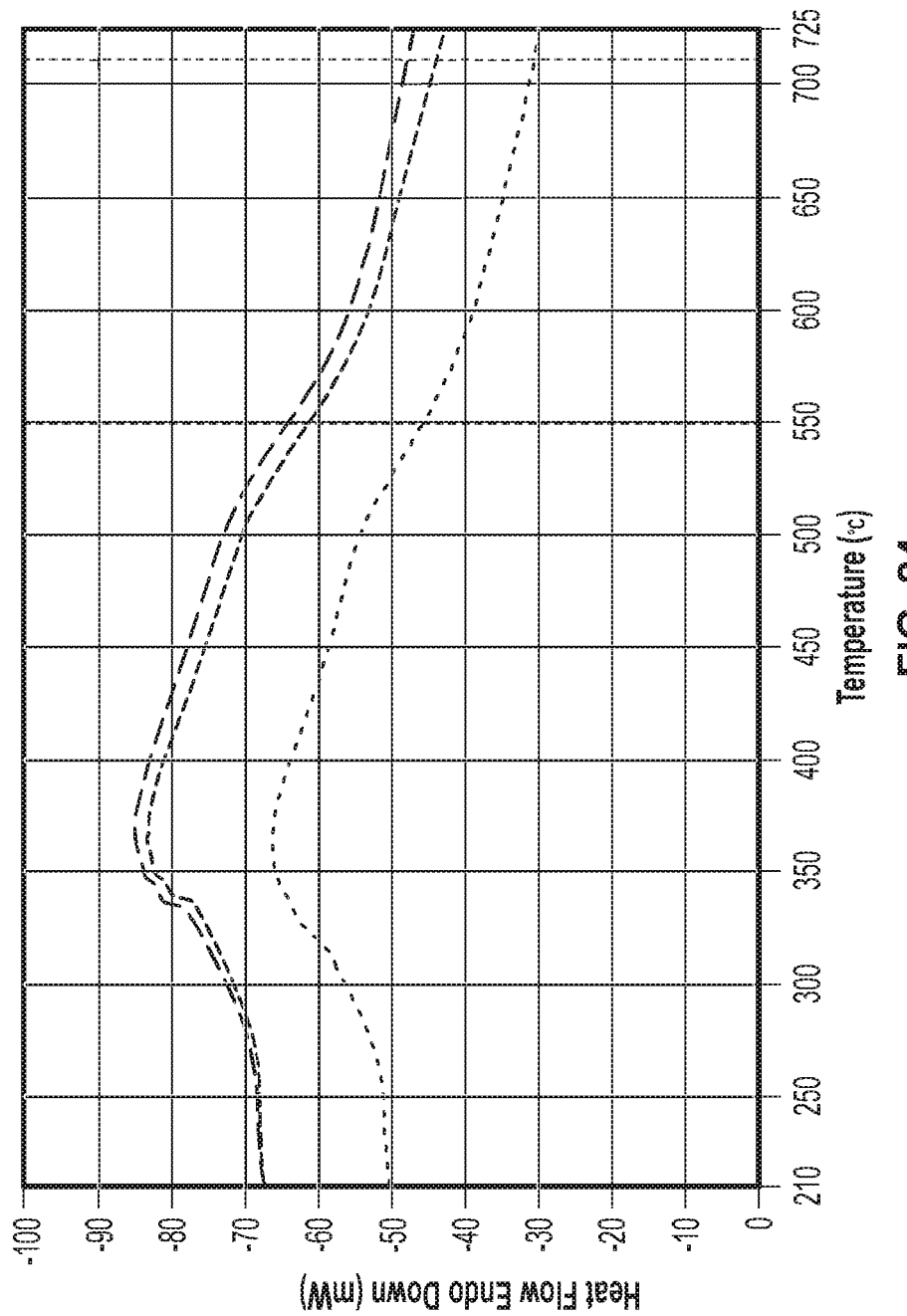
FIG. 24 shows DSC traces from scraped SoDHA powders showing no discernible exothermic peaks on heating.

DSC analysis of SoDHA powders scraped from coated Ti witness coupons is shown in FIG. 24, which shows no discernible exothermic peaks on heating.

In the area of interest, i.e. 550° C. and 710° C., there were no exothermic peaks seen in the DSC heating curves generated for scraped SoDHA powders, indicating very little, if any, glassy amorphous phases. Based on the DSC curves, there was less than 2 wt % glassy amorphous material in the SoDHA powders tested. It was also observed that the SoDHA powders analyzed using DSC were a gray color coming out of the test, indicating a small amount of titanium is removed from the substrates on scraping and subsequently oxidizes during DSC testing.

Example 11: First Gallium-Substituted SoDHA Coating Trial

Gallium doping studies began by adding gallium ions to the calcium stock solution. The process described in Example 6 was repeated, except the gallium/calcium solution was used instead of the calcium solution. This method destabilized the deposition process, and gallium found in films formed in this manner was present as a separate phase. Turbidity was observed at various time intervals following gallium nitrate addition to the calcium stock solution. This was reflected in low coating efficiency, and gallium detected in coatings produced in this manner was present as discrete gallium bearing particles. There was a considerable amount of loosely bound calcium phosphate precipitate on the surface of the desired SoDHA coating.

Example 12: Gallium-Substituted SoDHA Coating

The process described in Example 6 was repeated, except as follows. The gallium/phosphate solution was used instead of the phosphate solution. 500 mL of the calcium solution was added to the gallium/phosphate solution. The pH at the start of these experiments was typically between 7.68-7.8.

Surprisingly, gallium was incorporated into the HA lattice by adding gallium to the stock solution containing phosphate and TRIS and NaCl. This incorporation is demonstrated by data showing a gallium dose dependent shift in lattice parameter, crystallite size, and BET surface area, as further described in Example 9. Gallium-substituted SoDHA coating trials indicate that addition of Ga-salt $(Ga(NO_3)_3)$ in Tris buffered phosphate(Pi)-stock was produced with coating efficiencies amenable to heterogeneously coating a test article without solution turbidity.

The process was repeated using a "full scale" system in the coating vessel shown in FIG. 7. In the full scale system, 40 acetabular cups were placed in 64 L of the supersaturated solution.

Example 13: Ga-substituted HA Coating XRD Characterization

In this example, the gallium-substituted HA coatings prepared by deposition in the full scale system according to Example 12 were characterized by XRD.

Six coated discs, representative of 0 wt %, 5 wt %, 10 wt %, 15 wt % and 20 wt % Ga in HA lattice added to the coating solution, were analyzed by X-ray diffraction (XRD) spectroscopy.

Scraped gallium-substituted HA powders were analyzed by powder XRD (and the associated Rietveld and FWHM analyses). Care was taken to scrape the coated HA material down to the Ti substrate without generating Ti contamination in the powder. Due to the relatively low mass (4-9 mg) of powder on each of the coated flat substrates, 6 substrates were scraped to obtain 15-20 mg of gallium-substituted HA powder. XRD scans for the as coated gallium-substituted HA discs were measured with the background calculated and removed using Panalytical X'Pert software.

Figure 18:
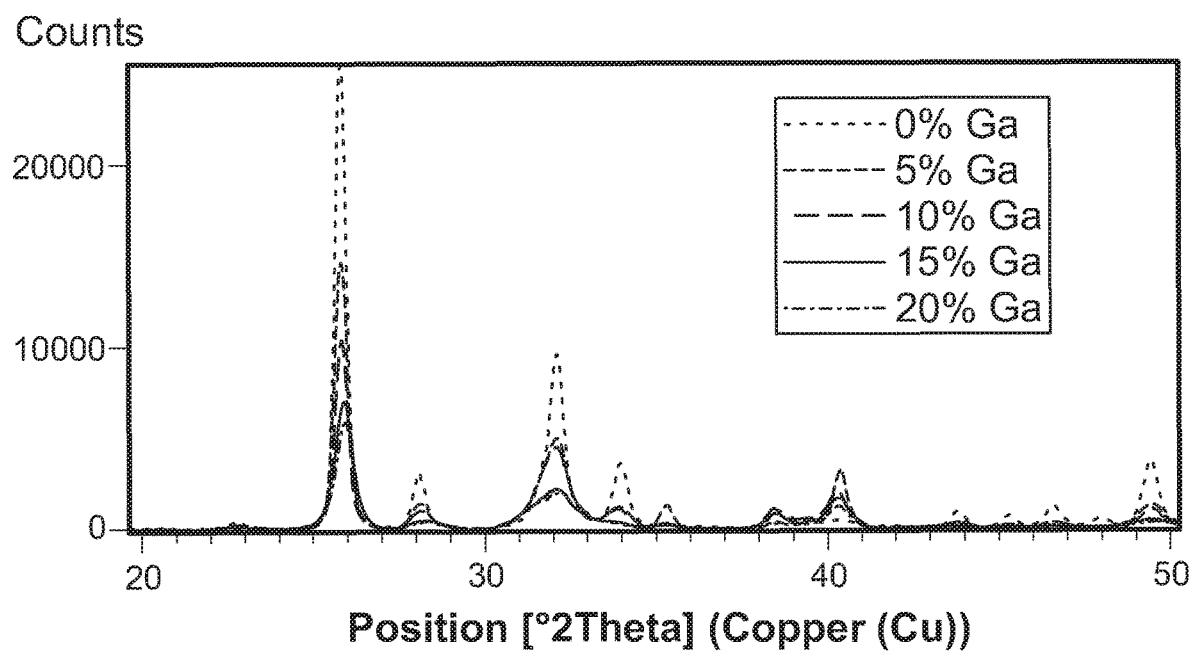
FIG. 18 shows superimposed XRD scans for as coated gallium-substituted SoDHA HA discs for 0 wt % to 20 wt % Ga solution conditions.
Figure 19:
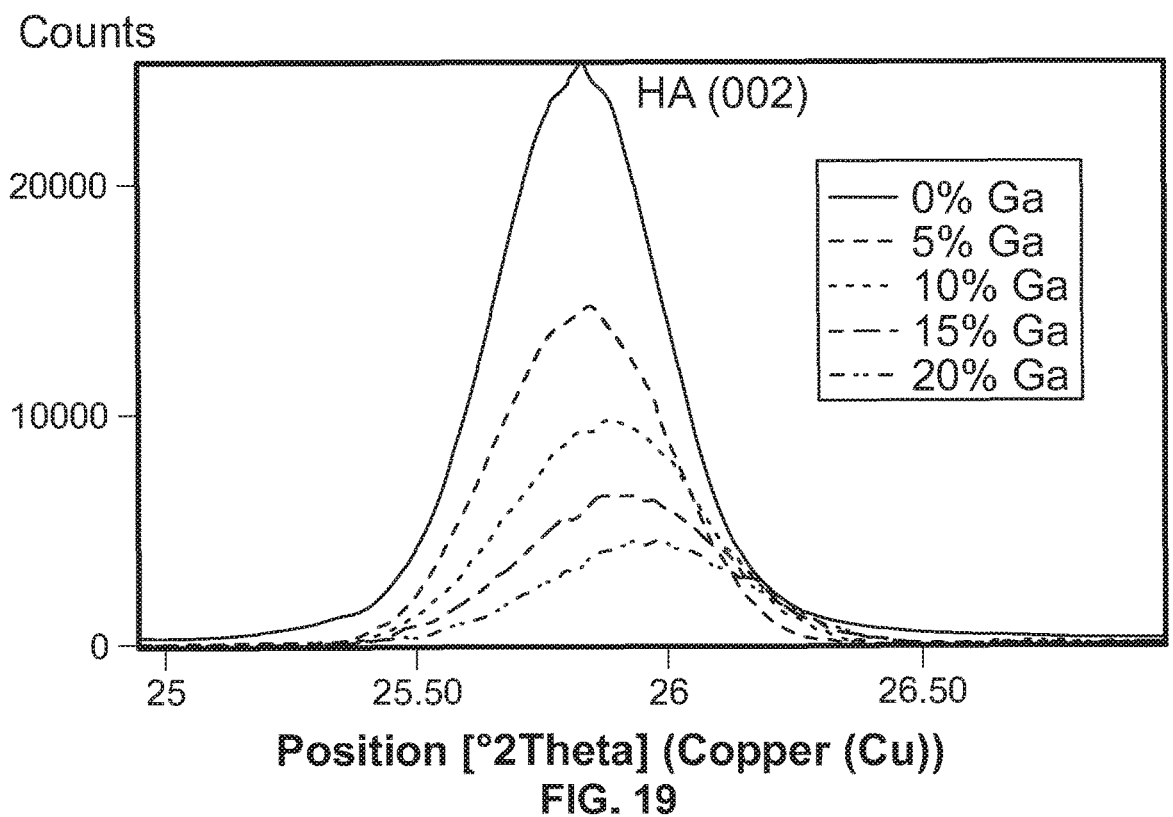
FIG. 19 shows 25° to 27° 2θ of the superimposed XRD scans of FIG. 18.

An overlay of the XRD plots is shown in FIG. 18, which indicates that the gallium-substituted HA coatings were phase pure, within the detection limits of the X-ray equipment (no XRD peaks associated with second phases were observed), and the HA coating was highly textured in the 001 crystal orientation.

For the sample with 20 wt % gallium, Table 3 shows 2θ values, together with the relative intensities of various peaks, as determined using XRD of the gallium-substituted HA samples. Background was calculated and removed using Panalytical X'Pert software. The relative intensity of each the peak was calculated as a percentage of the most intense peak in the scan. It is noted that not all peaks published in the NIST SRM data for HA were observed in the as coated gallium-substituted HA coating due to preferred orientation in the coating. It also is noted that the 100% intensity peak in a randomly oriented HA powder is the (211) peak, occurring at 31.70° 2θ, whereas the 100% intensity peak observed for as coated gallium-substituted HA discs is the (002) peak occurring at about 25.95° 2θ. The increased intensity of the (002) peak indicates highly oriented crystals in the 001 direction.

TABLE 3

XRD peak spacing and intensity for 20 wt % gallium-substituted HA

| d-spacing | 2θ | Relative intensity (%) |
|---|---|---|
| 002 | 25.95 ± 0.02 | 100 |
| 211 | 31.70 ± 0.02 | 45-46 |
| 112 | 32.21 ± 0.02 | 47-48 |
| 202 | 34.09 ± 0.02 | 21-22 |
| 213 | 49.61 ± 0.02 | 14.5-15.5 |
| 004 | 53.37 ± 0.02 | 18-19 |

As shown in FIG. 18, as the wt % Ga was increased, a reduction in the HA crystalline phase content was observed. This is noted from reduced peak intensities in the XRD traces as wt % Ga is increased. It is also noted that a systematic shift in the (002) peak was seen to higher 2θ angles (corresponding to decreases in d-spacing) as the Ga was increased in the gallium-substituted SoDHA coatings. Table 4 shows the average HA (002) peak positions measured from the coated discs formed from solutions with varying concentrations of gallium. The progressive decrease in lattice d-spacing is consistent with smaller Ga' ions (0.62 Å) substituting into the Ca1 lattice site in the HA lattice for larger Ca' ions (0.99 Å).

TABLE 4

Average and standard deviation of gallium-substituted HA (002) XRD peak spacing at varying gallium concentrations

| wt % Ga in Solution | (002) d-spacing (Å) | |
|---|---|---|
| | Ave | Std. Dev. |
| 0% | 3.4506 | 0.0006 |
| 5% | 3.4491 | 0.0016 |
| 10% | 3.4456 | 0.0013 |
| 15% | 3.4400 | 0.0016 |
| 20% | 3.4348 | 0.0011 |

The analysis of the (002) peak shifts confirms the observations from as coated discs, that (002) d-spacing decreases as wt % Ga is increased in the SoDHA coating. This is consistent with increasing Ga substitution of Ca1 sites in the HA lattice. These data reveal that gallium was successfully substituted into the lattice of hydroxyapatite.

Example 14—Additional Gallium-Substituted HA Coating Results

Figure 20:
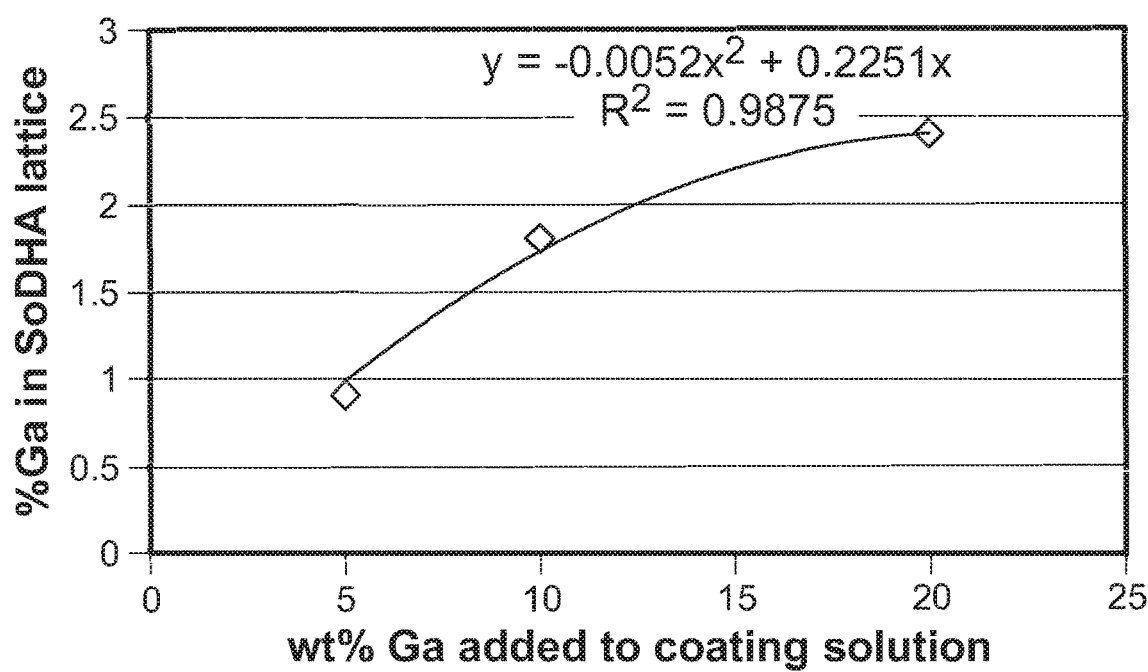
FIG. 20 shows % Ga in gallium-substituted SoDHA HA discs formed at 0 wt. % to 20 wt. % Ga solution conditions.

The wt % of gallium in the SoDHA lattice was determined for gallium-substituted HA coatings formed according to Example 12 from solutions having 5 wt %, 10 wt %, and 20 wt % gallium nitrate, as shown in FIG. 20.

Results presented in Table 5 show the amounts of crystalline hydroxyapatite, amorphous and disordered crystalline content in gallium-substituted hydroxyapatite samples formed from solutions with varying amounts of Ga according to Example 12.

TABLE 5

Average wt % crystalline and amorphous content in gallium-substituted HA at varying gallium concentrations

| wt % Ga in Solution | Average wt. % Crystalline HA | Average wt. % Amorphous/ Disordered Crystalline |
|---|---|---|
| 0% Ga | 91.7 | 8.2 |
| 5% Ga | 74.5 | 25.4 |
| 10% Ga | 64.8 | 33.0 |
| 15% Ga | 53.1 | 46.9 |
| 20% Ga | 38.7 | 61.2 |

As shown in Table 6, it is seen from FWHM analyses that the average crystallite size in the (200), (002) and (210) directions are reduced considerably as Ga is introduced into the HA lattice. Average crystallite size in the (200), (002) and (210) directions is shown in Table 7. It is noted that the crystallite size in the (200) direction becomes too small to measure after just 10 wt % Ga addition. Without intending to be bound by theory, it is proposed that crystallite size reduction in the HA coating is the primary reason for the calculated decrease in crystallinity from the Reitveld analyses due to the peak broadening associated with the very small crystal sizes.

TABLE 6

Average 1/β of gallium-substituted HA XRD peaks at varying gallium concentrations

| wt % Ga in Solution | 1/β HA (200) | 1/β HA (002) | 1/β HA (210) |
|---|---|---|---|
| 0% Ga | 2.51 | 6.50 | 1.67 |
| 5% Ga | 2.10 | 3.34 | 1.52 |
| 10% Ga | 1.38 | 2.32 | 1.23 |
| 15% Ga | — | 1.82 | 0.92 |
| 20% Ga | — | 1.49 | 0.64 |

TABLE 7

Average crystallite size (τ) of gallium-substituted HA XRD peaks at varying gallium concentrations

| wt % Ga in Solution | τ HA (200) (nm) | τ HA (002) (nm) | τ HA (210) (nm) |
|---|---|---|---|
| NIST SRM 2910a (Measured) | 38.72 | 82.07 | 119.58 |
| NIST SRM 2910a (Reported) | 36.26 | 81.76 | 130.09 |
| Nominal | 20.50 | 68.61 | 49.19 |
| 5% Ga | 17.11 | 35.27 | 44.85 |
| 10% Ga | 11.28 | 24.45 | 36.15 |
| 15% Ga | Not Measurable | 19.16 | 27.14 |
| 20% Ga | Not Measurable | 15.75 | 18.89 |

Example 15—FTIR Characterization

Figure 21:
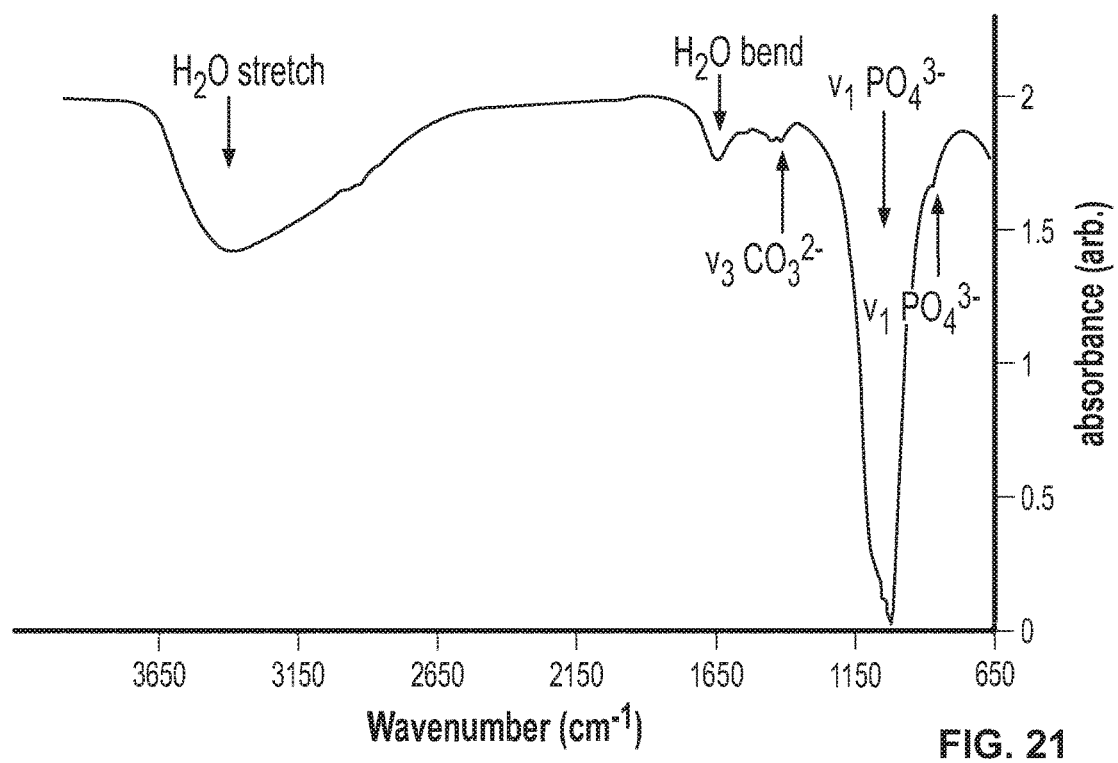
FIG. 21 shows a Fourier transform infrared spectroscopy (FTIR) spectrum of a scraped SoDHA-G HA powder.

An FTIR spectrum was obtained of the gallium-substituted SoDHA HA formed in Example 12. The FTIR spectrum is shown in FIG. 21.

Example 16—Dissolution

Figure 22:
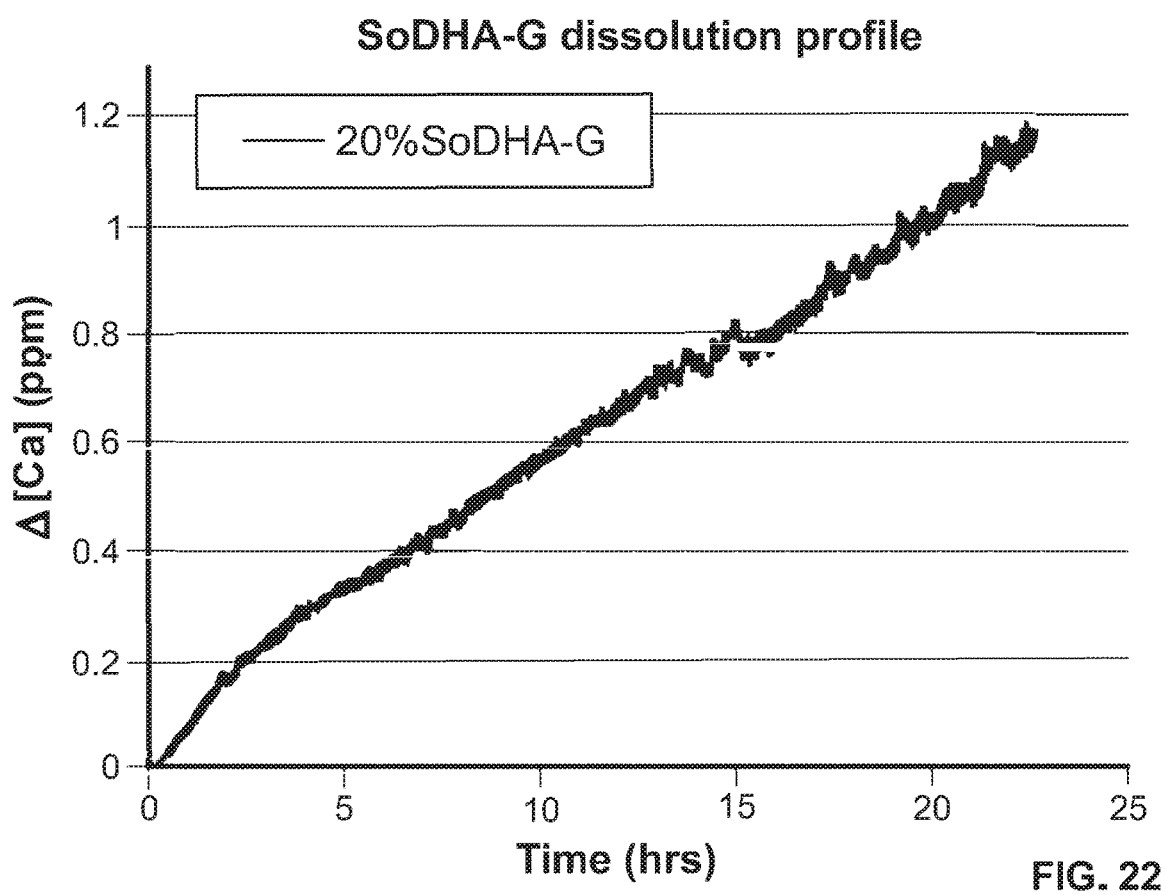
FIG. 22 is a chart showing the dissolution rate of a gallium-substituted SoDHA HA sample.
Figure 23:
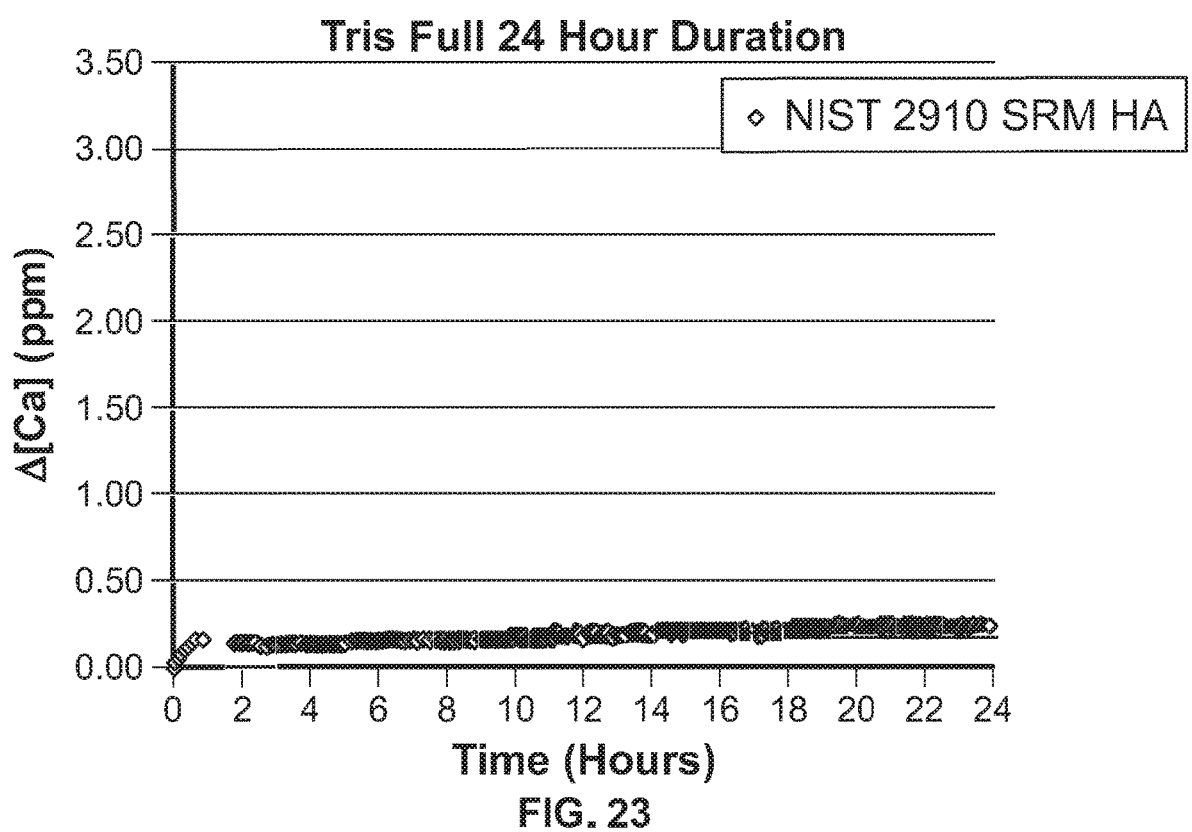
FIG. 23 is a chart showing the dissolution rate of a National Institute of Standards and Technology (NIST) standard HA sample.

Dissolution rates of the gallium-substituted SoDHA coating formed in Example 12 and of a NIST hydroxyapatite reference material were determined by placing the samples in a tris buffered saline solutions at pH 7.4 and measuring change in calcium concentration. FIG. 22 shows the dissolution results for the gallium-substituted SoDHA coating, and FIG. 23 shows the dissolution results for the NIST standard. While the NIST sample stopped releasing calcium after less than two hours, the gallium-substituted SoDHA sample released calcium for more than 20 hours with no clear dissolution plateau.

Example 17—Canine Study

The goal of this preclinical study was to determine the bone response to a gallium doped hydroxyapatite coating for orthopedic implants. Implants were placed at either line-to-line fit or as gap-fit in trabecular sites in dogs. Tissue was harvested 6 weeks after surgery. The outcome measures were implant fixation (measured via destructive mechanical testing), bone ongrowth and bone ingrowth (measured via backscattered scanning electron microscopy and histology) and new bone fill within the gap (measured via histology). Secondary measures included descriptive histology to report the tissue response around implants, and quantification of the % residual gallium-substituted HA coating.

Implants were placed in cylindrical defects created in the cancellous bone of large, skeletally mature, mixed-breed hounds. A canine was selected as a model for testing as the bone structure of canines closely resembles human bone. The sites of implantation selected for this study provide a large volume of cancellous bone. A total of 5 dogs were enrolled in this study. Five purpose-bred research hounds (22-27 kg) were used in this study. Skeletal maturity was confirmed by X-ray evidence of closed growth plates. The dogs were acclimated for a period of at least two weeks prior to surgery. Animals were single-housed throughout the study period. All five dogs were deemed healthy upon arrival and. examination by the attending veterinarian prior to surgery revealed no obvious abnormalities.

The effects of these coatings on implant fixation were assessed in both 1 mm gap and line-to-line or exact fits, as they represent a range of implant to host bone fit scenarios that are encountered in total joint replacement procedures in humans. Four defects per animal were created in cancellous bone to create side-by-side regions with line-to-line and 1 mm radial gap fits between the porous coated surface of 6 mm diameter implants and the host bone. These defects were created bilaterally in the proximal humerus, distal femur, and proximal tibia. Two additional defects per animal were created in cancellous bone distal to the first defect in the humerus, bilaterally, in order to place a single implant with a 1 mm radial gap fit. This was done due to the limitation on the number of anatomical sites suitable for implantation of side by side implants in this model.

The following test articles were used:

Gription™ implants with SoDHA HA coating (HA version of the SoDHA coating)—10 mm length and 11 mm length, 6 mm (line-to-line implant) or 8 mm diameter (1 mm gap implant).

Gription™ with gallium-substituted SoDHA HA coating (gallium-substituted HA version of the SoDHA coating)— 10 mm length and 11 mm length, 6 mm (line-to-line implant) or 8 mm diameter (1 mm gap implant).

All of the experimental work in this study w reviewed and approved by the local institutional animal care and use committee (protocol #2008A0083-R2, approved Jun. 23, 2014). The animals in this study were handled and maintained in accordance with the requirements of the Animal Welfare Act.

Dogs were housed in cages with stainless steel runs, and approximately 24 square feet of floor space. Floors were elevated with vinyl coated expanded mesh floors that were removable for sanitation. Cages were hosed clean at least once daily or more frequently as needed to prevent accumulation of excreta. Animals may have remained in place during daily cleaning with measures taken to assure that the animals remained dry. All cleaning or disinfecting agents used in the vivarium were designated as USDA "Food Safe" and approved for use by the Attending Veterinarian.

Sanitation of cages and holding rooms was performed using a pressure washer or other approved agent every 2-6 weeks (frequency based on biological monitoring). Animals were removed from the cage during sanitation to prevent exposure to hot water or disinfectant solutions. All surfaces of the cage and the room were rinsed thoroughly when disinfectant solutions were used.

Dogs were fed an amount appropriate for their weight and activity according to USDA and National Research Council regulations. All feed was provided in stainless steel bowls. All animals not scheduled for a procedure were fed at least once daily. Animals scheduled for a procedure were fasted 12-24 hours before the procedure. There were no known contaminants considered to interfere with the validity of the study.

The animals on this study had free access to fresh clean water and no known contaminants considered to interfere with the validity of the study.

Animals were administered a pre-operative tranquilizer of acepromazine (0.05 mg/kg IM) and general anesthesia induced with an intravenous injection of ketamine hydrochloride and diazepam. Dogs were intubated and anesthesia maintained with an inhaled mixture of isoflurane in oxygen. The surgical plane was assessed by monitoring pulse, heart rate, respiration and reflexes (ocular, pinch). An intravenous catheter was placed in the cephalic vein and perioperative antibiotic (cefazolin) administered. Sterile isotonic fluids (LRS or similar) was delivered at maintenance doses through-out the surgical procedure. All four limbs were prepared for surgery in sequential fashion, with the hair being clipped (elbow up to the proximal scapula for the forelimb; hock up to hip for the hind limb). After initial skin preparation with surgical antiseptic, the dogs were transferred to the operating room and placed in lateral recumbency. The uppermost forelimb and hind limb were suspended from an intravenous stand with tape, and the lateral aspects of the humerus and femur were scrubbed with a combination of surgical antiseptic (povidone-iodine or chlorhexidine) and alcohol. The surgical sites were isolated with sterile drapes and an adhesive antimicrobial incise drape (Ioban 2; 3M, St. Paul, Minn.). Small incisions (<20 mm in length) were made over the lateral aspect of the proximal humerus and the distal aspect of the lateral femur, exposing the metaphyseal regions of each bone. Guide wires were placed using a drill, and fluoroscopy used to confirm that the guide wires were oriented into the trabecular bone at 90 degrees to the cortical surface. A cannulated drill bit was then used to drill a hole that is 6 mm in diameter and 20 mm in overall length. The proximal half of the drill hole was over-drilled to a final diameter of 8 mm. The same procedure was used in both the humerus and femur. A total of four implants were placed—a 6 mm implant inserted into each defect and seated fully into the distal one-half of the drill hole using a custom impactor. An 8-mm implant (consisting of a 6-mm core diameter implant with 8-mm washers at each end) was then placed into the drill hole and seated fully. In this way, each bone defect contained one implant with a line-to-line fit at the implant-bone interface, and one implant with a circumferential 1-mm gap between the gallium-substituted HA-coated implant and the surrounding bone. Following placement of the humeral and femoral implants, the skin incision was closed with subcuticular resorbable sutures (Monocryl, PDS II or similar) and the repair reinforced with skin staples. The wounds were covered with adhesive dressings, the dogs rolled onto the opposite site, the skin scrubbed, and the implants placed using exactly the same procedures as described for the first side. After placement of the humeral and femoral implants, the skin over the medial aspects of the left and right tibia was scrubbed with a combination of surgical antiseptic (povidone-iodine or chlorhexidine) and alcohol. The surgical sites were isolated with sterile drapes and an adhesive antimicrobial incise drape (Ioban 2; 3M, St. Paul, Minn.). Small incisions (<20 mm in length) were made over the medial tibial metaphysis. A guide-wire was placed as before, and a single drill hole (6 mm in diameter, 10 mm in length) made into the cancellous bone, at right angles to the medial tibial cortex. A 6 mm implant, was placed in line-to-line fit, and the subcutis and skin closed as described previously. Following surgery, the dogs were monitored closed until recovered from anesthesia. The endotracheal tube was removed when the dog regained its swallow reflex. Any IV catheters were removed at this time. Post-operative pain management included an opiate analgesic (buprenorphine) every 6-12 hours for 3 days post-operatively. Non-steroidal anti-inflammatory agents (carprofen or meloxicam) and antibiotics (cephalexin) were administered on the first post-operative morning and continued for 7-10 days post-surgery. Study team members monitored the dogs at least twice daily until skin staples were removed at 10-14 days post-surgery.

At the designated time point, dogs were euthanized with an intravenous overdose of sodium pentobarbitone and death confirmed by an absence of cardiorespiratory activity. The surgical sites in the left and right proximal humerus, distal femur and proximal tibia were exposed, photographed and then resected with a necropsy saw, taking care to preserve the integrity of the implant and surrounding bone. Contact radiographs were made in two planes in order to document the bone response around each implant. The bone specimens were examined by micro-CT (30-µm resolution) and then packaged on ice for overnight shipment to DePuy Synthes Joint Replacement, Warsaw, Ind. Upon receipt at the Warsaw site, the specimens were bisected at right angles to the implant axis, one half was used for mechanical testing at DePuy Synthes, and the other half was placed in 70% alcohol and returned to The Ohio State University for undecalcified histology.

Example 18—Histology Results

Undecalcified histology was carried out with fixed specimens of the implant-bone interface processed by the Technovit 7200 and sectioned at right angles to the implant axis using a diamond band saw. A custom alignment jig was used to ensure accurate implant alignment and sectioning. Two sections were prepared from each implant. These sections were ground to a final thickness of 100-150 µm, polished and then surface stained with Goldner's trichrome. The nature and extent of bone contact, fibrous tissue formation and periprosthetic inflammation were described.

Embedded blocks containing the implant-bone interface were polished, coated with graphite and examined using backscattered SEM. Grayscale images were obtained across the entire perimeter of the implant, and the fractional percentage of bone apposition and bone ingrowth within the implant surface was measured using semi-automated image analysis (Bioquant Osteo II). The linear extent (%) of residual HA coating on the implant surface was measured.

Figure 25:
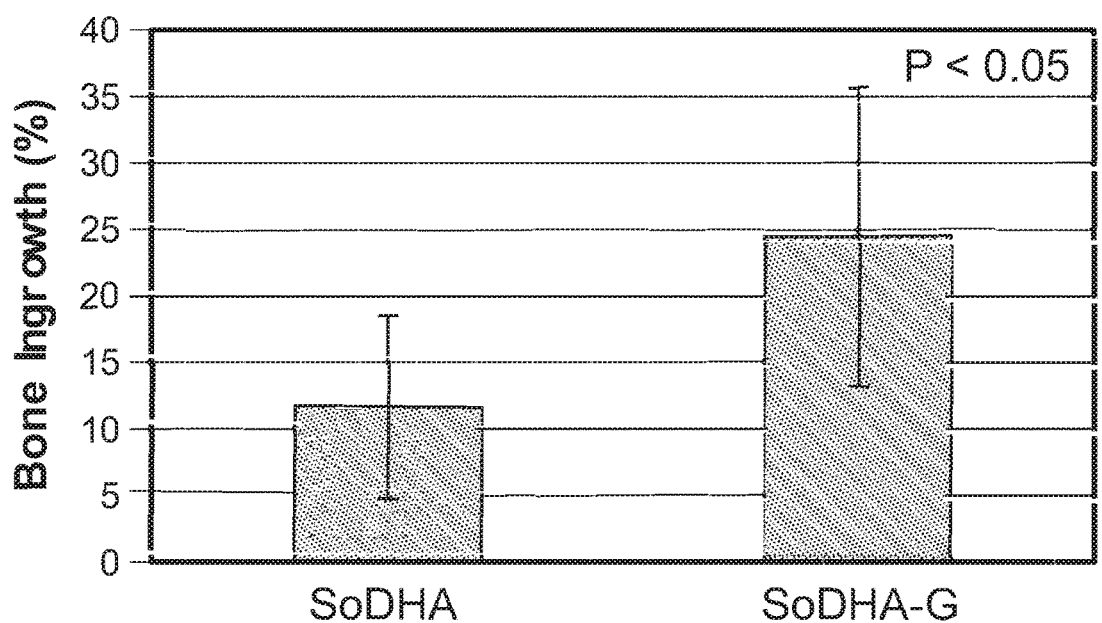
FIG. 25 shows bone ingrowth for implants having SoDHA and gallium-substituted SoDHA coatings in a canine model.

Histomorphometric analysis was performed blind to treatment on each slide. Low power digital images were captured of each section that included the gap and an additional amount of tissue surrounding each implant. Static histomorphometric analysis was completed to determine % bone apposition to the implant surface, % bone within the porous coating and % bone within the gap area. Ingrowth was measured as total voids. Additional parameters evaluated include average coating thickness. The results, averaged over the various specimens are shown in Table 8 for SoDHA HA, and gallium-substituted SoDHA HA gap implants. The data illustrating the benefit for bone ingrowth of adding Ga are also presented graphically in FIG. 25.

TABLE 8

Histomorphometry Results

| Gap implants | % Ingrowth | % Apposition |
|---|---|---|
| SoDHA | 11.6 ± 6.8 | 12.5 ± 3.6 |
| SoDHA-Gallium | 24.6 ± 11.2 | 22.6 ± 10.4 |

Histology data suggested that Gription™ SoDHA-gallium implants performed significantly (~2×) better than both Gription™ SoDHA in the upper proximal humerus. Based on a lack of inflammation, particles and radiolucency surrounding the implants, there was no adverse response to the implants or the test HA coatings detected at any of the implant sites 6 weeks after implantation.

Example 19—Organic Solvent Exchange and Supercritical $CO_2$ Solvent Extraction

Coated Gription™ and grit blast-flat coupons were rinsed with DI water after forming the SoDHA-G coating as described in Example 12. Residual aqueous solvent was exchanged with ethanol 3 times within a soaking step. Soak periods studied were 1 and 20 hours. After organic solvent exchange in ethanol, coupons were placed on a rack and inserted into a 100 ml stainless steel vessel. The coupons were covered with ethanol and the top vessel end-cap was closed. The $CO_2$ flow direction was from the top of the vessel and out the bottom. The vessel was pressurized to 100 bar with liquid $CO_2$ and the liquid ethanol was displaced with liquid $CO_2$ at room temperature at approximately 2 liters/minute of gaseous $CO_2$ flow. The displacement time was approximately ½ hour. After all the ethanol was displaced, the vessel was heated to 38° C. and dried for 4 hours with supercritical $CO_2$ at a flow rate of 5 liters/min gas. After the allotted drying time of 4 hours, the vessel was depressurized to atmosphere while maintaining the temperature above the $CO_2$ critical temperature of 32° C. The depressurization was conducted at approximately 1 liter/minute gas flow rate and lasted approximately ½ hour.

Figure 26A:
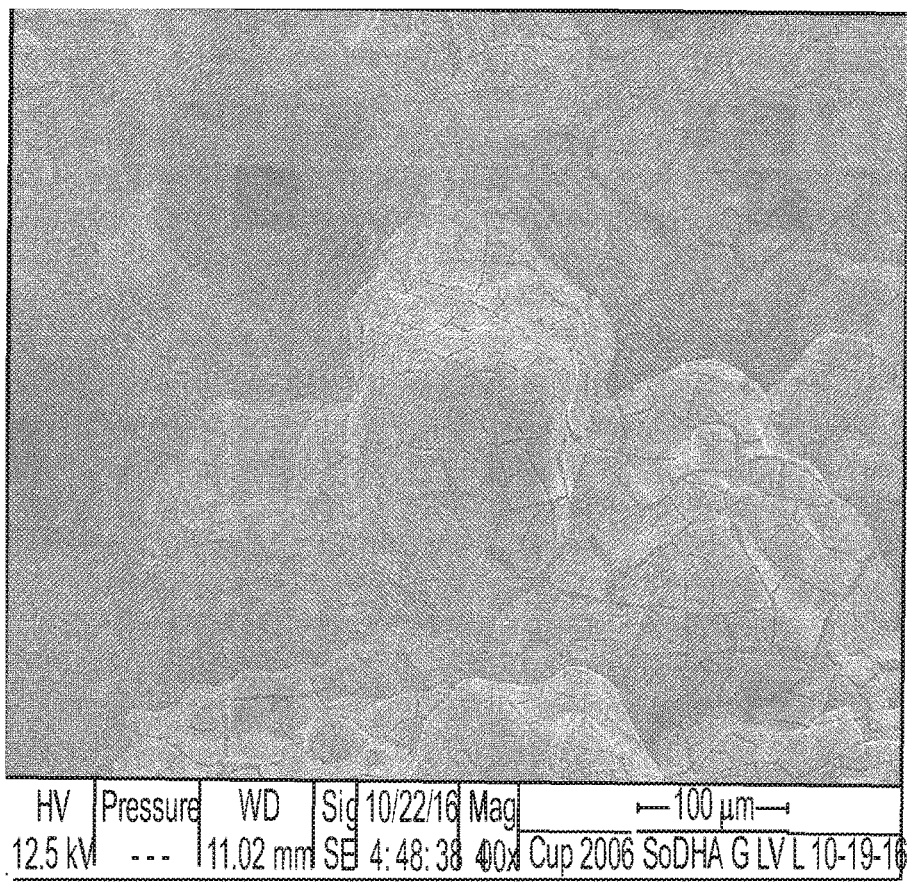
FIG. 26A is an SEM image of an air-dried gallium-substituted SoDHA coating without post-processing at 400× magnification.
Figure 26B:
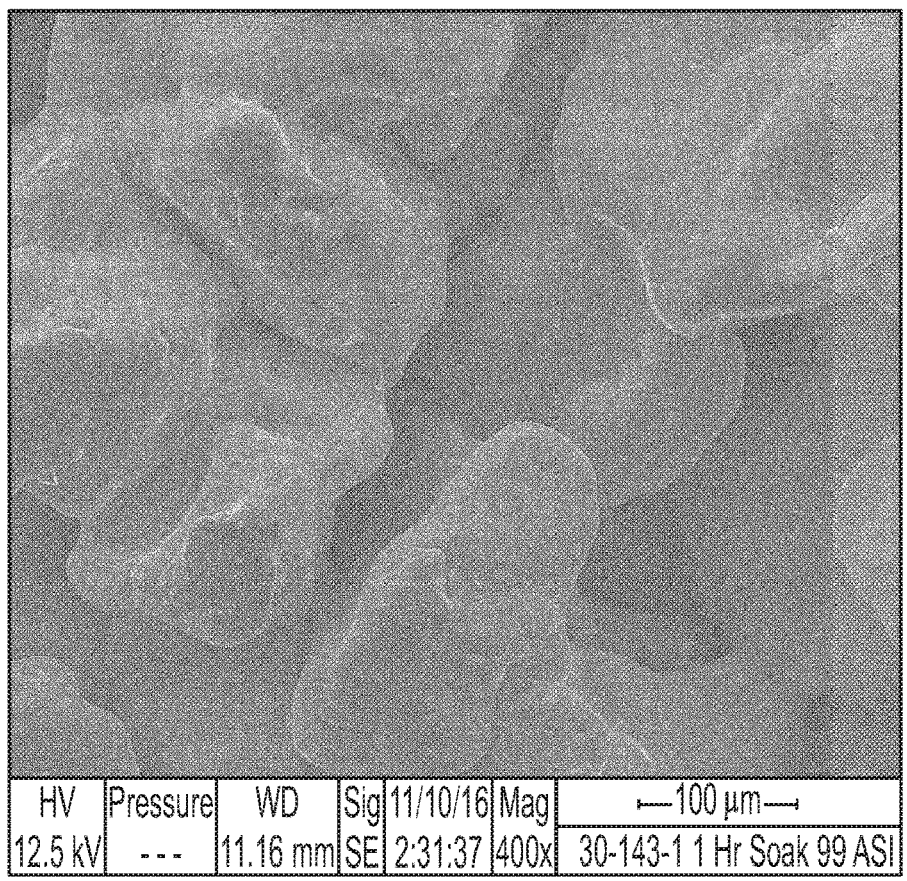
FIG. 26B is an SEM image of a scCO$_2$-dried gallium-substituted SoDHA coating at 400× magnification.

The surface morphologies of the treated and untreated films were examined by a scanning electron microscope, as shown FIGS. 26A and 26B, respectively. The scCO$_2$ treatment greatly reduced cracks in SoDHA-G coatings compared to regular drying.

Example 20—Re-Precipitation Via Hydrothermal Treatment of SoDHA-G

The SoDHA-G coated coupons prepared according to Example 12 were quickly transferred from DI water to a glass bottle containing either 15 mL 40 mM phosphate-Ga (Pi) syrup prepared according to Example 4 or 15 ml 2.2262 mM phosphate-Ga (Pi) stock prepared according to Example 4. The glass bottle was then sealed with a cap. The hydrothermal treatment of SoDHA-G films was performed at either 70° C. or 90° C. for 2 hours. After hydrothermal treatment, the SoDHA-G coated coupons were rinsed with DI water excessively for one minute and placed in a 60° C. oven to dry for 1 hour.

Figure 27:
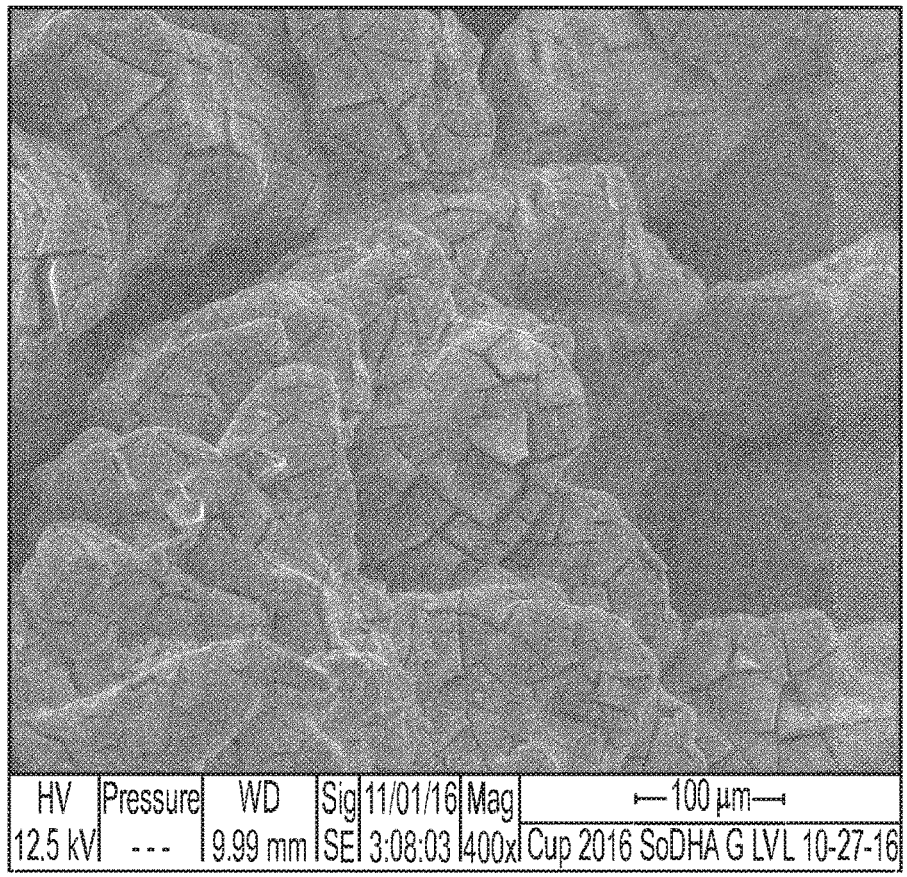
FIG. 27 is an SEM image of an oven-dried gallium-substituted SoDHA coating at 400× magnification.
Figure 28A:
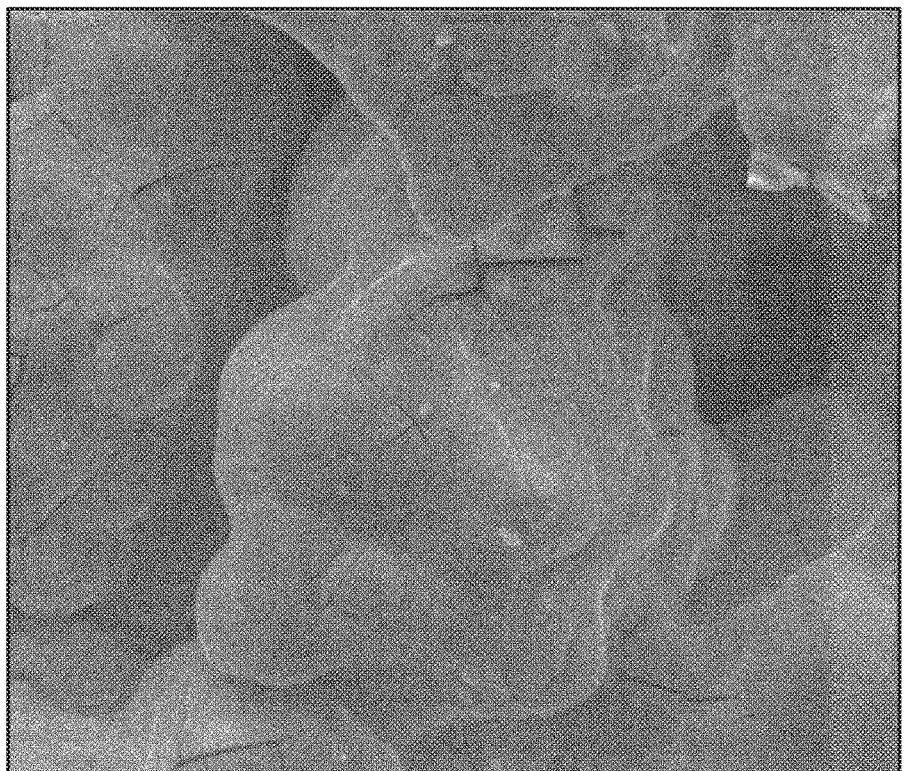
FIG. 28A is an SEM image of gallium-substituted SoDHA coating after hydrothermally treated at 70° C. for 2 hours in phosphate-Ga stock at 800× magnification.
Figure 28B:
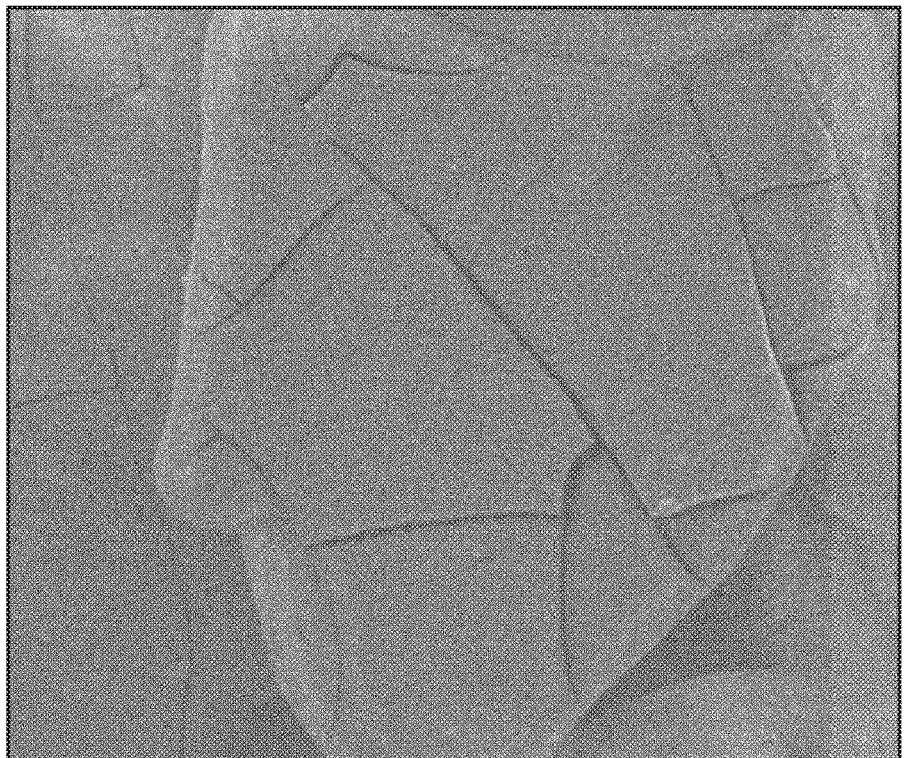
FIG. 28B is an SEM image of gallium-substituted SoDHA coating after hydrothermally treated at 70° C. for 2 hours in phosphate-Ga syrup at 1000× magnification.
Figure 29A:
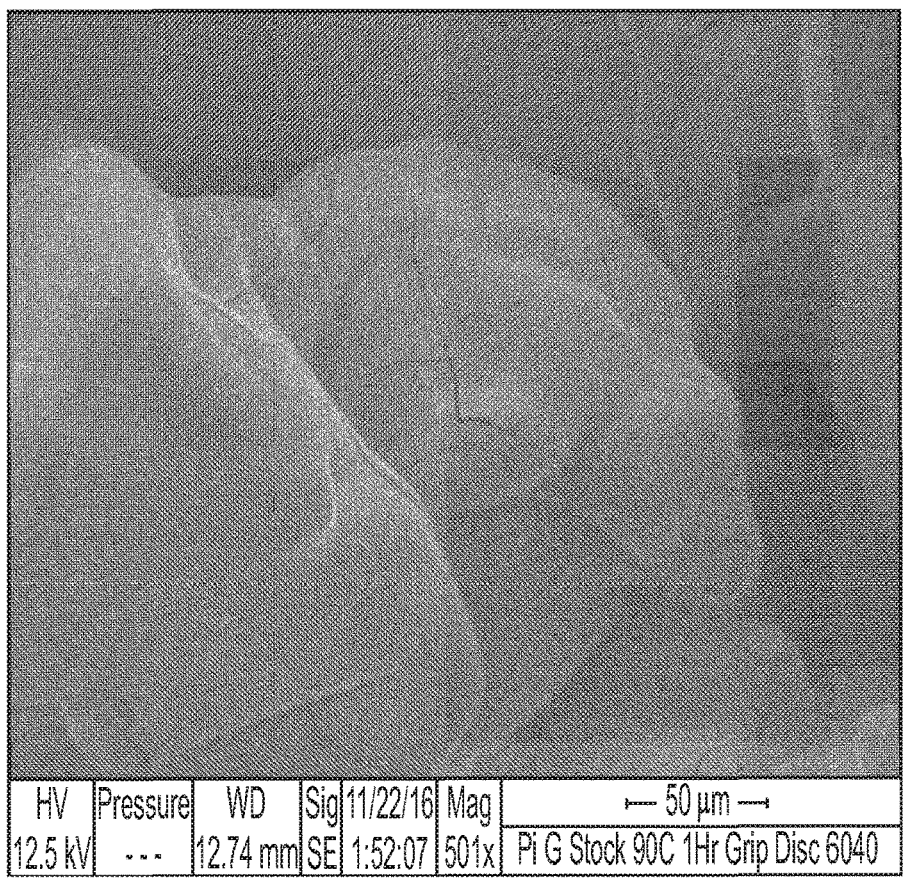
FIG. 29A is an SEM image of gallium-substituted SoDHA coating after hydrothermally treated at 90° C. for 1 hour in phosphate-Ga stock at 501× magnification.
Figure 29B:
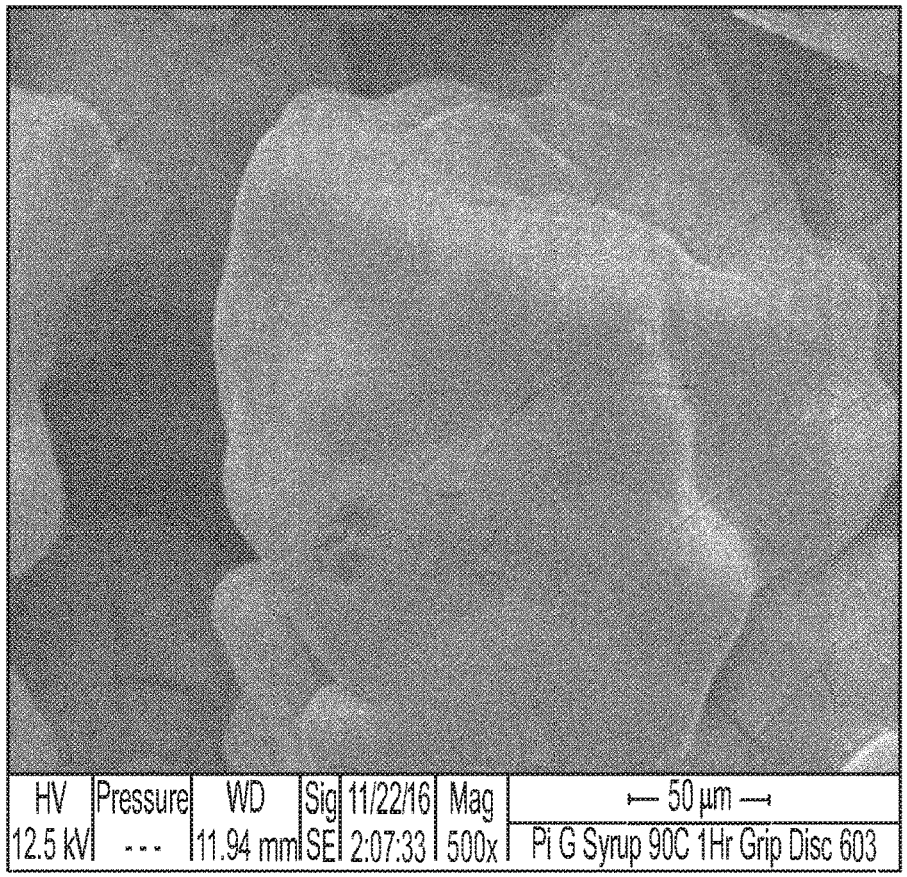
FIG. 29B is an SEM image of gallium-substituted SoDHA coating after hydrothermally treated at 90° C. for 1 hour in phosphate-Ga syrup at 500× magnification.
Figure 30A:
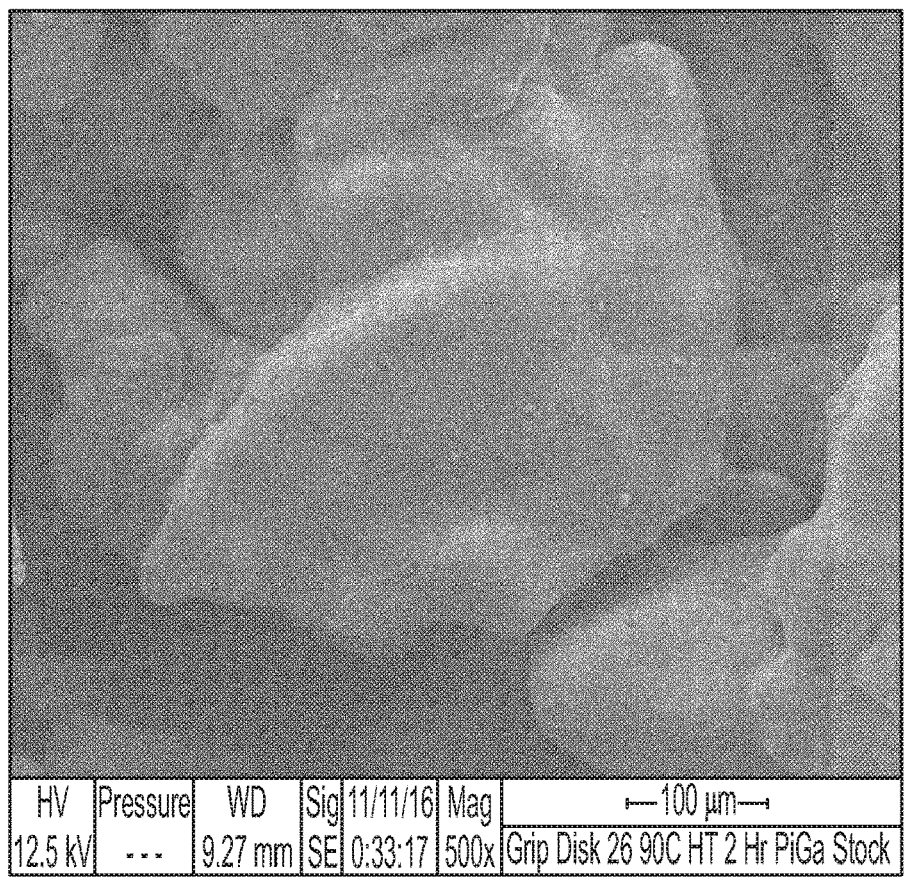
FIG. 30A is an SEM image of gallium-substituted SoDHA coating after hydrothermally treated at 90° C. for 2 hours in phosphate-Ga stock at 500× magnification.
Figure 30B:
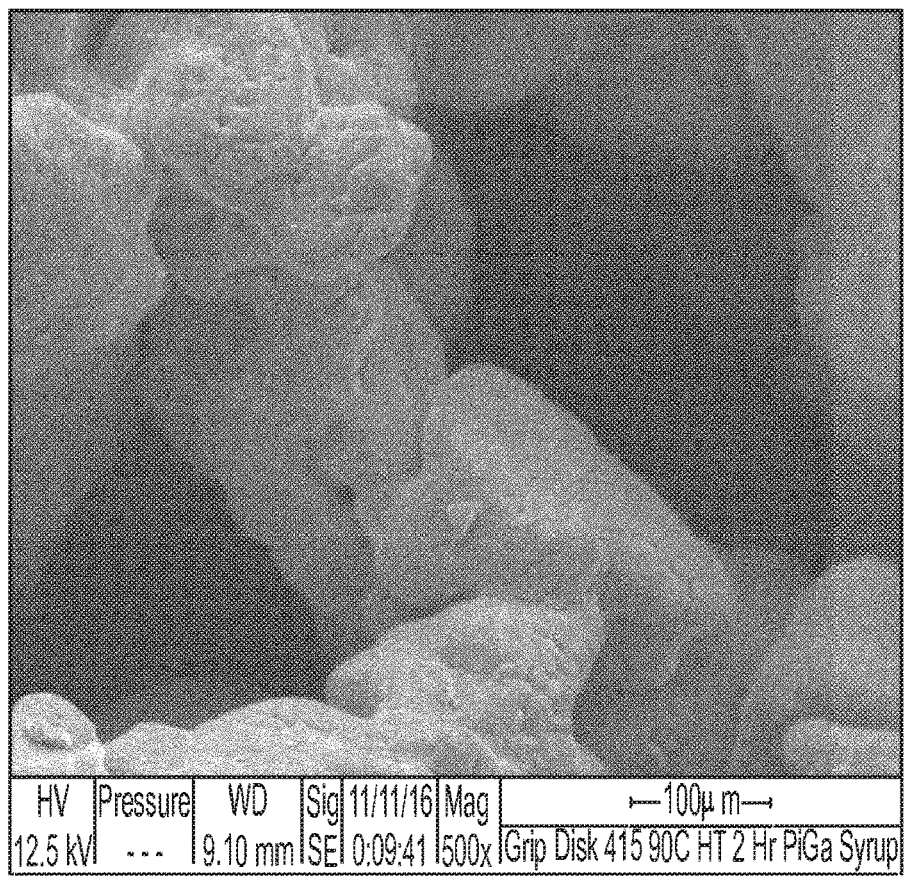
FIG. 30B is an SEM image of gallium-substituted SoDHA coating after hydrothermally treated at 90° C. for 2 hours in phosphate-Ga syrup at 500× magnification.
Figure 31:
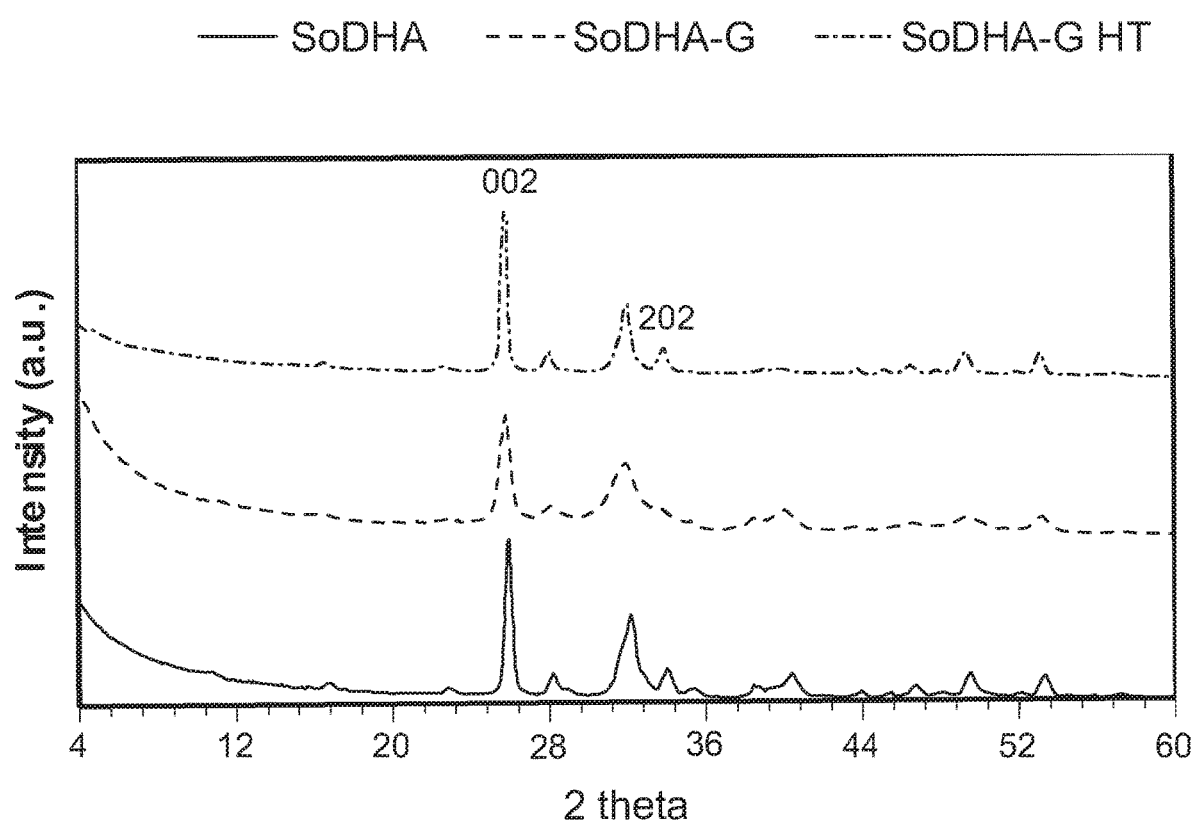
FIG. 31 superimposed XRD scans of a SoDHA coating without post-processing, a gallium-substituted SoDHA coating without post-processing, and a hydrothermally treated gallium substituted SoDHA coating.

The surface morphologies of the SoDHA-G and hydrothermally treated SoDHA-G (SoDHA-G-HT) films were examined by a scanning electron microscope (FE-SEM, Quanta 600 F). A scanning electron microscopy image for SoDHA-G is shown in FIG. 27. Scanning electron microscopy images for SoDHA-G-HT hydrothermally treated at 70° C. for 2 hours for films treated with phosphate-Ga stock and phosphate-Ga syrup are shown in FIGS. 28A and 28B, respectively. Scanning electron microscopy images for SoDHA-G-HT hydrothermally treated at 90° C. for 1 hour for films treated with phosphate-Ga stock and phosphate-Ga syrup are shown in FIGS. 29A and 29B, respectively. Scanning electron microscopy images for SoDHA-G-HT hydrothermally treated at 90° C. for 2 hours for films treated with phosphate-Ga stock and phosphate-Ga syrup are shown in FIGS. 30A and 30B, respectively. FIGS. 26-30B reveal the improvement to cracking as a function of optimizing temperature and time of hydrothermal treatment. The phase composition of the SoDHA and SoDHA-HT films was identified by X-ray diffractometry (Philips Analytical), using Cu Kα radiation at 45 kV, 40 mA. The X-ray diffraction patterns of SoDHA, SoDHA-G and SoDHA-G HT (hydrothermally treated in Pi-Ga stock at 90° C. for 2 hours) were collected between 4°-60° (2θ) at 0.02° step and 0.01°/s, as shown in FIG. 31. The XRD results indicated that the (002) peak of hydroxyapatite was not shifted after hydrothermal treatment, showing no appreciable Ga loss from the lattice.

Five (5) SoDHA-G coated Gription™ coupons prepared according to Example 12 were quickly transferred from DI water to a glass bottle containing 250 mL 2.2262 mM phosphate-Ga (Pi) stock prepared according to Example 4. Ten (10) SoDHA-G coated Gription™ coupons prepared according to Example 12 were quickly transferred from DI water to a glass bottle containing 250 mL 40 mM phosphate-Ga (Pi) syrup prepared according to Example 4. The glass bottles were then sealed with a cap. The hydrothermal treatment of SoDHA-G films was performed at 90° C. for 2 hours. After hydrothermal treatment, the SoDHA-G coated Gription™ coupons were rinsed excessively with DI water for one minute and placed in a 60° C. oven to dry for 1 hour.

Hydrothermally treated and regularly dried (no hydrothermal treatment) coatings were dissolved in 0.1 M hydrochloric acid and solutions analyzed for gallium with inductively coupled plasma (ICP) atomic emission spectroscopy. The gallium content of coatings without hydrothermal treatment and treated with phosphate-Ga stock were 2.58 wt % and 2.71 wt %, respectively. However, unexpectedly, the gallium content of coatings hydrothermally treated in phosphate-Ga syrup increased to 5.67 wt %. This revealed that hydrothermal treatment in concentrated gallium containing solutions was an effective method to increase the gallium content in hydroxyapatite coatings.

Example 21—Crack Quantification

Figure 32A:
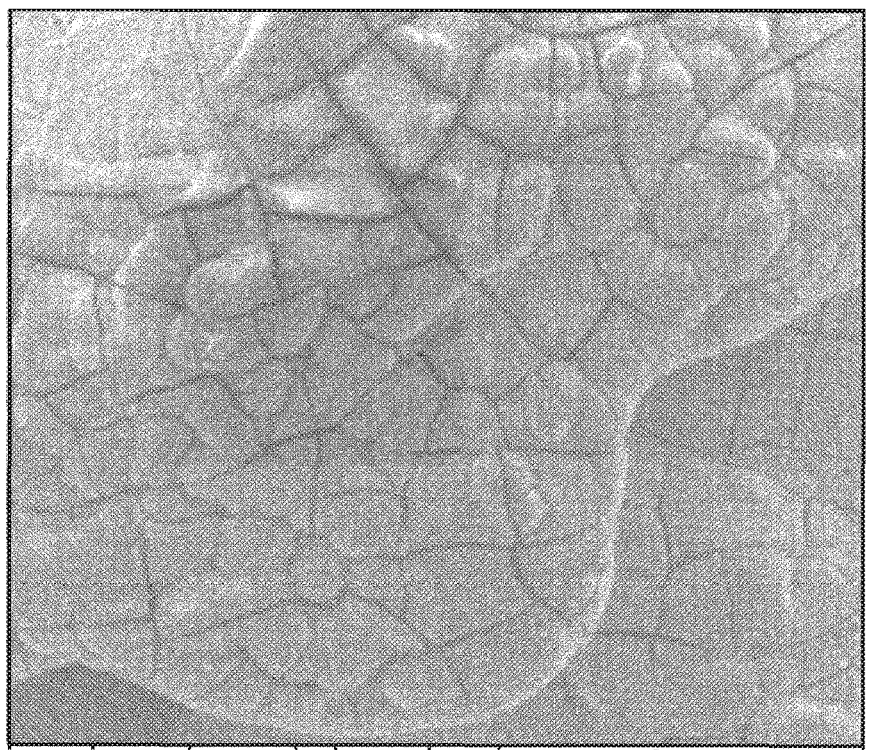
FIGS. 32A,B show representative images illustrating a crack density quantification method.
Figure 32B:
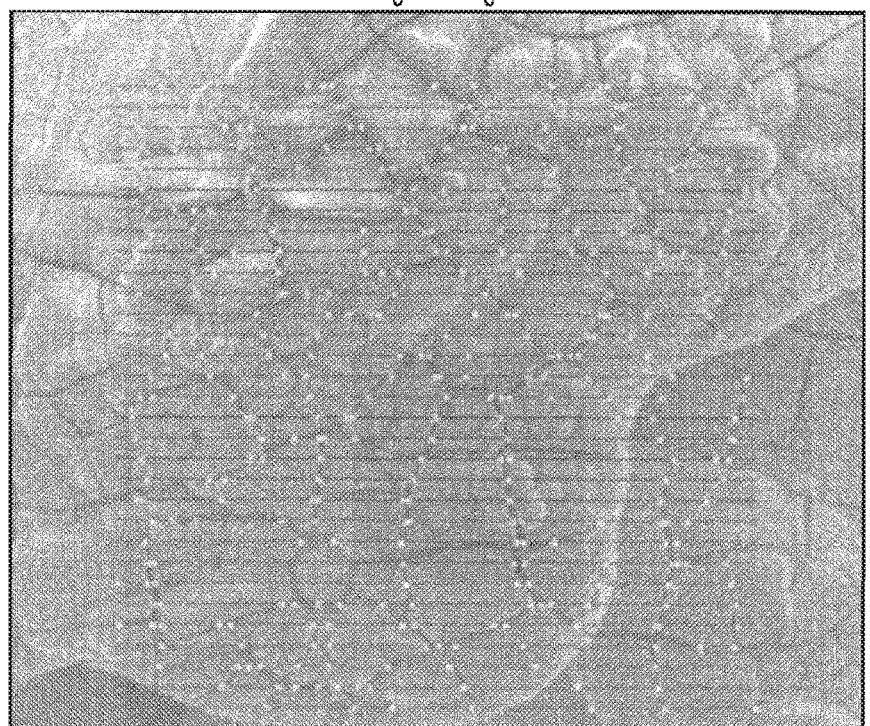

The crack improvement benefit of post treatment according to Examples 19 and 20 was quantified using image analysis by measuring the number of crack intersections on a predetermined horizontal grid. Images were taken at 1000× on the FEI Quanta 600 F SEM, and then imported into the Axio Vision software (AxioVision SE64 Release 4.9.1.0, from Carl Zeiss Microscopy GmbH) and 25 horizontal grid lines 193.5 in length and vertically 6 μm apart were placed over most of the image. The intercepts of the cracks in the image and grid lines were then manually marked. The intercepts were chosen manually by the operator to eliminate software driven errors. The number of intersections in this given area was used as a quantitative measure of the extent of surface cracking of SoDHA-G coatings. A representative image illustrating the method is shown in FIG. 32.

SoDHA-G coatings on grit blast coupons that underwent normal drying at 60° C. with no post-processing step exhibited over 600 intercepts, while hydrothermally treated SoDHA-G coatings revealed crack intercepts between 200 and 400. SoDHA-G with optimized hydrothermal treatment parameters exhibited minimal cracking, with fewer than 200 intercepts. The number of crack intersections and intercept density for representative regularly dried and post-processed coatings are shown in Table 9.

TABLE 9

Crack intercept count and density for various post-processed samples

| Sample | Number of Intercepts | Intercept density (intercepts/mm$^2$) |
|---|---|---|
| Grit blast sample - Flat 4050 SoDHA G100 60° C. oven dried-no post-processing step | 654 | 17467 |
| Grit blast sample - Flat 4054 SoDHA-G PiGa Syrup 85° C. 1 hr-hydrothermally treated (HT) | 348 | 9294 |
| Grit blast sample - Flat 4053 SoDHA-G PiGa Stock 90° C. 2 hr HT | 230 | 6142 |
| Acetabular cup sample - Cup 102 SoDHA-G100 PiGa Syrup 90° C. 2 hr HT | 30 | 801 |
| Acetabular cup sample - Cup 414 SoDHA-G100 PiGa Syrup 90° C. 2 hr HT | 108 | 2884 |
| Gription sample - Disk 26 SoDHA-G100 90° C. HT 2 hr PiGa Stock, Vacuum Treated | 60 | 1603 |

While the invention has been illustrated and described in detail in the drawings and foregoing description, such an illustration and description is to be considered as exemplary and not restrictive in character, it being understood that only the illustrative embodiments have been shown and described and that all changes and modifications that come within the spirit of the invention are desired to be protected.

There is a plurality of advantages of the present invention arising from the various features of the gallium-substituted HA coatings described herein. It will be noted that alternative embodiments of each of the coatings of the present invention may not include all of the features described yet benefit from at least some of the advantages of such features. Those of ordinary skill in the art may readily devise their own implementations of calcium phosphate coatings that incorporate one or more of the features of the present invention and fall within the spirit and scope of the present invention as defined by the appended claims.

What is claimed is:

1. An orthopedic implant comprising a porous metal surface and a hydroxyapatite layer disposed on at least part of the porous metal surface, the hydroxyapatite layer comprising gallium ions therein, wherein the hydroxyapatite layer is crystalline,
   wherein the hydroxyapatite layer, when subjected to X-Ray Diffraction (XRD), produces a (002) XRD peak and a (112) XRD peak, and the (002) XRD peak has an intensity 1.5 to 10 times greater than the (112) XRD peak.

2. The orthopedic implant of claim 1, wherein the hydroxyapatite, when subjected to XRD, produces a (002) XRD peak and a (112) XRD peak, and the (002) XRD peak has an intensity 2 to 5 times greater than the (112) XRD peak.

3. The orthopedic implant of claim 1, wherein the metal surface comprises a titanium alloy.

4. The orthopedic implant of claim 3, wherein the hydroxyapatite layer is in contact with the metal surface.

5. The orthopedic implant of claim 1, wherein the metal surface comprises a cobalt chromium alloy.

6. The orthopedic implant of claim 5, wherein the hydroxyapatite layer is in contact with the metal surface.

7. The orthopedic implant of claim 1, wherein the hydroxyapatite layer, when subjected to XRD, produces a (002) XRD peak that corresponds to a d-spacing shift of about 0.001 Å to about 0.05 Å compared to the (002) XRD peak of crystalline hydroxyapatite without gallium.

8. The orthopedic implant of claim 2, wherein the hydroxyapatite layer has an average crystallite size of less than about 75 nm.

9. The orthopedic implant of claim 2, wherein the hydroxyapatite layer has an average crystallite size of less than about 75 nm in the [001] direction in the XRD pattern.

10. An orthopedic implant comprising a surface and a hydroxyapatite layer disposed on at least part of the surface, the hydroxyapatite layer comprising gallium ions therein, wherein the hydroxyapatite layer is crystalline,
    wherein the hydroxyapatite layer, when subjected to X-Ray Diffraction (XRD), produces a (002) XRD peak and a (112) XRD peak, and the (002) XRD peak has an intensity 1.5 to 10 times greater than the (112) XRD peak.

11. The orthopedic implant of claim 10, wherein the surface comprises a titanium alloy.

12. The orthopedic implant of claim 11, wherein the surface is porous.

13. The orthopedic implant of claim 10, wherein the surface comprises a metal oxide.

14. The orthopedic implant of claim 13, wherein the surface is porous.

15. The orthopedic implant of claim 10, wherein the orthopedic implant comprises a polymer.

* * * * *